US007833727B2

(12) United States Patent
Ma et al.

(10) Patent No.: US 7,833,727 B2
(45) Date of Patent: *Nov. 16, 2010

(54) INCREASING LIFE SPAN BY MODULATION OF SMEK

(75) Inventors: Hui Ma, San Diego, CA (US); Tony Hunter, Del Mar, CA (US); Suzanne C. Wolff, Carlsbad, CA (US); Andrew Dillin, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 242 days.

This patent is subject to a terminal disclaimer.

(21) Appl. No.: 11/927,311

(22) Filed: Oct. 29, 2007

(65) Prior Publication Data

US 2008/0249012 A1    Oct. 9, 2008

Related U.S. Application Data

(63) Continuation of application No. 11/165,819, filed on Jun. 24, 2005, now Pat. No. 7,288,385.

(60) Provisional application No. 60/583,284, filed on Jun. 25, 2004.

(51) Int. Cl.
*G01N 33/53* (2006.01)
(52) U.S. Cl. ...................................... 435/7.1
(58) Field of Classification Search ............ 435/7.1
See application file for complete search history.

(56) References Cited

U.S. PATENT DOCUMENTS

| 4,736,866 | A | 4/1988 | Leder et al. |
| 4,870,009 | A | 9/1989 | Evans et al. |
| 4,873,191 | A | 10/1989 | Wagner et al. |
| 4,873,316 | A | 10/1989 | Meade et al. |

FOREIGN PATENT DOCUMENTS

| EP | 0264166 A1 | 4/1988 |
| EP | 0264166 B1 | 4/1988 |
| WO | WO-90/11354 A1 | 10/1990 |
| WO | WO-91/01140 A1 | 2/1991 |
| WO | WO-92/00968 A1 | 1/1992 |
| WO | WO-93/04169 A1 | 3/1993 |

OTHER PUBLICATIONS

Symbol Report: SMEK2, SMEK homolog 2, suppressor of mek1 (Dictyostelium), Accession No. AB 037808, Database: GenBank, Apr. 25, 2005.
Alonso, G. et al. (Dec. 22, 2000). "Differential Activation of p38 Mitogen-Activated Protein Kinase Isoforms Depending on Signal Strength," *Journal of Biological Chemistry* 275(51):40641-40648.
Banerji, J. et al. (Jul. 1983). "A Lymphocyte-Specific Cellular Enhancer is Located Downstream of the Joining Region in Immunoglobulin Heavy Chain Genes," *Cell* 33:729-740.
Bitter, G.A. et al. (1987). "Expression and Secretion Vectors for Yeast" Chapter 33 *In Methods in Enzymology*, Wu, R. ed. Academic Press, Inc., 153:516-544.
Bradley, A. (1987). "Production and Analysis of Chimaeric Mice" Chapter 5 *In Teratocarcinomas and Embryonic Stem Cells: A Practical Approach* Robertson, E.J. ed., IRL:Oxford pp. 113-152.
Bradley, A. (1991). "Modifying the Mammalian Genome by Gene Targeting," *Current Opinion in Biotechnology* 2(6):823-829.
Brunet, A. et al. (Mar. 19, 1999). "Akt Promotes Cell Survival by Phosphorylating and Inhibiting a Forkhead Transcription Favor," *Cell* 96(6):857-868.
Brunet, A. et al. (Mar. 26, 2004). "Stress-Dependent Regulation of FOXO Transcription Factors by the SIRT1 Deacetylase," *Science* 303(5666):2011-2015.
Burgering, B.M.T. et al. (Jul. 2002). "Cell Cycle and Death Control: Long Live Forkheads," *Trends in Biochemical Science* 27(7):352-360.
Byrne, G.W. et al. (Jul. 1989). "Multiplex Gene Regulation: A Two-Tiered Approach to Transgene Regulation in Transgenic Mice," *Proceedings of the National Academy of Sciences USA* 86:5473-5477.
Calame, K. et al. (1988). "Transcriptional Controlling Elements in the Immunoglobulin and T Cell Receptor Loci" *In Advances in Immunology*, Dixon, F.J. ed., Academic Press, Inc., 43:235-275.
Camper, S.A. et al. (Apr. 1989). "Postnatal Repression of the α-fetoprotein Gene is Enhancer Independent," *Genes & Development* 3(4):537-546.
Chang, L. et al. (Mar. 1, 2001). "Mammalian MAP Kinase Signalling Cascades," *Nature* 410:37-40.
Conkright, M.D. et al. (Aug. 2003). "TORCs: Transducers of Regulated CREB Activity," *Molecular Cell* 12(2):413-423.
Dijkers, P.F. et al. (2002). FKHR-L1 Can Act as a Critical Effector of Cell Death Induced by Cytokine Withdrawal: Protein Kinase B-Enhanced Cell Survival Through Maintenance of Mitochondrial Integrity, *The Journal of Cell Biology* 156(3):531-542.
Dillin, A. et al. (Dec. 20, 2002). "Rates of Behavior and Aging Specified by Mitochondrial Function During Development," *Science* 298(5602):2398-2401.
Dillin, A. et al. (Oct. 25, 2002). "Timing Requirements for Insulin/IGF-1 Signaling in *C. elegans*," *Science* 298(5594):830-834.
Edlund, T. et al. (Nov. 5, 1985). "Cell-Specific Expression of the Rat Insulin Gene: Evidence for Role of Two Distinct 5' Flanking Elements," *Science* 230(4727):912-916.

(Continued)

*Primary Examiner*—Maryam Monshipouri
(74) *Attorney, Agent, or Firm*—Morrison & Foerster LLP

(57) ABSTRACT

The Smek (Suppressor of mek null) gene is described and characterized. Smek acts in the stress response pathway of animals by binding to and enhancing the transcription of FOXO, thereby providing the link between the stress response pathway and the insulin/IGF-1 pathway. Given the link between both the stress response pathway and the insulin/IGF-1 pathway and longevity, Smek1 represents an essential target for modulation of life span and the stress response. Methods of increasing life span and stress tolerance by modulation of Smek activity are disclosed, as are screening methods for identifying compounds that modulate Smek activity. In addition, recombinant animals expressing the Smek gene that have a longer life span and enhanced stress tolerance, and methods of using the Smek gene to modulate both longevity and stress tolerance, are described.

5 Claims, 28 Drawing Sheets

OTHER PUBLICATIONS

Enslen, H. et al. (2000). "Molecular Determinants that Mediate Selective Activation of p38 MAP Kinase Isoforms," *EMBO Journal* 19(6):1301-1311.

Feng, J. et al. (Nov. 2001). "Mitochondrial Electron Transport Is a Key Determinant of Life Span in *Caenorhabditis elegans*," *Developmental Cell* 1:643-644.

Garsin, D.A. et al. (Jun. 20, 2003). "Long-Lived *C. elegans daf-2* Mutants Are Resistant to Bacterial Pathogens," *Science* 300(5627):1921.

Ghobrial et al. (2002). "Inhibitors of the Ras Oncogene as Therapeutic Targets," *Hematology / Oncology Clinics of North America* 16(5): 1065-1088.

Guarente, L. et al. (Nov. 9, 2000). "Genetic Pathways That Regulate Ageing in Model Organisms," *Nature* 408:255-262.

Hekimi, S. et al. (Feb. 28, 2003). "Genetics and the Specificity of the Aging Process," *Science* 299(5611):1351-1354.

Henderson, S.T. et al. (Dec. 11, 2001). "*daf-16* Integrates Developmental and Environmental Inputs to Mediate Aging in the Nematode *Caenorhabditis elegans*," *Current Biology* 11(24):1975-1980.

Hertweck, M. et al. (Apr. 2004). "*C. elegans* SGK-1 Is the Critical Component in the Akt/PKB Kinase Complex to Control Stress Response and Life Span," *Developmental Cell* 6:577-588.

Hsin, H. et al. (May 27, 1999) "Signals from the reproductive system regulate the lifespan *C. elegans.*" *Nature* 399:362-366.

International Search Report mailed on Jul. 26, 2006, for PCT Patent Application No. PCT/US05/22510 filed on Jun. 24, 2005. Two pages.

Jaye, M. et al. (1983). "Isolation of a Human Anti-Haemophilic Factor IX cDNA Clone Using a Unique 52-base Synthetic Oligonucleotide Probe Deduced From the Amino Acid Sequence of Bovine Factor IX," *Nucleic Acids Research* 11(8):2325-2335.

Jia, K. et al. (2004). "The TOR Pathway Interacts with the Insulin Signaling Pathway to Regulate *C. elegans* Larval Development, Metabolism and Life Span," *Development* 131:3897-3906.

Jiang, Y. et al. (Jul. 26, 1996). "Characterization of the Structure and Function of a New Mitogen-Activated Protein Kinase (p38β)," *Journal of Biological Chemistry* 271(30):17920-17926.

Jonassen, T. et al. (Jan. 16, 2001). "A Dietary Source of Coenzyme Q is Essential for Growth of Long-Lived *Caenorhabditis elegans clk-1* Mutants," *Proceedings of the National Academy of Sciences USA* 98(2):421-426.

Kamath, R.S. et al. (Jan. 16, 2003). "Systematic Functional Analysis of the *Caenorhabditis elegans* Genome Using RNAi," *Nature* 421:231-237.

Kenyon, C. (Apr. 20, 2001). "A Conserved Regulatory System for Aging," *Cell* 105(2):165-168.

Kessel, M. et al. (Jul. 27, 1990). "Murine Developmental Control Genes," *Science* 249:374-379.

Lakso, M. et al. (Jul. 1992). "Targeted Oncogene Activation by Site-Specific Recombination in Transgenic Mice," *Proceedings of the National Academy of Sciences USA* 89:6232-6236.

Lee, S.S. et al. (Jan. 2003). "A Systematic RNAi Screen Identifies a Critical Role for Mitochondria in *C. elegans* Longevity," *Nature Genetics* 33(1):40-48.

Li, E. et al. (Jun. 12, 1992). "Targeted Mutation of the DNA Methyltransferase Gene Results in Embryonic Lethality," *Cell* 69:915-926.

Libina, N. et al. (Nov. 14, 2003). "Tissue-Specific Activities of *C. elegans* DAF-16 in the Regulation of Lifespan," *Cell* 115(4):489-502.

Lin, K. et al. (Jun. 2001). "Regulation of the *Caenorhabditis elegans* Longevity Protein DAF-16 by Insulin/IGF-1 and Germline Signaling," *Nature Genetics* 28(2):139-145.

Marcus-Sekura, C.J. (Aug. 1, 1998). Review: Techniques for Using Antisense Oligodeoxyribonucleotides to Study Gene Expression, *Analytical Biochemistry* 172(2):289-295.

McCarroll, S.A. et al. (Feb. 2004). "Comparing Genomic Expression Patterns Across Species Identifies Shared Transcriptional Profile in Aging," *Nature Genetics* 36(2):197-204.

McElwee, J.J. et al. (Oct. 22, 2004). "Shared Transcriptional Signature in *Caenorhabditis elegans* Dauer Larvae and Long-Lived *daf-2* Mutants Implicates Detoxification System in Longevity Assurance," *Journal of Biological Chemistry* 279(43)44533-44543.

Meisenhelder, J. et al. (Jun. 30, 1989). "Phospholipase C-γ Is a Substrate for the PDGF and EGF Receptor Protein-Tyrosine Kinases In Vivo and In Vitro," *Cell* 57(7):1109-1122.

Mello, C. et al. (1991) "Efficient gene transfer in *C. elegans*: extrachromosomal maintenance and integration of transforming sequences." *The EMBO Journal* 10(12):3959-3970.

Mett, V.L. et al. (May 1993). "Copper-Controllable Gene Expression System for Whole Plants," *Proceedings of the National Academy of Sciences USA* 90:4567-4571.

Miyadera, H. et al. (Mar. 16, 2001). "Altered Quinone Biosynthesis in the Long-Lived *clk-1* Mutants of *Caenorhabditis elegans*," *Journal of Biological Chemistry* 276(11):7713-7716.

Morris et al. (2000). "Translocating Peptides and Proteins and Their Use for Gene Delivery," *Current Opinion in Biotechnology* 11: 461-466.

Morrison, D.K. et al. (2003). "Regulation of MAP Kinase Signaling Modules by Scaffold Proteins in Mammals," *Annual Review of Cell and Developmental Biology* 19:91-118.

Motta, M.C. et al. (Feb. 20, 2004). "Mammalian SIRT1 Represses Forkhead Transcription Factors," *Cell* 116(4):551-563.

Murphy, C.T. et al. (Jul. 17, 2003). "Genes that Act Downstream of DAF-16 to Influence the Lifespan of *Caenorhabditis elegans*," *Nature* 424:277-283.

Nasrin, N. et al. (Sep. 12, 2000). "DAF-16 Recruits the CREB-Binding Protein Coactivator Complex to the Insulin-like Growth Factor Binding Protein 1 Promoter in HepG2 Cells," *Proceedings of the National Academy of Sciences USA* 97(19):10412-10417.

O'Gorman, S. et al. (Mar. 15, 1991). "Recombinase-Mediated Gene Activation and Site-Specific Integration in Mammalian Cells," *Science* 251:1351-1355.

Parekh-Olmedo et al. (2005). "Gene Therapy Progress and Prospects: Targeted Gene Repair," *Gene Therapy* 12: 639-646.

Pinkert, C.A. et al. (May 1987). "An Albumin Enhancer Located 10 kb Upstream Functions Along with its Promoter to Direct Efficient, Liver-Specific Expression in Transgenic Mice," *Genes & Development* 1(3):268-277.

Puigserver, P. et al. (2003). "Peroxisome Proliferator-Activated Receptor-γ Coactivator 1α (PGC-1α): Transcriptional Coactivator and Metabolic Regulator," *Endocrine Reviews* 24(1):78-90.

Puigserver, P. et al. (May 29, 2003). "Insulin-Regulated Hepatic Gluconeogenesis Through FOXO1-PGC-1α Interaction," *Nature* 423:550-555.

Queen, C. et al. (Jul. 1983). "Immunoglobulin Gene Transcription Is Activated by Downstream Sequence Elements," *Cell* 33:741-748.

Schena, M. et al. (Dec. 1991). "A Steroid-Inducible Gene Expression System for Plant Cells," *Proceedings of the National Academy of Sciences USA* 88:10421-10425.

Simmer, F. et al. (2003). "Genome-Wide RNAi of *C. elegans* Using the Hypersensitive *rrf-3* Strain Reveals Novel Gene Functions," *Public Library of Science Biology* 1(1):77-84.

Smith et al. (2002). "Gene Transfer in Higher Animals: Theoretical Considerations and Key Concepts," *Journal of Biotechnology* 99: 1-22.

Thomas, K.R. et al. (Nov. 6, 1987). "Site-Directed Mutagenesis by Gene Targeting in Mouse Embryo-Derived Stem Cells," *Cell* 51(3):503-512.

Volkman, B.F. et al. (Nov. 15, 2002). "Structure of the N-WASP EVH1 Domain-WIP Complex: Insight into the Molecular Basis of Wiskott-Aldrich Syndrome," *Cell* 111(4):565-576.

Wallace, R.B. et al. (1981). "The Use of Synthetic Oligonucleotides as Hybridization Probes: II. Hybridization of Oligonucleotides of Mixed Sequence to Rabbit β-globin DNA," *Nucleic Acids Research* 9(4):879-894.

Wang, M.C. et al. (Nov. 2003). "JNK Signaling Confers Tolerance to Oxidative Stress and Extends Lifespan in *Drosophila*," *Developmental Cell* 5(5):811-816.

Weintraub, H.M. (Jan. 1990). "Antisense RNA and DNA," *Scientific American* 262:40-46.

Wilmut, I. et al. (Feb. 27, 1997). "Viable Offspring Derived From Fetal and Adult Mammalian Cells," *Nature* 385:810-813.

Winoto, A. et al. (1989). "A Novel, Inducible and T Cell-Specific Enhancer Located at the 3' End of the T Cell Receptor α Locus," *EMBO Journal* 8(3):729-733.

Fig. 1A Sequence alignment of Smek protein family

Fig. 1B Genomic location of human Smek genes
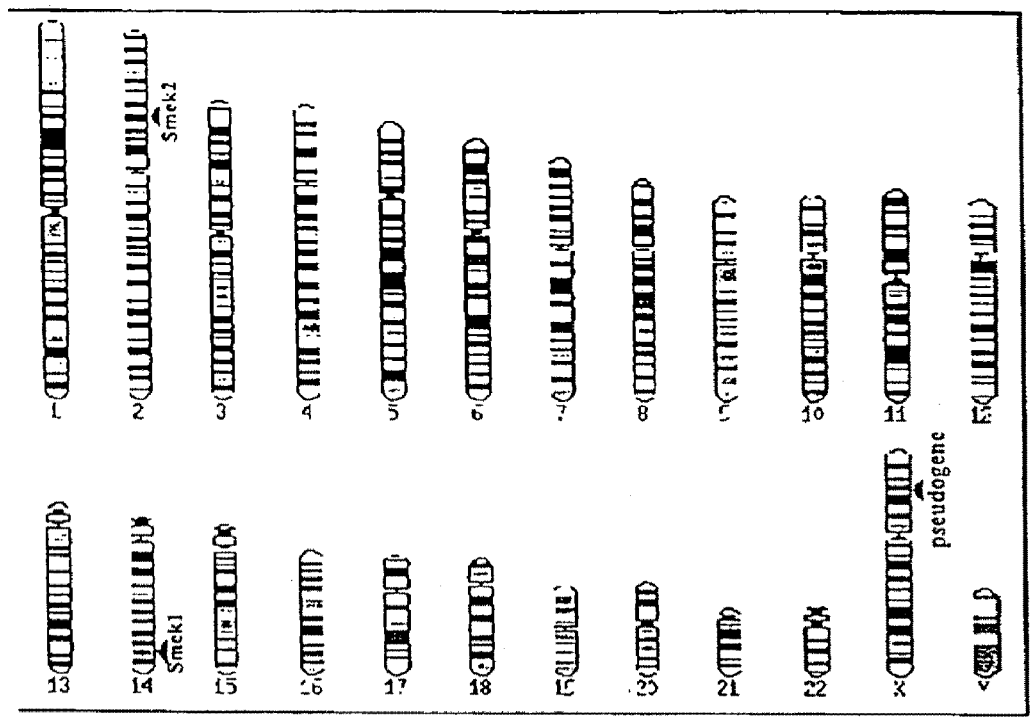
Fig. 1C Domain structure of human Smek1
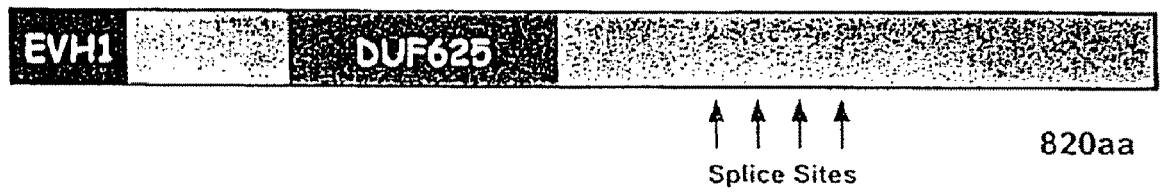

Fig2. Localization of Smek1 isoforms
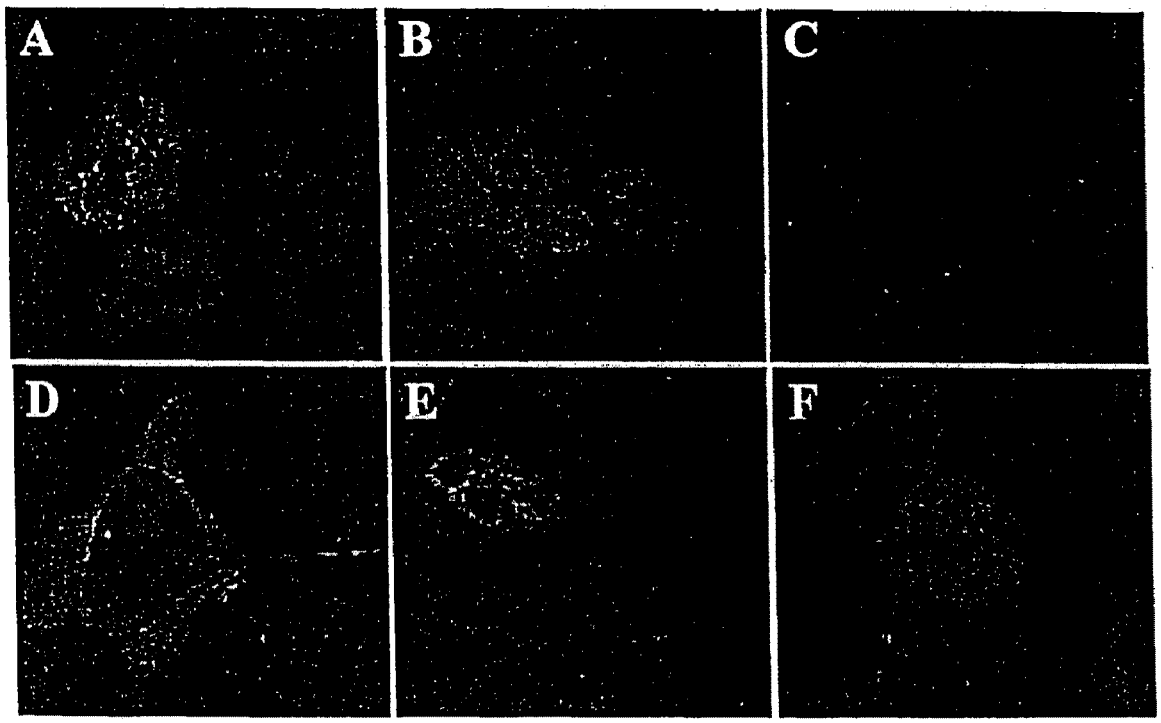

Fig. 3 Phosphorylation of Smek1 under stress conditions
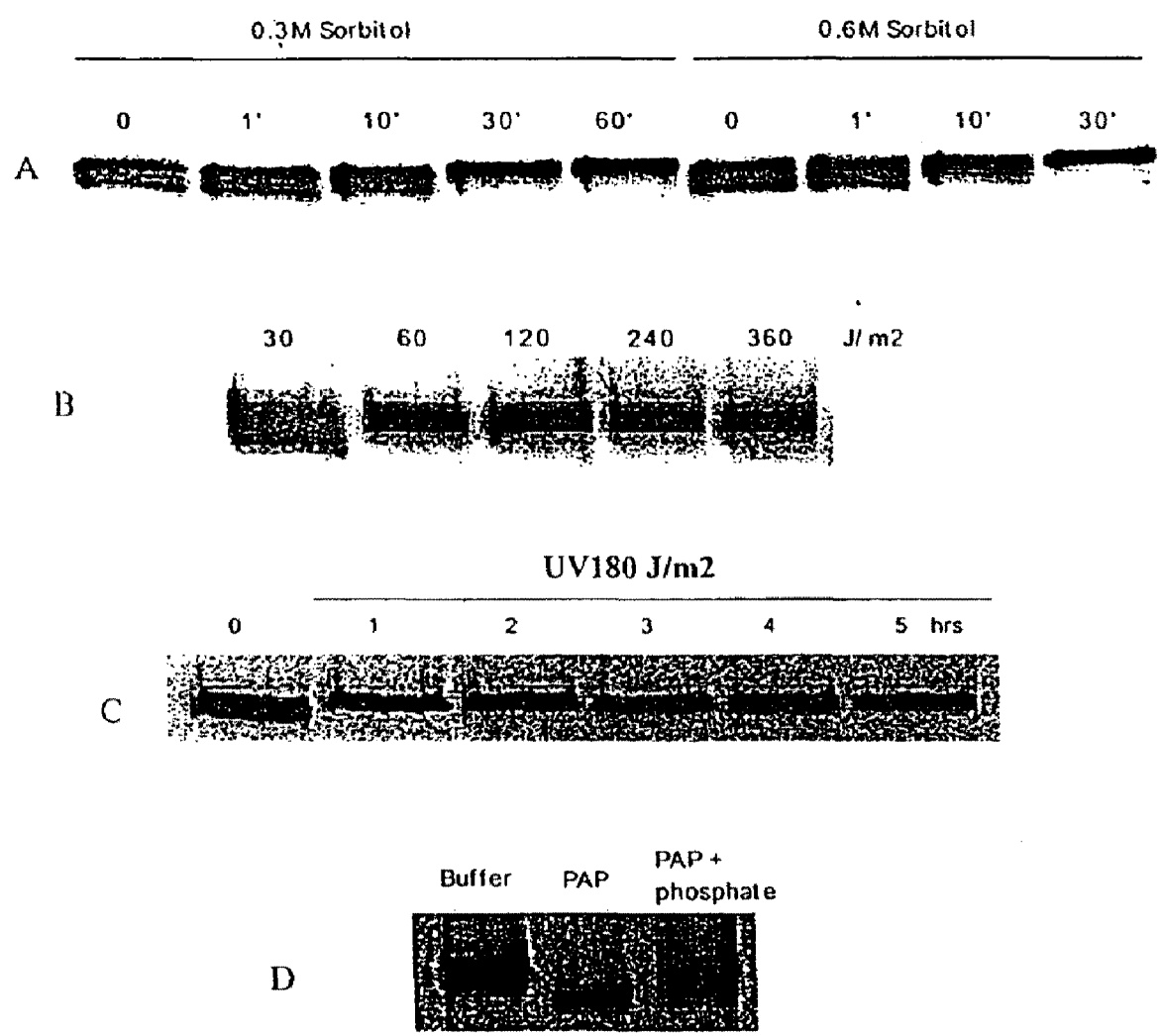

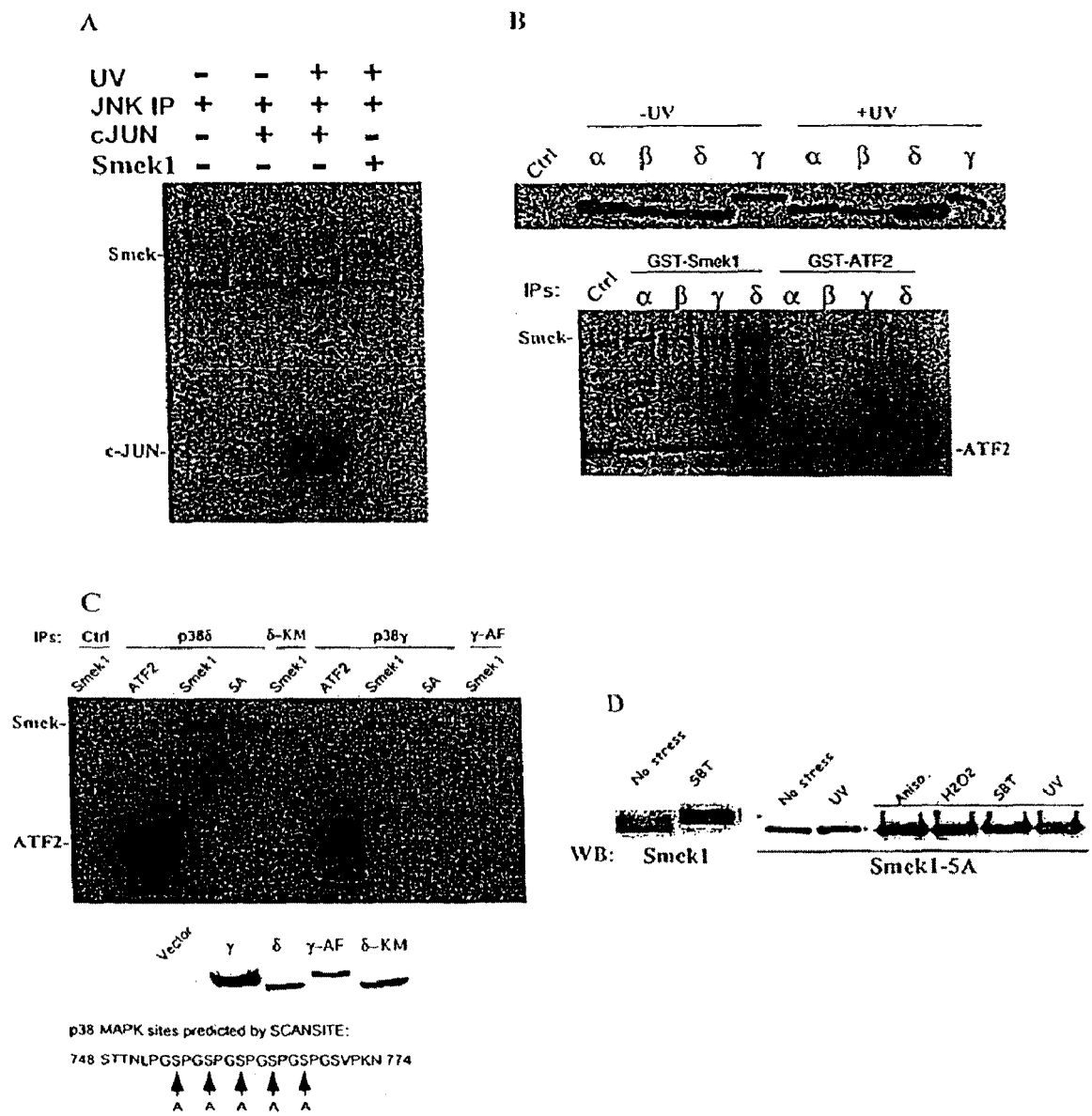
Fig. 4. Smek1 is a substrate for p38 MAP kinases in vitro

Fig.5 Smek1 interacts with FOXO protiens
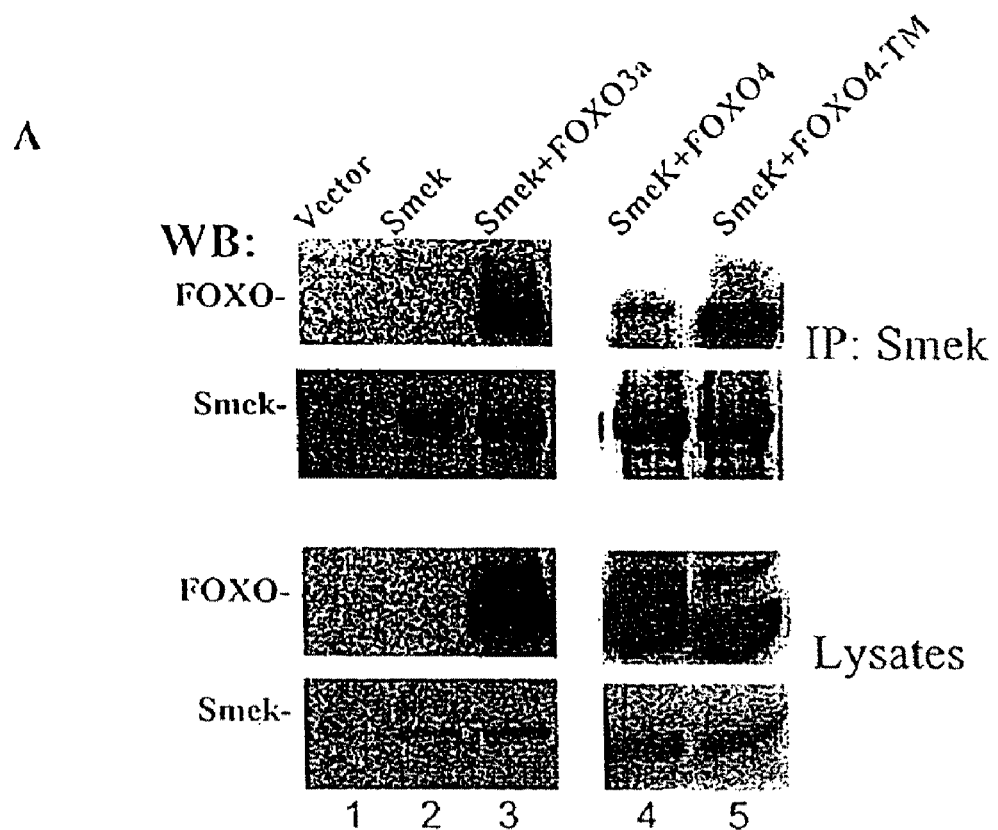
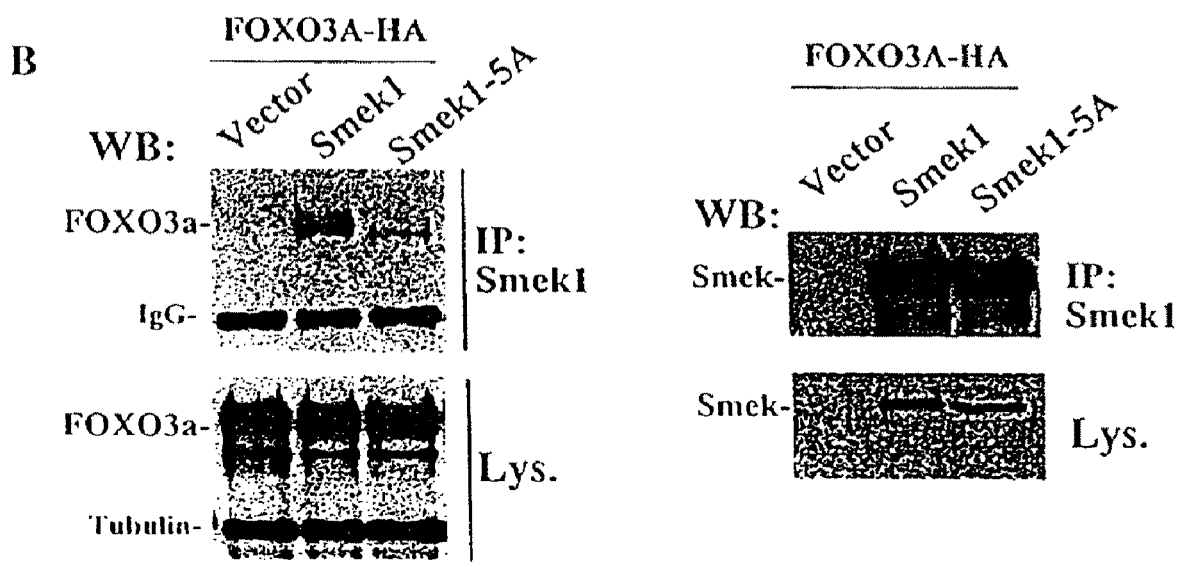

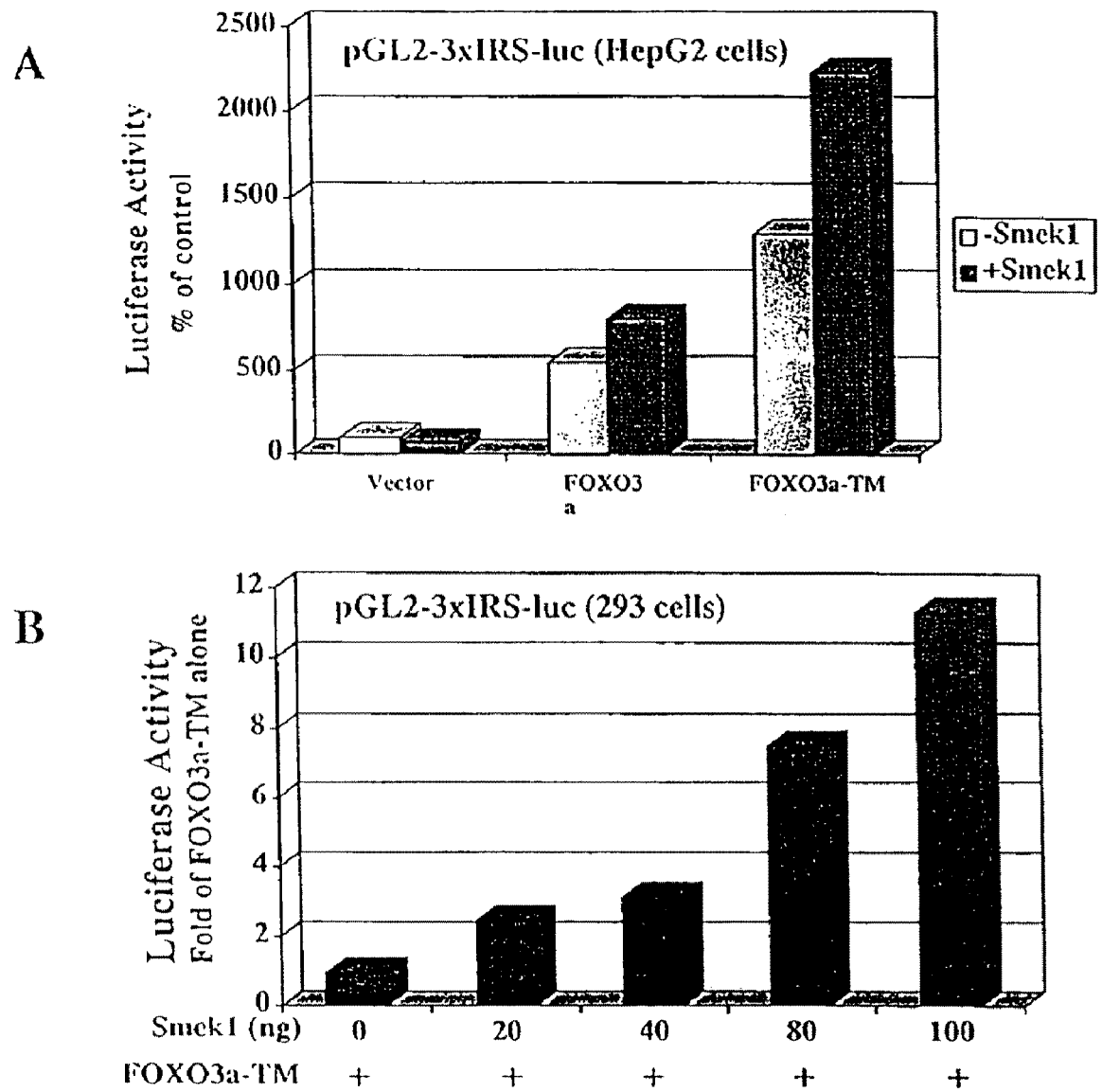
Figure 6: A and B

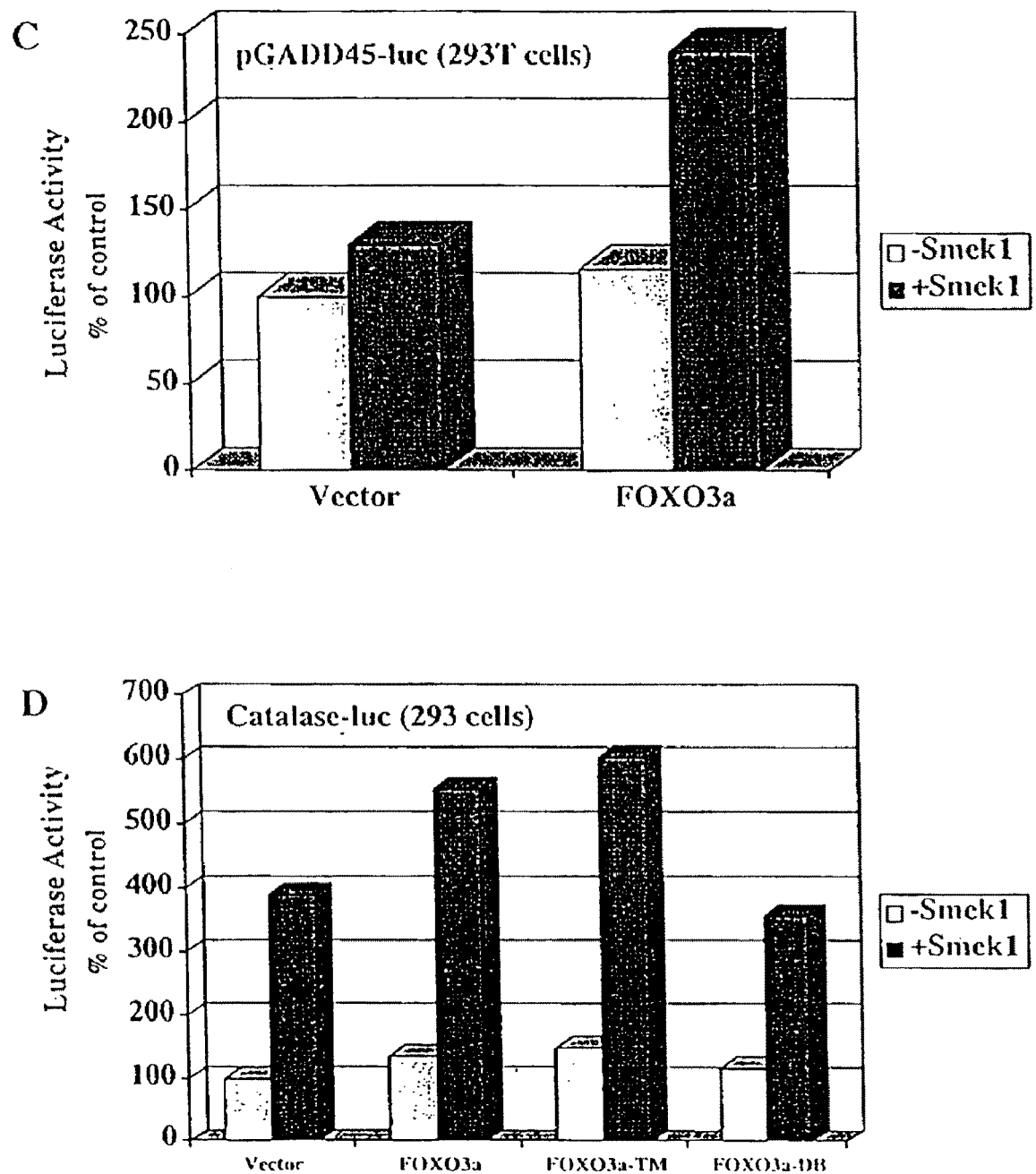
Figure 6: C and D

Fig. 7 Working Model
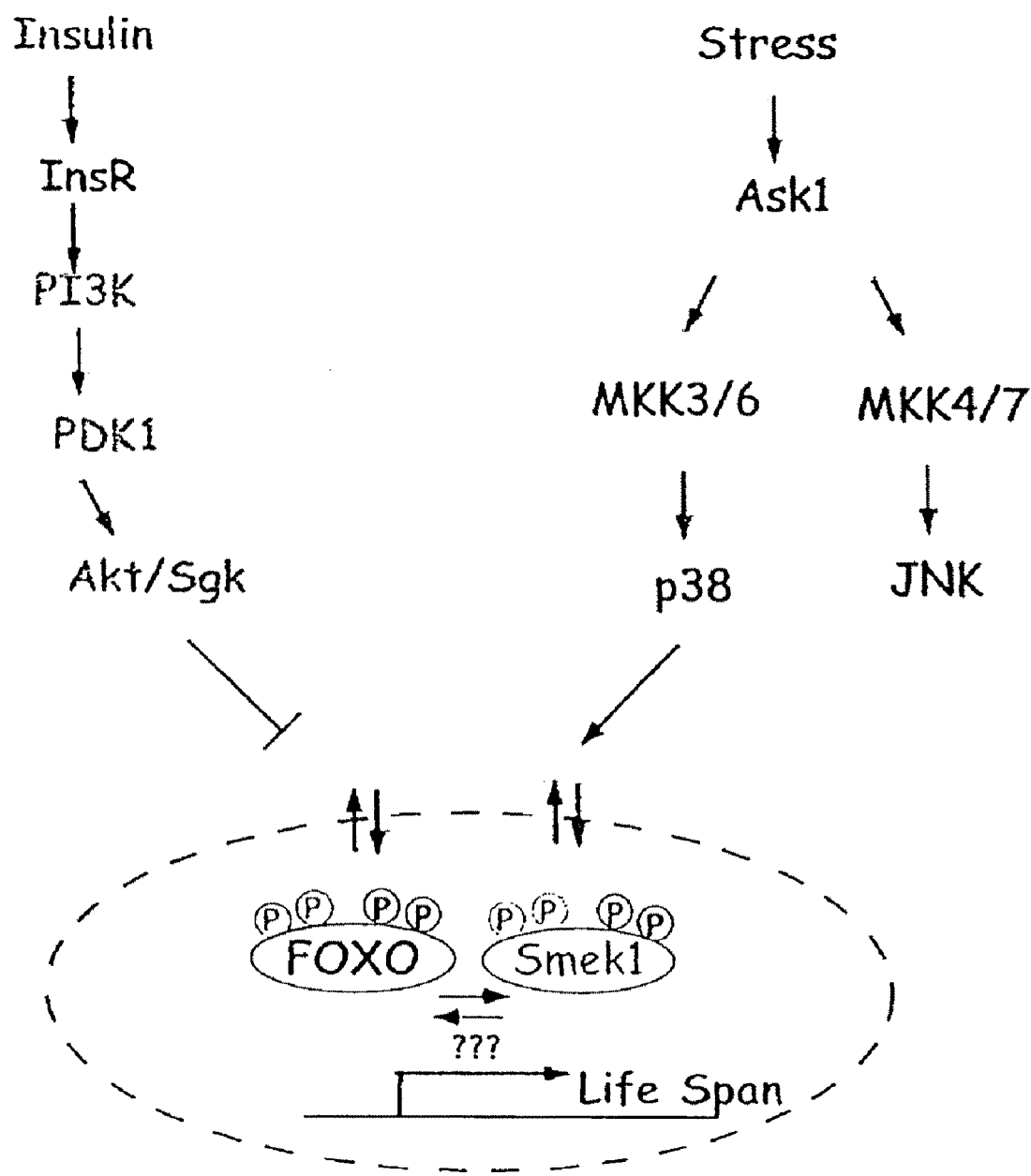

Figure 8

Predicted Dictyostelium (Dictyostelium discoideum) Smek1 protein sequence (SEQ ID NO 26)

MEPLRKRVKVYQLDNSGKWDDKGTGHVSCIYVDALCAMGLIVRSESDNSV
ILQTRLSAEDIYQKQQDSLIVWTEPDSQLDLALSFQDSLGCQDIWENILQ
YQNQRTGSCDSVDLDLPPVSINNLQTINELLEASLPMLDKDKIINSIFKE
DLVRSLLDLFDEIEKSGEGGVHLFQIFNIFKNLILFNDTSILEVILSEDY
LVRVMGALEYDPEISENNRIKHREFLNQQVVFKQVIKFPSKSLIGTIHQT
FRIQYLKDVVLPRVLDDVTFSSLNSLIYFNNIDIVSQIQNDSDFLENLFS
EIQKSEKNSEERKDLILFLQDLCNLAKGLQIQSKSTFFTVVVSLGLFKTL
SAILDDENVQTRVSCTEIVLSTLLHDPEILRSYLCSPTSGNSKFLVQLIN
LFITDKDIGVKNQIVEIIKTLLEADSYDSSDFFRLFYDKGIDLLVSPLNE
VYKGEPTIPGDPSSNLDSFVLYNIMELVIYCIKHHCYRIKHFIVEEGIAK
KILRYTNPTGSGGGGGGGGNSERYLILGSIRFFRSMVNMKDDLYNQHIIQ
ENLFEPIIEVFKSNISRYNLLNSAIIELFQYIYKENIRDLIVYLVERYRE
LFESVTYTDVLKQLILKYEQIKDSSFESPETSCNNNDSSSNDIDSKPIIG
NNKINHNYQRTQREIDEEEEAYFNRDDDSEDSDDEDELIPISINNNNNN
NNNNKQICTNNENNMEKNDDNIEKDNENTNNGNGSSHIKIVDYEDEDDED
DEINKSVESDDIVEKHEIIDKNEKKDEIMKENNDSDNDDNDNNDNDNDND
NNSDIENKNHLNNNGNNENNENNDDVQDKSNNKNNSDKINEDEKIEKQDE
MKENLEMEEIDEKVKEKQPKDIKKENQSQPDETVFNGKSNNSNNNNNNNN
NNSNNQEIGDNRKTTPKRKLDYEKNESVVSKKIDKSNGPTSIDKDINGCD
ESPNKKLNNNNSNNNNNNNNNNNNNNNNNNNNNNNNNNNNNNNQNDENEL
SSASEEEEEQLENGKHIKKFKRGKKDSNNSSNNSNNSSPTPSELHV*

Figure 9A

Human (Homo sapiens) Smek1 cDNA sequence (SEQ ID NO 27)

ATGACCGACACCCGGCGGCGGGTGAAGGTGTACACGCTCAACGAGGACCG
GCAGTGGGACGACCGGGGCACCGGGCATGTGTCGTCTGGCTACGTGGAGC
GGCTGAAGGGCATGTCCCTGCTTGTCAGGGCTGAGAGCGACGGTTCTCTA
CTTTTAGAGTCGAAAATAAATCCTAACACTGCATACCAGAAACAACAGGA
CACTCTGATTGTGTGGTCTGAAGCAGAAAATTATGACTTGGCCCTTAGCT
TTCAAGAAAAGCTGGATGTGATGAAATTGGGAGAAAATATGTCAGGTT
CAAGGAAAGGACCCTTCCGTGGACATCACTCAGGACCTTGTGGATGAATC
TGAAGAGGAGCGTTTTGATGATATGTCATCGCCAGGCTTAGAATTGCCAT
CTTGTGAATTAAGTCGCCTTGAAGAAATTGCAGAACTTGTGGCATCATCT
TTACCTTCACCTCTTCGTCGTGAAAAACTTGCACTGGCACTAGAAAATGA
GGGTTATATTAAAAAGCTCCTGGAGCTTTTCATGTGTGTGAAGATTTGG
AAAATATTGAAGGACTGCACCACTTGTATGAAATTATCAAAGGCATCTTT
CTCTTGAATCGAACTGCTCTTTTTGAAGTTATGTTCTCTGAAGAATGTAT
AATGGACGTCATTGGATGTTTAGAATATGATCCTGCTTTATCACAACCAC
GAAAACACAGGGAATTTCTAACAAAAACAGCCAAGTTTAAAGAAGTGATT
CCCATATCAGATCCTGAGCTGAAACAAAAAATTCATCAGACATACAGAGT
TCAGTATATACAAGATATGGTTCTACCAACTCCTTCGGTCTTTGAAGAAA
ACATGTTATCAACACTTCACTCTTTATCTTTTCAATAAGGTAGAGATT
GTTGGCATGTTGCAGGAAGATGAAAAATTTCTGACAGATTTGTTTGCACA
ACTAACAGATGAAGCAACAGATGAGGAAAAAGACAGGAATTGGTTAACT
TTTTAAAAGAATTTTGTGCGTTTTCCCAAACGCTACAGCCTCAAAACAGA
GATGCTTTTTTCAAGACTTTGTCAAACATGGGCATATTACCAGCTTTAGA
AGTCATCCTTGGCATGGATGATACACAGGTGCGAAGTGCTGCTACTGATA
TATTCTCATACTTGGTTGAATATAATCCATCCATGGTACGAGAGTTTGTC
ATGCAGGAGGCACAACAGAATGATGATGATATTTTGCTCATCAACCTCAT
TATAGAACATATGATTTGTGATACAGATCCTGAACTTGGAGGAGCAGTCC
AGCTTATGGGCCTGCTTCGAACTTTAGTTGACCCAGAGAACATGCTAGCC
ACTGCCAATAAAACAGAAAGACTGAATTTCTGGGTTTCTTCTACAAGCA
CTGTATGCATGTTCTCACTGCTCCTTTACTAGCAAATACAACAGAAGACA

Figure 9B

Human (Homo sapiens) Smek1 cDNA sequence continued (SEQ ID NO 27)

AACCTAGTAAAGATGATTTTCAGACTGCCCAACTATTGGCACTTGTATTG
GAATTGTTAACATTTTGTGTGGAGCACCATACCTACCACATAAAGAACTA
CATTATTAATAAGGATATCCTCCGGAGAGTGCTAGTTCTTATGGCCTCGA
AGCATGCTTTCTTGGCATTATGTGCCCTTCGTTTTAAAAGAAAGATTATT
GGATTAAAAGATGAGTTTTACAACCGCTACATAATGAAAGTTTTTTGTT
TGAACCAGTAGTGAAAGCATTTCTAACAATGGATCCCGCTACAATCTGA
TGAACTCTGCCATAATAGAGATGTTTGAATTTATTAGAGTGGAAGATATA
AAATCATTAACTGCTCATGTAATTGAAAATTACTGGAAAGCACTGGAAGA
TGTAGATTATGTACAGACATTTAAAGGATTAAAACTGAGATTTGAACAAC
AAAGAGAAAGGCAAGATAATCCCAAACTTGACAGTATGCGTTCCATTTTG
AGGAATCACAGATATCGAAGAGATGCCAGAACACTAGAAGATGAAGAAGA
GATGTGGTTTAACACAGATGAAGATGACATGGAAGATGGAGAAGCTGTAG
TGTCTCCATCTGACAAAACTAAAAATGATGATGATATTATGGATCCAATA
AGTAAATTCATGGAAAGGAAGAAATTAAAAGAAAGTGAGGAAAAGGAAGT
GCTTCTGAAAACAAACCTTTCTGGACGGCAGAGCCCAAGTTTCAAGCTTT
CCCTGTCCAGTGGAACGAAGACTAACCTCACCAGCCAGTCATCTACAACA
AATCTGCCTGGTTCTCCGGGATCACCTGGATCCCCAGGATCTCCAGGCTC
TCCTGGATCCGTACCTAAAAATACATCTCAGACGGCAGCTATTACTACAA
AGGGAGGCCTCGTGGGTCTGGTAGATTATCCTGATGATGATGAAGATGAT
GATGAGGATGAAGATAAGGAAGATACGTTACCATTGTCAAAGAAAGCAAA
ATTTGATTCATAA

Figure 10A

Human (Homo sapiens) Smek2 cDNA sequence (SEQ ID NO 28)

ATGTCGGATACGCGGCGGCGAGTGAAGGTCTATACCCTGAACGAAGACCG
GCAATGGGACGACCGAGGCACCGGGCACGTCTCCTCCACTTACGTGGAGG
AGCTCAAGGGGATGTCGCTGCTGGTTCGGGCAGAGTCCGACGGATCACTA
CTCTTGGAATCAAAGATAAATCCAAATACTGCATATCAGAAACAACAGGA
TACATTAATTGTTTGGTCAGAAGCAGAGAACTATGATTTGGCTCTGAGTT
TTCAGGAGAAAGCTGGCTGTGATGAGATCTGGGAAAAATTTGTCAGGTT
CAAGGTAAAGACCCATCAGTGGAAGTCACACAGGACCTCATTGATGAATC
TGAAGAAGAACGATTTGAAGAAATGCCTGAAACTAGTCATCTGATTGACC
TGCCCACGTGTGAACTCAATAAACTTGAAGAGATTGCTGACTTAGTTACC
TCAGTGCTCTCCTCACCTATCCGTAGGGAAAAGCTGGCTCTCGCCTTGGA
AAATGAAGGCTATATTAAAAAACTATTGCAGCTGTTCCAAGCTTGCGAGA
ACCTAGAAAACACTGAAGGCTTACACCATTTGTATGAAATTATTAGAGGA
ATCTTATTCCTAAATAAGGCAACTCTTTTGAGGTAATGTTTCTGATGA
GTGTATCATGGATGTCGTGGGATGCCTTGAATATGACCCTGCTTGGCTC
AGCCAAAAAGACATAGAGAATTCTTGACCAAAACTGCAAAGTTCAAGGAA
GTTATACCAATAACAGACTCTGAACTAAGGCAAAAAATACATCAGACTTA
CAGGGTACAGTACATTCAGGACATCATTTGCCCACACCATCTGTTTTTG
AAGAGAATTTTCTTTCTACTCTTACGTCTTTTATTTTCTTCAACAAAGTT
GAGATAGTCAGCATGTTGCAGGAAGATGAGAAGTTTTGTCTGAAGTTTT
TGCACAATTAACAGATGAGGCTACAGATGATGATAAACGGCGTGAATTGG
TTAATTTTTTCAAGGAGTTTTGTGCATTTCTCAGACATTACAACCTCAA
AACAGGGATGCATTTTTCAAAACATTGGCAAAATTGGGAATTCTTCCTGC
TCTTGAAATTGTAATGGGCATGGATGATTTGCAAGTCAGATCAGCTGCTA
CAGATATATTTTCTTATCTAGTAGAATTTAGTCCATCTATGGTCCGAGAG
TTTGTAATGCAAGAAGCTCAGCAGAGTGATGACGATATTCTTCTTATTAA
TGTGGTAATTGAACAAATGATCTGTGATACTGATCCTGAGCTAGGAGGCG
CTGTTCAGTTAATGGGACTTCTTCGTACTCTAATTGATCCAGAGAACATG
CTGGCTACAACTAATAAACCGAAAAAGTGAATTTCTAAATTTTTTCTA
CAACCATTGTATGCATGTTCTCACAGCACCACTTTTGACCAATACTTCAG
AAGACAAATGTGAAAAGGATTTTTTTTTAAAACATTACAGATATAGTTGG

Figure 10B

Human (Homo sapiens) Smek2 cDNA sequence continued (SEQ ID NO 28)

AGTTTCGTATGTACCCCTTCACATTCCCATTCCCATTCTACCCCCTCTTC
CTCCATCTCTCAAGATAATATAGTTGGATCAAACAAAAACAACACAATTT
GTCCCGATAATTATCAAACAGCACAGCTACTTGCCTTAATTTTAGAGTTA
CTCACATTTTGTGTGGAACATCACACATATCACATAAAAAACTATATTAT
GAACAAGGACTTGCTAAGAAGAGTCTTGGTCTTGATGAATTCAAAGCACA
CTTTTCTGGCCTTGTGTGCCCTTCGCTTTATGAGGCGGATAATTGGACTT
AAAGATGAATTTTATAATCGTTACATCACCAAGGGAAATCTTTTTGAGCC
AGTTATAAATGCACTTCTGGATAATGGAACTCGGTATAATCTGTTGAATT
CAGCTGTTATTGAGTTGTTTGAATTTATAAGAGTGGAAGATATCAAGTCT
CTTACTGCCCATATAGTTGAAAACTTTTATAAAGCACTTGAATCGATTGA
ATATGTTCAGACATTCAAAGGATTGAAGACTAAATATGAGCAAGAAAAG
ACAGACAAAATCAGAAACTGAACAGTGTACCATCTATATTGCGTAGTAAC
AGATTTCGCAGAGATGCAAAAGCCTTGGAAGAGGATGAAGAAATGTGGTT
TAATGAAGATGAAGAAGAGGAAGGAAAAGCAGTTGTGGCACCAGTGGAAA
AACCTAAGCCAGAAGATGATTTTCCAGATAATTATGAAAAGTTTATGGAG
ACTAAAAAAGCAAAAGAAAGTGAAGACAAGGAAAACCTTCCCAAAAGGAC
ATCTCCTGGTGGCTTCAAATTTACTTTCTCCCACTCTGCCAGTGCTGCTA
ATGGAACAAACAGTAAATCTGTAGTGGCTCAGATACCACCAGCAACTTCT
AATGGATCCTCTTCCAAAACCACAAACTTGCCTACGTCAGTAACAGCCAC
CAAGGGAAGTTTGGTTGGCTTAGTGGATTATCCAGATGATGAAGAGGAAG
ATGAAGAAGAAGAATCGTCCCCAGGAAAAGACCTCGTCTTGGCTCATAA

Figure 11A

Predicted Dictyostelium (Dictyostelium discoideum) Smek1 cDNA sequence (SEQ ID NO 29)

ATGGAACCACTTAGAAAAAGAGTTAAAGTCTATCAATTAGATAATAGCGG
AAAGTGGGATGATAAAGGTACAGGTCATGTATCATGTATATATGTAGATG
CATTATGTGCAATGGGATTAATTGTTAGATCAGAGAGTGATAACAGTGTA
ATTTTACAAACTCGACTATCAGCAGAGGATATATCAAAAACAACAAGA
TTCCTTAATCGTTTGGACAGAACCAGATTCACAATTAGATTTAGCCCTAT
CATTTCAAGATTCATTGGGTTGTCAGGATATTTGGGAGAACATATTACAA
TATCAAAATCAAAGAACTGGTAGTTGTGATAGTGTAGATTTAGATTTACC
ACCAGTTTCAATCAATAATCTTCAAACAATTAATGAATTATTAGAAGCTT
CATTACCAATGTTAGATAAAGATAAAATTATAAATTCAATTTTTAAAGAG
GATTTAGTAAGATCATTATTAGATTTATTTGATGAAATTGAAAAATCAGG
TGAAGGAGGAGTTCACTTGTTTCAAATATTCAATATTTTAAAAACCTTA
TTTTATTCAATGATACATCAATTTTAGAGGTTATTTTATCAGAAGATTAT
TTAGTAAGAGTTATGGGTGCATTAGAATATGACCCAGAAATTTCAGAAAA
TAATAGAATTAAACATAGAGAATTTTTAAATCAACAAGTAGTTTTTAAAC
AAGTTATAAAGTTCCCATCAAAATCATTAATTGGAACTATTCATCAAACA
TTTAGAATTCAATATCTAAAAGATGTTGTTTTACCAAGAGTATTGGATGA
TGTCACTTTCTCATCATTAAATTCATTAATTTATTTTAATAATATAGATA
TAGTTTCACAAATTCAAAATGATTCAGATTTTTTAGAAAATTTATTTTCA
GAAATCCAAAAAAGTGAAAAGAATTCAGAAGAAAGAAAAGATTTAATATT
ATTTCTTCAAGATTTATGTAATTTAGCAAAAGGATTACAAATTCAAAGTA
AATCAACATTTTTTACAGTTGTAGTTTCATTAGGATTATTTAAAACTTTA
TCAGCAATCTTGGATGATGAAAATGTACAAACCAGAGTATCATGTACAGA
GATTGTATTATCGACATTATTACATGATCCAGAAATTTTAAGATCATATC
TATGTTCTCCAACCAGTGGAAATAGTAAATTCTTGGTTCAATTAATAAAT
TTATTCATAACTGATAAAGATATTGGTGTTAAAAATCAAATTGTTGAAAT
TATTAAAACTTTATTGGAAGCTGATTCTTATGATTCAAGCGATTTCTTTA
GATTATTTTATGATAAAGGTATAGATTTATTAGTATCACCATTGAATGAA
GTTTATAAAGGAGAGCCTACAATACCAGGTGATCCAAGTAGTAATTTAGA

Figure 11B

Predicted Dictyostelium (Dictyostelium discoideum) Smek1 cDNA sequence continued (SEQ ID NO 29)

TTCATTTGTACTCTATAATATAATGGAGTTGGTAATCTATTGTATTAAAC
ATCATTGCTATCGTATTAAACATTTTATAGTTGAAGAAGGTATTGCAAAA
AAGATATTAAGGTATACGAACCCTACAGGTAGTGGGGGTGGTGGTGGTGG
TGGTGGAAATAGTGAAAGATATTTAATACTTGGATCAATTAGATTTTTTA
GATCAATGGTAAATATGAAAGATGACCTATATAATCAACATATCATTCAA
GAGAATCTATTTGAACCAATCATTGAAGTTTTCAAATCAAACATTTCTAG
GTATAATCTATTAAATTCAGCAATCATAGAACTATTTCAATACATCTACA
AAGAGAACATTAGGGATTTAATTGTTTATTTAGTCGAAAGGTATAGAGAA
TTGTTTGAATCGGTAACCTATACCGACGTTTTAAAACAATTGATTTTAAA
GTATGAACAAATTAAGGATTCTTCATTTGAAAGTCCAGAAACATCTTGTA
ATAATAACGATAGCAGTAGCAATGATATTGATAGCAAACCTATCATTGGT
AATAATAAAATTAATCATAATTATCAAAGAACTCAAAGAGAAATCGATGA
GGAAGAAGAAGAAGCTTATTTTAATAGAGATGATGATTCTGAAGATTCTG
ATGATGAAGATGAATTAATTCCGATTTCAATTAATAATAATAATAATAAC
AATAATAATAATAAACAAATTTGTACAAATAATGAAAATAATATGGAGAA
AAATGATGATAATATAGAAAAGGATAATGAAAATACTAATAATGGAAATG
GTAGTAGTCATATAAAGATTGTAGATTATGAAGACGAAGATGATGAAGAT
GATGAAATTAATAAATCTGTAGAAAGTGATGATATTGTTGAAAAACATGA
AATAATAGATAAAAATGAAAAAAAGATGAAATAATGAAAGAAAATAATG
ATAGTGATAATGATGATAATGATAATAATGATAATGACAATGATAATGAT
AATAATAGCGATATAGAAAATAAAAATCATCTTAATAATAATGGTAATAA
TGAAAATAATGAAAATAATGACGATGTTCAAGATAAAAGTAACAACAAAA
ACAATAGTGATAAAATAAACGAAGATGAAAAAATAGAAAAACAAGATGAA
ATGAAAGAGAATTTAGAAATGGAAGAAATAGATGAAAAGTTAAAGAAAA
ACAACCCAAAGATATTAAAAAGAAAACCAATCACAGCCAGACGAAACTG
TTTTTAATGGTAAAAGTAATAATTCAAATAATAATAATAATAATAATAAT
AATAATAGCAATAATCAAGAGATTGGAGATAATAGGAAAACAACACCAAA
AAGAAAATTGGATTATGAAAAAATGAATCTGTTGTTTCAAAGAAAATTG
ATAAAAGTAATGGACCAACTTCAATAGACAAAGATATTAATGGTTGCGAT
GAATCACCAAATAAAAAATTAAATAATAATAATAGTAACAATAATAATAA

Figure 11C

Predicted Dictyostelium (Dictyostelium discoideum) Smek1 cDNA sequence continued (SEQ ID NO 29)

```
TAATAATAATAATAATAATAATAATAATAATAATAATAATAATAATAATA
ATAATAATAATAATAATAACAACAATCAAAATGATGAAAATGAATTA
TCAAGTGCATCAGAAGAAGAAGAAGAACAGTTAGAGAATGGAAAACATAT
AAAGAAATTCAAAAGAGGGAAAAAGATTCAAATAATTCCAGTAATAATT
CAAATAATAGTAGTCCAACTCCTAGTGAACTACATGTTTAAAT
```

Figure 12A

Cloned C. elegans (Caenorhabditis elegans) Smek1 cDNA sequence (SEQ ID NO 30)

ATGTCGGACACAAAAGAGGTATCTGATGATCCGATGGAGCTTGGAACGAG
TTCAACAGTTATCGCTAAGGAGGAAAATGACAAGGAAAGCCTGAAAAGAA
TGGAAGTAGACGATGAGAAGAACCTGAAGAAGAAATCGTTGAGAAAACT
GAAGAGAAACAGGAAGAAGAAGACGTGACAGTAAAGCTAGAAGATGAAAC
AGAAACTGAGGTGGAAAGTGTGGATGGTGGTCAAGAAGAAAAGAAGTTG
TTGATGAAAAACAGGTGGATGCAGAGCGAGTAAATACCAAAACAGAAGAG
TTATCACCGAAAAAGAAGTTAAAGCGGAGGAAGATCCTGAAACTGAAAC
AAAGAAGAAGGATCCTTCTGAGCAAACGAATGGTCAGGTCAAAAGAAAA
GTGATAAGCAGAGTCCAAAAAAGAAAGAGAAATCTGAGGGAAAAGAAAAT
AGTCCCGGCTCAAAGCTCACCAACAGAGATCATATTCTTGACCATCTTGA
TATAAAACGAGACGCAACCAACCGTGTGAAGCTTTACGTTCTCTGCGATC
AACGAATCTGGGAGGACCGAGGTACTGGTCATGTCGTCACTCATCAGTTA
TCAGCTGAAGATGGAGCTCCGTCGAATGCTGGAAATACAATGGTCCTCGT
CCGACTTGAGGGGCAAAATAAAAACATGCTCGAGTCACGGATTCAGATGG
ACACAGTCTACCAAAAACAACAGGAAACTCTAATTGTTTGGTCCGAAACC
GATGTGATGGATTTGGCATTATCATTCCAAGAAAGTCGGGATGCGAAGA
ATTATGGCAAAAAATCTGCGAAGTACAAGGGAGAGATCCTGGAGATCCTG
ATGCCACTTTCGATGACGGAGACGACAGTGATGTTGGAGAAATGCCATCA
TCTGCTAGTCGCCTACAACTTCCGCCAATTGAAATTGGGAGGCTGGGTGA
GCTTGATGCGCTTCTTCATATGCATCTTACGACAAACAGTGCCAGGGAAA
AAATGACTCTTGCTATAGAAAACGATAATGTCGTTACAAAACTTTGTGAA
GTTTTCCGGATGTGCGAAGATATTGAACATACAGAAGGACTACGAACTTT
TTATTCAATCGTGAAGAACCTGTTCATGCTCAACCGAAACACTGTTATCG
AAATGCTTCTCGACGATAATAATATCAAAGACGTAATAGGGATGTTTGAG
TTCGATCCGGCTTACAAACATCCAAGGAAGCACCGTGATTTTGTCTATAA
AAAGGCCAAATTTCGCGAGGTTTTGAACATTTCATGTGACGAACTTCGCG
ACAAGATTCATCGGCTCTACCGTGCTCAATACATTCAGGATGCGTGTCTT
CCCAGTTTGGGACTTTTCGAAGAAATCTTCTCTCCACACTTAGTAGTCA
TGTATTTTTCTGCCGTGTCGACATTGTAACGCTACTTCAAAAAGACAAAA
AAGCAATGTCTGAGCTTTTTGGGCAACTGATCAGTGAAGAAACAGATGTT

Figure 12B

Cloned C. elegans (Caenorhabditis elegans) Smek1 cDNA sequence continued (SEQ ID NO 30)

ATTCGTCGGCGAGATCTGGCACTTTTCCTAAAAGAGATGATTAGCCTAAG
TACCAGCATCCCATCAAACGGACCAGCCGCGACAAAGGAAACCTTTTCA
AATTACAGCTCCAGAACATGTTCAACTCTGAGATTTTGGATTCGCTGGAG
CCTTGTTTCAAATCACCTGATCATGAAACAAGAGCAGTAATGGTGGATGT
ACTTCGAACAATGGTCGATGCGAATGCTCAAATGATCCGTGACTTTCTGC
TCAAGCAATCCAAAACGAAAGACAAAAATGAGGATGTGCTGCTGAATATG
ATGATCAGACATTTGTTAACTGATATTGATGTTCATTTGACGTCTGGATC
AGAGATTGTTTTGATTATGAAAACTCTGCTAGATCCCGAAAATATGACAA
CAGTGAAATCAGAAAGAAGCGATTTCTTGCAGCTATTCTACAATCGTTGC
TACGAAAGTCTTCTAAAGCCAATTCTTGAGAATGTCAGCGGAGGAAATAT
CAAAAAGGATGATTACATGATTGCCAATCGTCAATCGGTTATTCTTCGAC
TTTTAACATTCTGCGTAGAACATCACTCATTTTCAATGCGACAACGATGT
GTATCAAATGATTTGATGAATAAGGTTCTTGTATTGCTCAAGTCGAAGCA
TTCATTCCTTGTCTTGTCTGCACTGAAGCTTCTTCAACGTGTGGTTACTG
TCAAAGATGATAAATACATTCGGTACATTGTGAAGGAGAAGGTTCTGGAC
CCAGTCATGGAATGTTTCCGTAAAAATGGCAACCGCTATAACATTATCAA
CTCTTCTGTCTTGCATTTGTTCGAGTTTGTGAGAAGCGAAGATGTTCGTC
CACTCATAAAATATGTTGTCGAAAATCATATGGAAGTCGTTGATTCTGTA
AACTATGTAAAAACATTCAAAGAGATCAAGATTCGATACGACCAACATCG
TGATCGTGAAGATACGATGAGCGTTCGTTCTGAGGACAACTCATTGGCAA
GTCCACGAAGTTTCCGCAAGGATCGTAATGAAGATCAATGGTTTGATGAG
GATGAAGACCTGGAAGTTGGAACAATGCTTGAATCAATCGAAAAGGACTC
AGTCGCAGTGTCTCCCAAAAAGAAGAGGCTGGACAGAGGAAGACTGGTA
TGGAGCCCATGTTTCCATCATTACTGAAGCGCAAAAATGCATTTGATGAC
GACGAAGCTCCAGTATTCGGTGGAGGATCTGCTACTGTTATTAATAATAC
CGAAAAGAAAATTGTTATAAAGGTTAACAGCGATCGTTCTCCGTCTCGTA
CACCGTCTCCTGCATCGTCGCCCCGAGCAAGTTCCTCACCAGGACCATCC
AGAGACGATGAAGTAACTTCATCTCAAAACAACAAAGAAAGCAGTCCGAC

Figure 12C

Cloned C. elegans (Caenorhabditis elegans) Smek1 cDNA sequence continued (SEQ ID NO 30)

TCCTACGGTCAAGTCGCTGGTCGATTACGACGAATCGGATGATTCTGATG
ATGATCCACCATCTCCTGACGCAGTTCCCTCATCTTCAACTGGAAGTCCT
GAAAAAGAAGGAGACTCCGCTGATGGAAAGAAGGAGATTCGCCAGAATA
TAACGATGTATCGTCAACTAGCAACGAAGAGAAGTTCGACTCACGAAACG
GAGCGCCAGTCACTAATGAAAACGGAGGAGTAGAAGCTGCGGCACCAACA
GTTGAAATCAGCCGTAAACGCACTAGTGACGGTATTGATCCTGATGCAAA
GAGAATTCGAACTGAAGAGACTGCACCAGCGGCAACTGCCACAGTTTCGC
AGGCCTAA

Figure 13A

S. cerevisiae (Saccharomyces cerevisiae) Smek1 cDNA sequence (SEQ ID NO 31)

ATGTCATTACCGGGTACACCTACTACATCTCCGACCCCGATGGATGAGGA
TACTGAACAAGCCGTTTCGGTTAATACTGAACCCAAAAGAGTAAAGGTTT
ACATTTTAGAGAACAACGAATGGAAAGACACAGGTACAGGGTTTTGTATA
GGGGAGGTGGACGAAGGTAAGTTCGCATATCTTGTTGTCTCAGATGAAGA
CTCCCCAACTGAAACTTTACTAAAATCCAAACTAGAAGGAAATATTGAAT
ATCAACGGCAGGAGGAAACGCTTATTGTTTGGAAGGATTTAGGGGGGAAA
GATATAGCCTTGAGTTTTGAAGAAAGTATGGGATGTGACACCTTATGTGA
ATTCATTGTTCACGTCCAAAGGAACATAGAGTCAAATATTTCTTTAGTCA
CCGTAAAATCCAGCGACAACGGACTCGGGTCTGTTCACGACATTATAACG
GGCCCTGTGACCTTGCCCTCCAACGACCAGCAACAGAATAGTCAAACTTT
ACTAGAAGCTCTAAAGATTTTGAATGAAAATACTTCTTTCGATTTTTTGA
AAAACGAAACCATTGAGTTTATCCTCCAGTCAAATTACATTGATACACTG
ATTTCTCATTTCCACAAAGCAGAAGAAGAAAAGATACCGAAGGATTTATT
TTTGCTAAGTAACATCATCAAAACTTTGATACTTTACAATAAAAGAGACA
TATTGGAGTCAATGGTGGAGGACGATAGGATTATGGGAATAGTTGGGATT
TTAGAATACGATACTGAATACCCTACATCAAAGGCAAATCATAGGAAATA
TTTAGGATCAAAAGGTCCCAATTTCAAAGAGGTTATTCCATTGGAAAATG
AGGACTTAAAAATAATAATGAAAAATGTTTTCGCTTACAGTTCTTAAAA
GACGTGGTATTAGTACGATTTTAGACGATCATAATTTCAACTTAATCTC
GGAAATTGTCATGGACCTGGAAACGTGTATAATCGACTTTCTTCAAGTAG
GGACGTTTTGGACAGACTAATAGAGCTTTATGATACCAAAACCCTTCCA
GAAAGCTCTTCAGAGAAGGAGAAGTTTGTACAAAAACGAAAGACGGGAT
TAGATTGTTGCAACAGTGTGTTCAAATGTCAATCAATTTAGATGCGGTTG
ACCGTTCTAAGTTCTATAAAACACTTGTTCGAAAGGGTCTATTCAAAGTT
TTAGATTATGCATTTCACATGGAGACGGATAGTAATGTTAGGATTTTAGC
TACGGATACTATCATTACTATAATCGAACACGATATCTTGTTAATTCACA
ACGTTCAGAATGAAGATTCTTTCAAACGGCAACATAAATCAGCGCCCGAT
GACAAGTCTTCCCATCGGAAATATCCGCAGGATTACAGCTCCAGTACTGA
TTCCAAGTTGTTATTGATACTTTCAACCATTCTTCTGTCCGACAGGAGTC
CCGGATTGCGAGAACAAGTTGTGCAAGCGCTAAATACTTTGCTTCACCCT

Figure 13B

Cloned C. elegans (Caenorhabditis elegans) Smek1 cDNA sequence continued (SEQ ID NO 31)

GAAGGATGTGTGGGTAATGGAGAAGGTTCATATGATCTTATGGGCAGATC
AAATTATGAAGCTAAGAACACATCTGAAGATTTCCCAAGTTTCAGTTATG
GTTTAAACTCGGATTCAATCAATTTAAATAACTATCACTATAGCAGCGAT
GAAATGAATAATCTAGAGCCAGAATCTGAATCTGAATTTCAAGTAATGGA
ATATTTTGCAAATTTCTATAATAAAATCGCACCCATACTGTTTGGTCCAT
TAATCAAGAAGGATATCACAACGGAAATGGCAGAAATAGATGGGCAAATA
GAAAAGGTTACAAAAGACGATCTTTTGTTAATTCATTTAGTGAAATTGGT
ATCATTTGTTTGCACTGAGCATGATCGTGTCTTATCCAGAAGATTCATAT
TAGAAAACGGTATACTAGATTCTGTTAGCAAACTTATCGGCGGTAATCAT
ATGATGCAGCTAAGGTTAACAGCAGTAAGATGCATTAAAAACCTTATGTG
TCTCGATGATAAATACTATCATCGATATATGATTTCAAAAAATTTATATG
CGCCGGTTTTTAAACTCTTCCAGGAGAACATAGATAAGAATAATCTTGCA
AATTCATGCATTCAAGATTTTTTCCGCATTATTATAACAGAATGTAGAGC
TTATCAAAGTGATGGCCATAACAGAAGGAAAAAACCAATGGTTCTTATG
ATGGCAACGGTAATGACGTCAAAACGAACGTGAACAACAATAGGACAAAC
TTTACCATTTTAAACAAATACTTAGTTCAAACATATGGTGATGTCTTGAG
AAAAGCTACTGATATCCCTTTCATCCAGGATATGCTAGAAACCGGGGAAG
AAAACCAACCCGATCATTCTAGCTTTGAAAATAGCATTGAAGGGGGGAAT
GACATTTCTGTAAATATGTCAACAGATGGATTTGCTTCGAATCATTTAGA
AGATATTGACATTAAAAACGTCAAAGATTACATTCTGAGATTGAACACT
TTGAAAATGACCCCATTATTCTGGTGATCAGTTAGCATTTAAAAAAGC
GTTGACCAAATGAATGCAAGTACTTGA

SEQUENCE LISTING

<160> NUMBER OF SEQ ID NOS: 31

<210> SEQ ID NO 1
<211> LENGTH: 820
<212> TYPE: PRT
<213> ORGANISM: Homo sapiens

<400> SEQUENCE: 1

```
Met Thr Asp Thr Arg Arg Val Lys Val Tyr Thr Leu Asn Glu Asp
 1               5                  10                  15

Arg Gln Trp Asp Asp Arg Gly Thr Gly His Val Ser Ser Gly Tyr Val
                20                  25                  30

Glu Arg Leu Lys Gly Met Ser Leu Leu Val Arg Ala Glu Ser Asp Gly
                35                  40                  45

Ser Leu Leu Leu Glu Ser Lys Ile Asn Pro Asn Thr Ala Tyr Gln Lys
            50                  55                  60

Gln Gln Asp Thr Leu Ile Val Trp Ser Glu Ala Glu Asn Tyr Asp Leu
65                  70                  75                  80

Ala Leu Ser Phe Gln Glu Lys Ala Gly Cys Asp Glu Ile Trp Glu Lys
                85                  90                  95

Ile Cys Gln Val Gln Gly Lys Asp Pro Ser Val Asp Ile Thr Gln Asp
                100                 105                 110

Leu Val Asp Glu Ser Glu Glu Glu Arg Phe Asp Asp Met Ser Ser Pro
                115                 120                 125

Gly Leu Glu Leu Pro Ser Cys Glu Leu Ser Arg Leu Glu Glu Ile Ala
            130                 135                 140

Glu Leu Val Ala Ser Ser Leu Pro Ser Pro Leu Arg Arg Glu Lys Leu
145                 150                 155                 160

Ala Leu Ala Leu Glu Asn Glu Gly Tyr Ile Lys Lys Leu Leu Glu Leu
                165                 170                 175

Phe His Val Cys Glu Asp Leu Glu Asn Ile Glu Gly Leu His His Leu
                180                 185                 190

Tyr Glu Ile Ile Lys Gly Ile Phe Leu Leu Asn Arg Thr Ala Leu Phe
                195                 200                 205

Glu Val Met Phe Ser Glu Glu Cys Ile Met Asp Val Ile Gly Cys Leu
                210                 215                 220

Glu Tyr Asp Pro Ala Leu Ser Gln Pro Arg Lys His Arg Glu Phe Leu
225                 230                 235                 240

Thr Lys Thr Ala Lys Phe Lys Glu Val Ile Pro Ile Ser Asp Pro Glu
                245                 250                 255

Leu Lys Gln Lys Ile His Gln Thr Tyr Arg Val Gln Tyr Ile Gln Asp
                260                 265                 270

Met Val Leu Pro Thr Pro Ser Val Phe Glu Glu Asn Met Leu Ser Thr
            275                 280                 285

Leu His Ser Phe Ile Phe Phe Asn Lys Val Glu Ile Val Gly Met Leu
            290                 295                 300

Gln Glu Asp Glu Lys Phe Leu Thr Asp Leu Phe Ala Gln Leu Thr Asp
305                 310                 315                 320

Glu Ala Thr Asp Glu Glu Lys Arg Gln Glu Leu Val Asn Phe Leu Lys
                325                 330                 335

Glu Phe Cys Ala Phe Ser Gln Thr Leu Gln Pro Gln Asn Arg Asp Ala
                340                 345                 350

Phe Phe Lys Thr Leu Ser Asn Met Gly Ile Leu Pro Ala Leu Glu Val
```

-continued

```
                355                 360                 365
Ile Leu Gly Met Asp Asp Thr Gln Val Arg Ser Ala Ala Thr Asp Ile
    370                 375                 380

Phe Ser Tyr Leu Val Glu Tyr Asn Pro Ser Met Val Arg Glu Phe Val
385                 390                 395                 400

Met Gln Glu Ala Gln Gln Asn Asp Asp Ile Leu Leu Ile Asn Leu
                405                 410                 415

Ile Ile Glu His Met Ile Cys Asp Thr Asp Pro Glu Leu Gly Gly Ala
                420                 425                 430

Val Gln Leu Met Gly Leu Leu Arg Thr Leu Val Asp Pro Glu Asn Met
                435                 440                 445

Leu Ala Thr Ala Asn Lys Thr Glu Lys Thr Glu Phe Leu Gly Phe Phe
450                 455                 460

Tyr Lys His Cys Met His Val Leu Thr Ala Pro Leu Leu Ala Asn Thr
465                 470                 475                 480

Thr Glu Asp Lys Pro Ser Lys Asp Phe Gln Thr Ala Gln Leu Leu
                485                 490                 495

Ala Leu Val Leu Glu Leu Leu Thr Phe Cys Val Glu His His Thr Tyr
                500                 505                 510

His Ile Lys Asn Tyr Ile Ile Asn Lys Asp Ile Leu Arg Arg Val Leu
                515                 520                 525

Val Leu Met Ala Ser Lys His Ala Phe Leu Ala Leu Cys Ala Leu Arg
                530                 535                 540

Phe Lys Arg Lys Ile Ile Gly Leu Lys Asp Glu Phe Tyr Asn Arg Tyr
545                 550                 555                 560

Ile Met Lys Ser Phe Leu Phe Glu Pro Val Val Lys Ala Phe Leu Asn
                565                 570                 575

Asn Gly Ser Arg Tyr Asn Leu Met Asn Ser Ala Ile Ile Glu Met Phe
                580                 585                 590

Glu Phe Ile Arg Val Glu Asp Ile Lys Ser Leu Thr Ala His Val Ile
                595                 600                 605

Glu Asn Tyr Trp Lys Ala Leu Glu Asp Val Asp Tyr Val Gln Thr Phe
610                 615                 620

Lys Gly Leu Lys Leu Arg Phe Glu Gln Gln Arg Glu Arg Gln Asp Asn
625                 630                 635                 640

Pro Lys Leu Asp Ser Met Arg Ser Ile Leu Arg Asn His Arg Tyr Arg
                645                 650                 655

Arg Asp Ala Arg Thr Leu Glu Asp Glu Glu Met Trp Phe Asn Thr
                660                 665                 670

Asp Glu Asp Asp Met Glu Asp Gly Glu Ala Val Val Ser Pro Ser Asp
                675                 680                 685

Lys Thr Lys Asn Asp Asp Asp Ile Met Asp Pro Ile Ser Lys Phe Met
690                 695                 700

Glu Arg Lys Lys Leu Lys Glu Ser Glu Lys Glu Val Leu Leu Lys
705                 710                 715                 720

Thr Asn Leu Ser Gly Arg Gln Ser Pro Ser Phe Lys Leu Ser Leu Ser
                725                 730                 735

Ser Gly Thr Lys Thr Asn Leu Thr Ser Gln Ser Ser Thr Asn Leu
                740                 745                 750

Pro Gly Ser Pro Gly Ser Pro Gly Ser Pro Gly Ser Pro Gly Ser Pro
                755                 760                 765

Gly Ser Val Pro Lys Asn Thr Ser Gln Thr Ala Ala Ile Thr Thr Lys
770                 775                 780
```

```
Gly Gly Leu Val Gly Leu Val Asp Tyr Pro Asp Asp Glu Asp
785                 790                 795                 800

Asp Glu Asp Glu Asp Lys Glu Asp Thr Leu Pro Leu Ser Lys Lys Ala
                805                 810                 815

Lys Phe Asp Ser
            820

<210> SEQ ID NO 2
<211> LENGTH: 817
<212> TYPE: PRT
<213> ORGANISM: Homo sapiens

<400> SEQUENCE: 2

Met Ser Asp Thr Arg Arg Val Lys Val Tyr Thr Leu Asn Glu Asp
 1               5                  10                  15

Arg Gln Trp Asp Asp Arg Gly Thr Gly His Val Ser Ser Thr Tyr Val
                20                  25                  30

Glu Glu Leu Lys Gly Met Ser Leu Leu Val Arg Ala Glu Ser Asp Gly
             35                  40                  45

Ser Leu Leu Leu Glu Ser Lys Ile Asn Pro Asn Thr Ala Tyr Gln Lys
         50                  55                  60

Gln Gln Asp Thr Leu Ile Val Trp Ser Glu Ala Glu Asn Tyr Asp Leu
65                  70                  75                  80

Ala Leu Ser Phe Gln Glu Lys Ala Gly Cys Asp Glu Ile Trp Glu Lys
                85                  90                  95

Ile Cys Gln Val Gln Gly Lys Asp Pro Ser Val Glu Val Thr Gln Asp
                100                 105                 110

Leu Ile Asp Glu Ser Glu Glu Arg Phe Glu Met Pro Glu Thr
            115                 120                 125

Ser His Leu Ile Asp Leu Pro Thr Cys Glu Leu Asn Lys Leu Glu Glu
130                 135                 140

Ile Ala Asp Leu Val Thr Ser Val Leu Ser Ser Pro Ile Arg Arg Glu
145                 150                 155                 160

Lys Leu Ala Leu Ala Leu Glu Asn Glu Gly Tyr Ile Lys Lys Leu Leu
                165                 170                 175

Gln Leu Phe Gln Ala Cys Glu Asn Leu Glu Asn Thr Glu Gly Leu His
            180                 185                 190

His Leu Tyr Glu Ile Ile Arg Gly Ile Leu Phe Leu Asn Lys Ala Thr
        195                 200                 205

Leu Phe Glu Val Met Phe Ser Asp Glu Cys Ile Met Asp Val Val Gly
210                 215                 220

Cys Leu Glu Tyr Asp Pro Ala Leu Ala Gln Pro Lys Arg His Arg Glu
225                 230                 235                 240

Phe Leu Thr Lys Thr Ala Lys Phe Lys Glu Val Ile Pro Ile Thr Asp
                245                 250                 255

Ser Glu Leu Arg Gln Lys Ile His Gln Thr Tyr Arg Val Gln Tyr Ile
            260                 265                 270

Gln Asp Ile Ile Leu Pro Thr Pro Ser Val Phe Glu Glu Asn Phe Leu
        275                 280                 285

Ser Thr Leu Thr Ser Phe Ile Phe Phe Asn Lys Val Glu Ile Val Ser
    290                 295                 300

Met Leu Gln Glu Asp Glu Lys Phe Leu Ser Glu Val Phe Ala Gln Leu
305                 310                 315                 320

Thr Asp Glu Ala Thr Asp Asp Asp Lys Arg Arg Glu Leu Val Asn Phe
```

-continued

```
                325                 330                 335
Phe Lys Glu Phe Cys Ala Phe Ser Gln Thr Leu Gln Pro Gln Asn Arg
            340                 345                 350

Asp Ala Phe Phe Lys Thr Leu Ala Lys Leu Gly Ile Leu Pro Ala Leu
            355                 360                 365

Glu Ile Val Met Gly Met Asp Asp Leu Gln Val Arg Ser Ala Ala Thr
370                 375                 380

Asp Ile Phe Ser Tyr Leu Val Glu Phe Ser Pro Ser Met Val Arg Glu
385                 390                 395                 400

Phe Val Met Gln Glu Ala Gln Gln Ser Asp Asp Ile Leu Leu Ile
                405                 410                 415

Asn Val Val Ile Glu Gln Met Ile Cys Asp Thr Asp Pro Glu Leu Gly
            420                 425                 430

Gly Ala Val Gln Leu Met Gly Leu Leu Arg Thr Leu Ile Asp Pro Glu
            435                 440                 445

Asn Met Leu Ala Thr Thr Asn Lys Thr Glu Lys Ser Glu Phe Leu Asn
450                 455                 460

Phe Phe Tyr Asn His Cys Met His Val Leu Thr Ala Pro Leu Leu Thr
465                 470                 475                 480

Asn Thr Ser Glu Asp Lys Cys Glu Lys Asp Asn Ile Val Gly Ser Asn
            485                 490                 495

Lys Asn Asn Thr Ile Cys Pro Asp Asn Tyr Gln Thr Ala Gln Leu Leu
            500                 505                 510

Ala Leu Ile Leu Glu Leu Leu Thr Phe Cys Val Glu His His Thr Tyr
            515                 520                 525

His Ile Lys Asn Tyr Ile Met Asn Lys Asp Leu Leu Arg Arg Val Leu
            530                 535                 540

Val Leu Met Asn Ser Lys His Thr Phe Leu Ala Leu Cys Ala Leu Arg
545                 550                 555                 560

Phe Met Arg Arg Ile Ile Gly Leu Lys Asp Glu Phe Tyr Asn Arg Tyr
                565                 570                 575

Ile Thr Lys Gly Asn Leu Phe Glu Pro Val Ile Asn Ala Leu Leu Asp
            580                 585                 590

Asn Gly Thr Arg Tyr Asn Leu Leu Asn Ser Ala Val Ile Glu Leu Phe
            595                 600                 605

Glu Phe Ile Arg Val Glu Asp Ile Lys Ser Leu Thr Ala His Ile Val
            610                 615                 620

Glu Asn Phe Tyr Lys Ala Leu Glu Ser Ile Glu Tyr Val Gln Thr Phe
625                 630                 635                 640

Lys Gly Leu Lys Thr Lys Tyr Glu Gln Glu Lys Asp Arg Gln Asn Gln
                645                 650                 655

Lys Leu Asn Ser Val Pro Ser Ile Leu Arg Ser Asn Arg Phe Arg Arg
            660                 665                 670

Asp Ala Lys Ala Leu Glu Glu Asp Glu Met Trp Phe Asn Glu Asp
            675                 680                 685

Glu Glu Glu Glu Gly Lys Ala Val Val Ala Pro Val Glu Lys Pro Lys
690                 695                 700

Pro Glu Asp Asp Phe Pro Asp Asn Tyr Glu Lys Phe Met Glu Thr Lys
705                 710                 715                 720

Lys Ala Lys Glu Ser Glu Asp Lys Glu Asn Leu Pro Lys Arg Thr Ser
                725                 730                 735

Pro Gly Gly Phe Lys Phe Thr Phe Ser His Ser Ala Ser Ala Ala Asn
            740                 745                 750
```

-continued

Gly Thr Asn Ser Lys Ser Val Ala Gln Ile Pro Ala Thr Ser
            755                 760             765

Asn Gly Ser Ser Lys Thr Thr Asn Leu Pro Thr Ser Val Thr Ala
        770             775                 780

Thr Lys Gly Ser Leu Val Gly Leu Val Asp Tyr Pro Asp Glu Glu
785                 790             795                 800

Glu Asp Glu Glu Glu Ser Ser Pro Arg Lys Arg Pro Arg Leu Gly
                805             810             815

Ser

<210> SEQ ID NO 3
<211> LENGTH: 836
<212> TYPE: PRT
<213> ORGANISM: Drosophila melanogaster

<400> SEQUENCE: 3

Met Thr Thr Asp Thr Arg Arg Val Lys Leu Tyr Ala Leu Asn Ala
1               5                   10                  15

Glu Arg Gln Trp Asp Asp Arg Gly Thr Gly His Val Ser Ser Thr Tyr
                20                  25                  30

Val Glu Arg Leu Lys Gly Ile Ser Leu Leu Val Arg Ala Glu Ser Asp
            35                  40                  45

Gly Ser Leu Leu Leu Glu Ser Lys Ile Gln Pro Asp Thr Ala Tyr Gln
        50                  55                  60

Lys Gln Gln Asp Thr Leu Ile Val Trp Ser Gly Asp Asn Phe Asp
65                  70                  75                  80

Leu Ala Leu Ser Phe Gln Glu Lys Ala Gly Cys Asp Glu Ile Trp Glu
                85                  90                  95

Lys Ile Cys Gln Val Gln Gly Lys Asp Pro Ser Val Glu Ile Thr Gln
            100                 105                 110

Asp Ile Val Glu Glu Ser Glu Asp Glu Arg Phe Glu Asp Ile Cys Leu
        115                 120                 125

Ser Thr Pro Leu Arg Lys Glu Lys Leu Ser Met Ala Leu Glu Ser Glu
130                 135                 140

Ser Tyr Ile Lys Lys Leu Leu Asn Leu Phe His Val Cys Glu Asp Leu
145                 150                 155                 160

Asp Asn Thr Glu Gly Leu His His Leu Phe Glu Ile Phe Lys Asn Ile
                165                 170                 175

Phe Leu Leu Asn Lys Asn Ala Leu Phe Glu Ile Met Phe Ala Asp Asp
            180                 185                 190

Thr Ile Phe Asp Val Val Gly Cys Leu Glu Tyr Asp Pro Ser Val Ser
        195                 200                 205

Gln Pro Lys Lys His Arg Gln Tyr Leu Lys Gln Leu Ala Lys Phe Arg
210                 215                 220

Glu Ala Val Pro Ile Lys Asn Leu Asp Leu Leu Ala Lys Ile His Gln
225                 230                 235                 240

Thr Phe Arg Val Gln Tyr Ile Gln Asp Ile Ile Leu Pro Thr Pro Ser
                245                 250                 255

Val Phe Val Glu Asp Asn Met Leu Asn Thr Leu Ser Ser Phe Ile Phe
            260                 265                 270

Phe Asn Lys Val Glu Ile Val Thr Met Ile Gln Asp Asp Glu Arg Tyr
        275                 280                 285

Leu Leu Asp Val Phe Ala Val Leu Thr Asp Pro Thr Thr Gly Asp Ala
290                 295                 300

```
Lys Arg Arg Asp Thr Val Leu Phe Leu Lys Glu Phe Cys Asn Tyr Ala
305                 310                 315                 320

Gln Asn Leu Gln Pro Gln Gly Lys Asp Ser Phe Tyr Lys Thr Leu Thr
                325                 330                 335

Cys Leu Gly Ile Leu Gln Ala Leu Glu Leu Thr Leu Val Met Asn Asp
                340                 345                 350

Lys Lys Thr Lys Ser Ala Ser Ile Asp Ile Leu Thr Ala Ile Val Glu
                355                 360                 365

Phe Ser Pro Leu Val Val Arg Asn Tyr Thr Leu Asn Gln Ala Asn Arg
370                 375                 380

Pro Glu Val Glu Arg Met Leu Leu Asn Ile Ala Ile Glu Gln Met Leu
385                 390                 395                 400

Asn Asp Ser Glu Pro Glu Leu Gly Ile Ala Val Gln Leu Met Gly Ile
                405                 410                 415

Val Lys Ile Leu Leu Glu Pro Glu Asn Met Leu Thr Glu Lys Gly Asp
                420                 425                 430

Phe Leu Asn Phe Phe Tyr Lys Tyr Ser Val Gln Thr Leu Val Ala Pro
                435                 440                 445

Val Ile Leu Asn Thr Ile Gly Asp Arg Pro Gln Asn Glu Asp Tyr Gln
                450                 455                 460

Thr Ala Gln Leu Leu Gly Ile Val Leu Asp Ile Leu Ser Phe Cys Val
465                 470                 475                 480

Glu His His Ser Tyr His Ile Lys Asn Phe Leu Leu Gln Lys Asp Leu
                485                 490                 495

Leu Lys Arg Ile Leu Val Leu Met Lys Ser Thr His Thr Phe Leu Val
                500                 505                 510

Leu Gly Ala Leu Arg Leu Leu Arg Lys Ile Ile Ala Leu Lys Asp Glu
                515                 520                 525

Phe Tyr Asn Arg His Ile Val Lys Cys Asn Leu Phe Ala Pro Val Val
                530                 535                 540

Asp Ala Phe Ile Arg Asn Asn Gly Arg Tyr Asn Leu Leu Glu Ser Ala
545                 550                 555                 560

Ile Leu Glu Leu Phe Glu Phe Ile Lys Leu Glu Asp Ile Arg Thr Leu
                565                 570                 575

Cys Val Tyr Phe Val Glu Asn Phe Ser Lys Ile Phe Asp Glu Ile Glu
                580                 585                 590

Tyr Val Gln Thr Phe Lys Tyr Leu Lys Asn Arg Tyr Asp Gln Tyr Gln
                595                 600                 605

Asp Arg Leu Lys Asp Arg Asp Lys Met Glu Asn Arg Thr Asp Gly Gly
610                 615                 620

Leu Pro Ile Ile Arg Ser Gly Gly Arg Phe Arg Arg Asp Gln Arg Gln
625                 630                 635                 640

Met Glu Glu Glu Glu Met Trp Phe Asn Glu Glu Asp Asp Phe Thr
                645                 650                 655

Glu Glu Ile Asp Thr Tyr Asn Asn Val Met Lys Ser Val Ser Glu Lys
                660                 665                 670

Asn Gly Pro Gln Thr Gln Asn Gln Gln Lys Ser Ser Pro Pro His Ser
                675                 680                 685

Thr Ser Pro His Ser Gly Leu Leu Gly Ser Leu Thr Phe Gln Gln
                690                 695                 700

Gln Thr Gln Pro Glu Ile Ala Glu Leu Gln Gln Leu Ser Ser Val
705                 710                 715                 720
```

```
Glu Ala Pro Gln Ser Gln Ser Gln Phe Leu Ser Thr Ile Ala Thr Ala
                725                 730                 735

Met Ala Ala Ser Val Thr Ala Ala Ala Thr Asn Ser Ser Pro Ser
            740                 745                 750

Ile Ser Pro Ala Pro Ala Val Ser Ser Pro Asp Ile Glu Asn Ala Asp
            755                 760                 765

Ala Gln Leu Pro Pro Ser Asp Asp Ala Ser Ser Pro Ala Ser Gly Glu
        770                 775                 780

Gln Asp Ala Asn Ser Thr Glu Gly Thr Ser Ser Glu Ala Asp Lys Thr
785                 790                 795                 800

Thr Ala Lys Lys Gly Leu Val Asp Tyr Glu Ser Asp Ser Gly Glu Asp
                805                 810                 815

Asp Tyr Glu Glu Asp Glu Tyr Ser Glu Gly Pro Gln Ala Gln Lys Arg
                820                 825                 830

Ala Arg Gln Ala
        835

<210> SEQ ID NO 4
<211> LENGTH: 863
<212> TYPE: PRT
<213> ORGANISM: Caenorhabditis elegans

<400> SEQUENCE: 4

Met Lys Arg Asp Ala Thr Asn Arg Val Lys Leu Tyr Val Leu Cys Asp
1               5                   10                  15

Gln Arg Ile Trp Glu Asp Arg Gly Thr Gly His Val Val Thr His Gln
            20                  25                  30

Leu Ser Ala Glu Asp Gly Ala Pro Ser Asn Ala Gly Asn Thr Met Val
        35                  40                  45

Leu Val Arg Leu Glu Gly Gln Asn Lys Asn Met Leu Glu Ser Arg Ile
    50                  55                  60

Gln Met Asp Thr Val Tyr Gln Lys Gln Glu Thr Leu Ile Val Trp
65                  70                  75                  80

Ser Glu Thr Asp Val Met Asp Leu Ala Leu Ser Phe Gln Glu Lys Ser
                85                  90                  95

Gly Cys Glu Glu Leu Trp Gln Lys Ile Cys Glu Val Gln Gly Arg Asp
            100                 105                 110

Pro Gly Asp Pro Asp Ala Thr Phe Asp Asp Gly Asp Asp Ser Asp Val
        115                 120                 125

Gly Glu Met Pro Ser Ser Ala Ser Arg Leu Gln Leu Pro Pro Ile Glu
    130                 135                 140

Ile Gly Arg Leu Gly Glu Leu Asp Ala Leu Leu His Met His Leu Thr
145                 150                 155                 160

Thr Asn Ser Ala Arg Glu Lys Met Thr Leu Ala Ile Glu Asn Asp Asn
                165                 170                 175

Val Val Thr Lys Leu Cys Glu Val Phe Arg Met Cys Glu Asp Ile Glu
            180                 185                 190

His Thr Glu Gly Leu Arg Thr Phe Tyr Ser Ile Val Lys Asn Leu Phe
        195                 200                 205

Met Leu Asn Arg Asn Thr Val Ile Glu Met Leu Leu Asp Asp Asn Asn
    210                 215                 220

Ile Lys Asp Val Ile Gly Met Phe Glu Phe Asp Pro Ala Tyr Lys His
225                 230                 235                 240

Pro Arg Lys His Arg Asp Phe Val Tyr Lys Lys Ala Lys Phe Arg Glu
                245                 250                 255
```

```
Val Leu Asn Ile Ser Cys Asp Glu Leu Arg Asp Lys Ile His Arg Leu
            260                 265                 270

Tyr Arg Ala Gln Tyr Ile Gln Asp Ala Cys Leu Pro Ser Leu Gly Leu
        275                 280                 285

Phe Glu Glu Asn Leu Leu Ser Thr Leu Ser Ser His Val Phe Phe Cys
        290                 295                 300

Arg Val Asp Ile Val Thr Leu Leu Gln Lys Asp Lys Lys Ala Met Ser
305                 310                 315                 320

Glu Leu Phe Gly Gln Leu Ile Ser Glu Thr Asp Val Ile Arg Arg
                325                 330                 335

Arg Asp Leu Ala Leu Phe Leu Lys Glu Met Ile Ser Leu Ser Thr Ser
            340                 345                 350

Ile Pro Ser Asn Gly Pro Ala Ala Thr Lys Glu Thr Phe Phe Lys Val
            355                 360                 365

Leu Gln Asn Met Phe Asn Ser Glu Ile Leu Asp Ser Leu Glu Pro Cys
        370                 375                 380

Phe Lys Ser Pro Asp His Glu Thr Arg Ala Val Met Val Asp Val Leu
385                 390                 395                 400

Arg Thr Met Val Asp Ala Asn Ala Gln Met Ile Arg Asp Phe Leu Leu
                405                 410                 415

Lys Gln Ser Lys Thr Lys Asp Lys Asn Glu Asp Val Leu Leu Asn Met
            420                 425                 430

Met Ile Arg His Leu Leu Thr Asp Ile Asp Val His Leu Thr Ser Gly
        435                 440                 445

Ser Glu Ile Val Leu Ile Met Lys Thr Leu Leu Asp Pro Glu Asn Met
        450                 455                 460

Thr Thr Val Lys Ser Glu Arg Ser Asp Phe Leu Gln Leu Phe Tyr Asn
465                 470                 475                 480

Arg Cys Tyr Glu Ser Leu Leu Lys Pro Ile Leu Glu Asn Val Ser Gly
                485                 490                 495

Gly Asn Ile Lys Lys Asp Asp Tyr Met Ile Ala Asn Arg Gln Ser Val
            500                 505                 510

Ile Leu Arg Leu Leu Thr Phe Cys Val Glu His His Ser Phe Ser Met
        515                 520                 525

Arg Gln Arg Cys Val Ser Asn Asp Leu Met Asn Lys Val Leu Val Leu
        530                 535                 540

Leu Lys Ser Lys His Ser Phe Leu Val Leu Ser Ala Leu Lys Leu Leu
545                 550                 555                 560

Gln Arg Val Val Thr Val Lys Asp Asp Lys Tyr Ile Arg Tyr Ile Val
                565                 570                 575

Lys Glu Lys Val Leu Asp Pro Val Met Glu Cys Phe Arg Lys Asn Gly
            580                 585                 590

Asn Arg Tyr Asn Ile Ile Asn Ser Ser Val Leu His Leu Phe Glu Phe
        595                 600                 605

Val Arg Ser Glu Asp Val Arg Pro Leu Ile Lys Tyr Val Val Glu Asn
        610                 615                 620

His Met Glu Val Val Asp Ser Val Asn Tyr Val Lys Thr Phe Lys Glu
625                 630                 635                 640

Ile Lys Ile Arg Tyr Asp Gln His Arg Asp Arg Glu Glu Thr Met Ser
                645                 650                 655

Val Arg Ser Glu Asp Asn Ser Leu Ala Ser Pro Arg Ser Phe Arg Lys
            660                 665                 670
```

-continued

Asp Arg Asn Glu Asp Gln Trp Phe Asp Glu Asp Leu Glu Val
        675                 680                 685

Gly Thr Met Leu Glu Ser Ile Glu Lys Asp Ser Val Ala Val Ser Pro
690                 695                 700

Lys Lys Glu Glu Ala Gly Gln Arg Lys Thr Gly Met Glu Pro Met Phe
705                 710                 715                 720

Pro Ser Leu Leu Lys Arg Lys Asn Ala Phe Asp Asp Glu Ala Pro
                725                 730                 735

Val Phe Gly Gly Gly Ser Ala Ala Val Ile Asn Asn Thr Glu Lys Lys
                740                 745                 750

Ile Val Ile Lys Val Asn Ser Asp Arg Ser Pro Ser Arg Thr Pro Ser
        755                 760                 765

Pro Ala Ser Ser Pro Arg Ala Ser Ser Ser Pro Gly Pro Ser Arg Asp
770                 775                 780

Asp Glu Val Thr Ser Ser Gln Asn Asn Lys Glu Ser Ser Pro Thr Pro
785                 790                 795                 800

Thr Val Lys Ser Leu Val Asp Tyr Asp Glu Ser Asp Asp Ser Asp Asp
                805                 810                 815

Asp Pro Pro Ser Pro Asp Ala Val Pro Ser Ser Thr Gly Ser Pro
        820                 825                 830

Glu Lys Glu Gly Asp Ser Ala Asp Gly Lys Lys Gly Asp Ser Pro Glu
        835                 840                 845

Tyr Asn Asp Val Ser Ser Thr Ser Asn Glu Glu Lys Phe Asp Ser
850                 855                 860

<210> SEQ ID NO 5
<211> LENGTH: 858
<212> TYPE: PRT
<213> ORGANISM: Saccharomyces cerevisiae

<400> SEQUENCE: 5

Met Ser Leu Pro Gly Thr Pro Thr Thr Ser Pro Thr Pro Met Asp Glu
1               5                   10                  15

Asp Thr Glu Gln Ala Val Ser Val Asn Thr Glu Pro Lys Arg Val Lys
            20                  25                  30

Val Tyr Ile Leu Glu Asn Asn Glu Trp Lys Asp Thr Gly Thr Gly Phe
        35                  40                  45

Cys Ile Gly Glu Val Asp Glu Gly Lys Phe Ala Tyr Leu Val Val Ser
    50                  55                  60

Asp Glu Asp Ser Pro Thr Glu Thr Leu Leu Lys Ser Lys Leu Glu Gly
65                  70                  75                  80

Asn Ile Glu Tyr Gln Arg Gln Glu Glu Thr Leu Ile Val Trp Lys Asp
                85                  90                  95

Leu Gly Gly Lys Asp Ile Ala Leu Ser Phe Glu Glu Ser Met Gly Cys
            100                 105                 110

Asp Thr Leu Cys Glu Phe Ile Val His Val Gln Arg Asn Ile Glu Ser
        115                 120                 125

Asn Ile Ser Leu Val Thr Val Lys Ser Ser Asp Asn Gly Leu Gly Ser
    130                 135                 140

Val His Asp Ile Ile Thr Gly Pro Val Thr Leu Pro Ser Asn Asp Gln
145                 150                 155                 160

Gln Gln Asn Ser Gln Thr Leu Leu Glu Ala Leu Lys Ile Leu Asn Glu
                165                 170                 175

Asn Thr Ser Phe Asp Phe Leu Lys Asn Glu Thr Ile Glu Phe Ile Leu
            180                 185                 190

```
Gln Ser Asn Tyr Ile Asp Thr Leu Ile Ser His Phe His Lys Ala Glu
    195                 200                 205
Glu Glu Lys Ile Pro Lys Asp Leu Phe Leu Ser Asn Ile Ile Lys
210                 215                 220
Thr Leu Ile Leu Tyr Asn Lys Arg Asp Ile Leu Glu Ser Met Val Glu
225                 230                 235                 240
Asp Asp Arg Ile Met Gly Ile Val Gly Ile Leu Glu Tyr Asp Thr Glu
                245                 250                 255
Tyr Pro Thr Ser Lys Ala Asn His Arg Lys Tyr Leu Gly Ser Lys Gly
            260                 265                 270
Pro Asn Phe Lys Glu Val Ile Pro Leu Glu Asn Glu Asp Leu Lys Ile
        275                 280                 285
Ile Met Lys Lys Cys Phe Arg Leu Gln Phe Leu Lys Asp Val Val Leu
    290                 295                 300
Val Arg Phe Leu Asp Asp His Asn Phe Asn Leu Ile Ser Glu Ile Val
305                 310                 315                 320
Met Asp Leu Glu Thr Cys Ile Ile Asp Phe Leu Gln Val Gly Thr Phe
                325                 330                 335
Leu Asp Arg Leu Ile Glu Leu Tyr Asp Thr Lys Thr Leu Pro Glu Ser
            340                 345                 350
Ser Ser Glu Lys Glu Lys Phe Val Gln Lys Arg Lys Asp Gly Ile Arg
        355                 360                 365
Leu Leu Gln Gln Cys Val Gln Met Ser Ile Asn Leu Asp Ala Val Asp
    370                 375                 380
Arg Ser Lys Phe Tyr Lys Thr Leu Val Arg Lys Gly Leu Phe Lys Val
385                 390                 395                 400
Leu Asp Tyr Ala Phe His Met Glu Thr Asp Ser Asn Val Arg Ile Leu
                405                 410                 415
Ala Thr Asp Thr Ile Ile Thr Ile Ile Glu His Asp Ile Leu Leu Ile
            420                 425                 430
His Asn Val Gln Asn Glu Asp Ser Phe Lys Arg Gln His Lys Ser Ala
        435                 440                 445
Pro Asp Asp Lys Ser Ser His Arg Lys Tyr Pro Gln Asp Tyr Ser Ser
    450                 455                 460
Ser Thr Asp Ser Lys Leu Leu Ile Leu Ser Thr Ile Leu Leu Ser
465                 470                 475                 480
Asp Arg Ser Pro Gly Leu Arg Glu Gln Val Val Gln Ala Leu Asn Thr
                485                 490                 495
Leu Leu His Pro Glu Gly Cys Val Gly Asn Gly Glu Gly Ser Tyr Asp
            500                 505                 510
Leu Met Gly Arg Ser Asn Tyr Glu Ala Lys Asn Thr Ser Glu Asp Phe
        515                 520                 525
Pro Ser Phe Ser Tyr Gly Leu Asn Ser Asp Ser Ile Asn Leu Asn Asn
    530                 535                 540
Tyr His Tyr Ser Ser Asp Glu Met Asn Asn Leu Glu Pro Glu Ser Glu
545                 550                 555                 560
Ser Glu Phe Gln Val Met Glu Tyr Phe Ala Asn Phe Tyr Asn Lys Ile
                565                 570                 575
Ala Pro Ile Leu Phe Gly Pro Leu Ile Lys Lys Asp Ile Thr Thr Glu
            580                 585                 590
Met Ala Glu Ile Asp Gly Gln Ile Glu Lys Val Thr Lys Asp Asp Leu
        595                 600                 605
```

```
Leu Leu Ile His Leu Val Lys Leu Val Ser Phe Val Cys Thr Glu His
    610                 615                 620

Asp Arg Val Leu Ser Arg Phe Ile Leu Glu Asn Gly Ile Leu Asp
625                 630                 635                 640

Ser Val Ser Lys Leu Ile Gly Gly Asn His Met Met Gln Leu Arg Leu
                645                 650                 655

Thr Ala Val Arg Cys Ile Lys Asn Leu Met Cys Leu Asp Asp Lys Tyr
                660                 665                 670

Tyr His Arg Tyr Met Ile Ser Lys Asn Leu Tyr Ala Pro Val Phe Lys
            675                 680                 685

Leu Phe Gln Glu Asn Ile Asp Lys Asn Leu Ala Asn Ser Cys Ile
690                 695                 700

Gln Asp Phe Phe Arg Ile Ile Ile Thr Glu Cys Arg Ala Tyr Gln Ser
705                 710                 715                 720

Asp Gly His Asn Arg Lys Glu Lys Thr Asn Gly Ser Tyr Asp Gly Asn
                725                 730                 735

Gly Asn Asp Val Lys Thr Asn Val Asn Asn Arg Thr Asn Phe Thr
                740                 745                 750

Ile Leu Asn Lys Tyr Leu Val Gln Thr Tyr Gly Asp Val Leu Arg Lys
            755                 760                 765

Ala Thr Asp Ile Pro Phe Ile Gln Asp Met Leu Glu Thr Gly Glu Glu
770                 775                 780

Asn Gln Pro Asp His Ser Ser Phe Glu Asn Ser Ile Glu Gly Gly Asn
785                 790                 795                 800

Asp Ile Ser Val Asn Met Ser Thr Asp Gly Phe Ala Ser Asn His Leu
                805                 810                 815

Glu Asp Ile Asp Ile Lys Asn Val Lys Arg Leu His Ser Glu Ile Glu
            820                 825                 830

His Phe Glu Asn Asp Pro His Tyr Ser Gly Asp Gln Leu Ala Phe Lys
835                 840                 845

Lys Ser Val Asp Gln Met Asn Ala Ser Thr
850                 855

<210> SEQ ID NO 6
<211> LENGTH: 1046
<212> TYPE: PRT
<213> ORGANISM: Dictyostelium discoideum

<400> SEQUENCE: 6

Met Glu Pro Leu Arg Lys Arg Val Lys Val Tyr Gln Leu Asp Asn Ser
1               5                   10                  15

Gly Lys Trp Asp Asp Lys Gly Thr Gly His Val Ser Cys Ile Tyr Val
                20                  25                  30

Asp Ala Leu Cys Ala Met Gly Leu Ile Val Arg Ser Glu Ser Asp Asn
            35                  40                  45

Ser Val Ile Leu Gln Thr Arg Leu Ser Ala Glu Asp Ile Tyr Gln Lys
    50                  55                  60

Gln Gln Asp Ser Leu Ile Val Trp Thr Glu Pro Asp Ser Gln Leu Asp
65                  70                  75                  80

Leu Ala Leu Ser Phe Gln Asp Ser Leu Gly Cys Gln Asp Ile Trp Glu
                85                  90                  95

Asn Ile Leu Gln Tyr Gln Asn Gln Arg Thr Gly Ser Cys Asp Ser Val
            100                 105                 110

Asp Leu Asp Leu Pro Pro Val Ser Ile Asn Asn Leu Gln Thr Ile Asn
    115                 120                 125
```

-continued

Glu Leu Leu Glu Ala Ser Leu Pro Met Leu Asp Lys Asp Lys Ile Ile
    130                 135                 140

Asn Ser Ile Phe Lys Glu Asp Leu Val Arg Ser Leu Asp Leu Phe
145                 150                 155                 160

Asp Glu Ile Glu Lys Ser Gly Glu Gly Gly Val His Leu Phe Gln Ile
            165                 170                 175

Phe Asn Ile Phe Lys Asn Leu Ile Leu Phe Asn Asp Thr Ser Ile Leu
            180                 185                 190

Glu Val Ile Leu Ser Glu Asp Tyr Leu Val Arg Val Met Gly Ala Leu
            195                 200                 205

Glu Tyr Asp Pro Glu Ile Ser Glu Asn Asn Arg Ile Lys His Arg Glu
    210                 215                 220

Phe Leu Asn Gln Gln Val Val Phe Lys Gln Val Ile Lys Phe Pro Ser
225                 230                 235                 240

Lys Ser Leu Ile Gly Thr Ile His Gln Thr Phe Arg Ile Gln Tyr Leu
            245                 250                 255

Lys Asp Val Val Leu Pro Arg Val Leu Asp Asp Val Thr Phe Ser Ser
            260                 265                 270

Leu Asn Ser Leu Ile Tyr Phe Asn Asn Ile Asp Ile Val Ser Gln Ile
        275                 280                 285

Gln Asn Asp Ser Asp Phe Leu Glu Asn Leu Phe Ser Glu Ile Gln Lys
    290                 295                 300

Ser Glu Lys Asn Ser Glu Glu Arg Lys Asp Leu Ile Leu Phe Leu Gln
305                 310                 315                 320

Asp Leu Cys Asn Leu Ala Lys Gly Leu Gln Ile Gln Ser Lys Ser Thr
            325                 330                 335

Phe Phe Thr Val Val Ser Leu Gly Leu Phe Lys Thr Leu Ser Ala
            340                 345                 350

Ile Leu Asp Asp Glu Asn Val Gln Thr Arg Val Ser Cys Thr Glu Ile
        355                 360                 365

Val Leu Ser Thr Leu Leu His Asp Pro Glu Ile Leu Arg Ser Tyr Leu
    370                 375                 380

Cys Ser Pro Thr Ser Gly Asn Ser Lys Phe Leu Val Gln Leu Ile Asn
385                 390                 395                 400

Leu Phe Ile Thr Asp Lys Asp Ile Gly Val Lys Asn Gln Ile Val Glu
            405                 410                 415

Ile Ile Lys Thr Leu Leu Glu Ala Asp Ser Tyr Asp Ser Ser Asp Phe
            420                 425                 430

Phe Arg Leu Phe Tyr Asp Lys Gly Ile Asp Leu Leu Val Ser Pro Leu
        435                 440                 445

Asn Glu Val Tyr Lys Gly Glu Pro Thr Ile Pro Gly Asp Pro Ser Ser
    450                 455                 460

Asn Leu Asp Ser Phe Val Leu Tyr Asn Ile Met Glu Leu Val Ile Tyr
465                 470                 475                 480

Cys Ile Lys His His Cys Tyr Arg Ile Lys His Phe Ile Val Glu Glu
            485                 490                 495

Gly Ile Ala Lys Lys Ile Leu Arg Tyr Thr Asn Pro Thr Gly Ser Gly
            500                 505                 510

Gly Gly Gly Gly Gly Gly Asn Ser Glu Arg Tyr Leu Ile Leu Gly
        515                 520                 525

Ser Ile Arg Phe Phe Arg Ser Met Val Asn Met Lys Asp Asp Leu Tyr
530                 535                 540

-continued

```
Asn Gln His Ile Ile Gln Glu Asn Leu Phe Glu Pro Ile Ile Glu Val
545                 550                 555                 560

Phe Lys Ser Asn Ile Ser Arg Tyr Asn Leu Leu Asn Ser Ala Ile Ile
                565                 570                 575

Glu Leu Phe Gln Tyr Ile Tyr Lys Glu Asn Ile Arg Asp Leu Ile Val
            580                 585                 590

Tyr Leu Val Glu Arg Tyr Arg Glu Leu Phe Glu Ser Val Thr Tyr Thr
        595                 600                 605

Asp Val Leu Lys Gln Leu Ile Leu Lys Tyr Glu Gln Ile Lys Asp Ser
    610                 615                 620

Ser Phe Glu Ser Pro Glu Thr Ser Cys Asn Asn Asn Asp Ser Ser Ser
625                 630                 635                 640

Asn Asp Ile Asp Ser Lys Pro Ile Ile Gly Asn Asn Lys Ile Asn His
                645                 650                 655

Asn Tyr Gln Arg Thr Gln Arg Glu Ile Asp Glu Glu Glu Glu Glu Ala
            660                 665                 670

Tyr Phe Asn Arg Asp Asp Asp Ser Glu Asp Ser Asp Asp Glu Asp Glu
        675                 680                 685

Leu Ile Pro Ile Ser Ile Asn Asn Asn Asn Asn Asn Asn Asn Asn Asn
690                 695                 700

Lys Gln Ile Cys Thr Asn Asn Glu Asn Asn Met Glu Lys Asn Asp Asp
705                 710                 715                 720

Asn Ile Glu Lys Asp Asn Glu Asn Thr Asn Asn Gly Asn Gly Ser Ser
                725                 730                 735

His Ile Lys Ile Val Asp Tyr Glu Asp Glu Asp Asp Glu Asp Asp Glu
            740                 745                 750

Ile Asn Lys Ser Val Glu Ser Asp Asp Ile Val Glu Lys His Glu Ile
        755                 760                 765

Ile Asp Lys Asn Glu Lys Lys Asp Glu Ile Met Lys Glu Asn Asn Asp
770                 775                 780

Ser Asp Asn Asp Asp Asn Asp Asn Asn Asp Asn Asp Asn Asp Asn Asp
785                 790                 795                 800

Asn Asn Ser Asp Ile Glu Asn Lys Asn His Leu Asn Asn Asn Gly Asn
                805                 810                 815

Asn Glu Asn Asn Glu Asn Asn Asp Asp Val Gln Asp Lys Ser Asn Asn
            820                 825                 830

Lys Asn Asn Ser Asp Lys Ile Asn Glu Asp Gly Lys Ile Glu Lys Gln
        835                 840                 845

Asp Glu Met Lys Glu Asn Leu Glu Met Glu Glu Ile Asp Glu Lys Val
850                 855                 860

Lys Glu Lys Gln Pro Lys Asp Ile Lys Lys Glu Asn Gln Ser Gln Pro
865                 870                 875                 880

Asp Glu Thr Val Phe Asn Gly Lys Ser Asn Asn Ser Asn Asn Asn Asn
                885                 890                 895

Asn Asn Asn Asn Asn Asn Ser Asn Asn Gln Glu Ile Gly Asp Asn Arg
            900                 905                 910

Lys Thr Thr Pro Lys Arg Lys Leu Asp Tyr Glu Lys Asn Glu Ser Val
        915                 920                 925

Val Ser Lys Lys Ile Asp Lys Ser Asn Gly Pro Thr Ser Ile Asp Lys
930                 935                 940

Asp Ile Asn Gly Cys Asp Glu Ser Pro Asn Lys Lys Leu Asn Asn Asn
945                 950                 955                 960

Asn Ser Asn Asn Asn Asn Asn Asn Asn Asn Asn Asn Asn Asn Asn Asn
```

```
                965                 970                 975
Asn Asn Asn Asn Asn Asn Asn Asn Asn Asn Asn Asn Asn Asn
            980                 985                 990

Asn Gln Asn Asp Glu Asn Glu Leu Ser Ser Ala Ser Glu Glu Glu
        995                 1000                1005

Glu Gln Leu Glu Asn Gly Lys His Ile Lys Lys Phe Lys Arg Gly Lys
    1010                1015                1020

Lys Asp Ser Asn Asn Ser Ser Asn Asn Ser Asn Asn Ser Ser Pro Thr
1025                1030                1035                1040

Pro Ser Glu Leu His Val
            1045

<210> SEQ ID NO 7
<211> LENGTH: 2463
<212> TYPE: DNA
<213> ORGANISM: Homo sapiens

<400> SEQUENCE: 7
atgaccgaca cccggcggcg ggtgaaggtg tacacgctca acgaggaccg gcagtgggac       60
gaccggggca ccgggcatgt gtcgtctggc tacgtggagc ggctgaaggg catgtccctg      120
cttgtcaggg ctgagagcga cggttctcta cttttagagt cgaaaataaa tcctaacact      180
gcataccaga acaacagga cactctgatt gtgtggtctg aagcagaaaa ttatgacttg       240
gcccttagct tcaagaaaaa gctggatgt gatgaaattt gggagaaaat atgtcaggtt       300
caaggaaagg acccttccgt ggacatcact caggaccttg tggatgaatc tgaagaggag      360
cgttttgatg atatgtcatc gccaggctta gaattgccat cttgtgaatt aagtcgcctt      420
gaagaaattg cagaacttgt ggcatcatct ttaccttcac ctcttcgtcg tgaaaaactt      480
gcactggcac tagaaaatga gggttatatt aaaaagctcc tggagctttt tcatgtgtgt      540
gaagatttgg aaaatattga aggactgcac cacttgtatg aaattatcaa aggcatcttt      600
ctcttgaatc gaactgctct ttttgaagtt atgttctctg aagaatgtat aatggacgtc      660
attggatgtt tagaatatga tcctgcttta tcacaaccac gaaaacacag ggaatttcta      720
acaaaaacag ccaagtttaa agaagtgatt cccatatcag atcctgagct gaaacaaaaa      780
attcatcaga catacagagt tcagtatata caagatatgg ttctaccaac tccttcggtc      840
tttgaagaaa acatgttatc aacacttcac tcttttatct ttttcaataa ggtagagatt      900
gttggcatgt tgcaggaaga tgaaaaattt ctgacagatt tgtttgcaca actaacagat      960
gaagcaacag atgaggaaaa aagacaggaa ttggttaact tttaaaaga attttgtgcg     1020 ttttcccaaa cgctacagcc tcaaaacaga atgcttttt tcaagacttt gtcaaacatg     1080
ggcatattac cagctttaga agtcatcctt ggcatggatg atacacaggt gcgaagtgct     1140
gctactgata tattctcata cttggttgaa tataatccat ccatggtacg agagtttgtc     1200
atgcaggagg cacaacagaa tgatgatgat attttgctca tcaacctcat tatagaacat     1260
atgatttgtg atacagatcc tgaacttgga ggagcagtcc agcttatggg cctgcttcga     1320
actttagttg acccagagaa catgctagcc actgccaata aaacagaaaa gactgaattt     1380 ctgggttttct tctacaagca ctgtatgcat gttctcactg ctcctttact agcaaataca     1440
acagaagaca aacctagtaa agatgatttt cagactgccc aactattggc acttgtattg     1500
gaattgttaa catttgtgt ggagcaccat acctaccaca taagaactac cattattaat     1560
aaggatatcc tccggagagt gctagttctt atggcctcga agcatgcttt cttggcatta     1620
```

-continued

```
tgtgcccttc gttttaaaag aaagattatt ggattaaaag atgagtttta caaccgctac   1680
ataatgaaaa gtttttttgtt tgaaccagta gtgaaagcat ttctcaacaa tggatcccgc   1740
tacaatctga tgaactctgc cataatagag atgtttgaat ttattagagt ggaagatata   1800
aaatcattaa ctgctcatgt aattgaaaat tactggaaag cactggaaga tgtagattat   1860
gtacagacat ttaaaggatt aaaactgaga tttgaacaac aaagagaaag gcaagataat   1920
cccaaacttg acagtatgcg ttccattttg aggaatcaca gatatcgaag agatgccaga   1980
acactagaag atgaagaaga gatgtggttt aacacagatg aagatgacat ggaagatgga   2040
gaagctgtag tgtctccatc tgacaaaact aaaaatgatg atgatattat ggatccaata   2100
agtaaattca tggaaaggaa gaaattaaaa gaaagtgagg aaaaggaagt gcttctgaaa   2160
acaaaccttt ctggacggca gagcccaagt ttcaagcttt ccctgtccag tggaacgaag   2220
actaacctca ccagccagtc atctacaaca aatctgcctg gttctccggg atcacctgga   2280
tccccaggat ctccaggctc tcctggatcc gtacctaaaa atacatctca gacggcagct   2340
attactacaa agggaggcct cgtgggtctg gtagattatc ctgatgatga tgaagatgat   2400
gatgaggatg aagataagga agatacgtta ccattgtcaa agaaagcaaa atttgattca   2460
taa                                                                  2463

<210> SEQ ID NO 8
<211> LENGTH: 2550
<212> TYPE: DNA
<213> ORGANISM: Homo sapiens

<400> SEQUENCE: 8
atgtcggata cgcggcggcg agtgaaggtc tataccctga cgaagaccg gcaatgggac     60 gaccgaggca ccgggcacgt ctcctccact tacgtggagg agctcaaggg gatgtcgctg    120
ctggttcggg cagagtccga cggatcacta ctcttggaat caaagataaa tccaaatact    180
gcatatcaga acaacagga tacattaatt gtttggtcag aagcagagaa ctatgatttg    240
gctctgagtt ttcaggagaa agctggctgt gatgagatct gggaaaaaat ttgtcaggtt    300
caaggtaaag acccatcagt ggaagtcaca caggacctca ttgatgaatc tgaagaagaa    360
cgatttgaag aaatgcctga aactagtcat ctgattgacc tgcccacgtg tgaactcaat    420
aaacttgaag agattgctga cttagttacc tcagtgctct ccctcaccta tccgtagggaa   480 aagctggctc tcgccttgga aaatgaaggc tatattaaaa aactattgca gctgttccaa    540
gcttgcgaga acctagaaaa cactgaaggc ttacaccatt tgtatgaaat tattagagga    600
atcttattcc taaataaggc aactcttttt gaggtaatgt tttctgatga gtgtatcatg    660
gatgtcgtgg gatgccttga atatgaccct gctttggctc agccaaaaag acatagagaa    720
ttcttgacca aaactgcaaa gttcaaggaa gttataccaa taacagactc tgaactaagg    780
caaaaaatac atcagactta cagggtacag tacattcagg acatcatttt gcccacacca    840 tctgttttg aagagaattt tctttctact cttacgtctt ttattttctt caacaaagtt    900
gagatagtca gcatgttgca ggaagatgag aagtttttgt ctgaagtttt tgcacaatta    960
acagatgagg ctacagatga tgataaacgg cgtgaattgg ttaattttt caaggagttt    1020 tgtgcatttt ctcagacatt acaacctcaa aacaggatg cattttcaa aacattggca    1080 aaattgggaa tcttcctgc tcttgaaatt gtaatgggca tggatgattt gcaagtcaga    1140
tcagctgcta cagatatatt ttcttatcta gtagaattta gtccatctat ggtccgagag    1200
tttgtaatgc aagaagctca gcagagtgat gacgatattc ttcttattaa tgtggtaatt    1260
```

```
gaacaaatga tctgtgatac tgatcctgag ctaggaggcg ctgttcagtt aatgggactt    1320
cttcgtactc taattgatcc agagaacatg ctggctacaa ctaataaaac cgaaaaagt    1380 gaatttctaa attttttcta caaccattgt atgcatgttc tcacagcacc acttttgacc   1440
aatacttcag aagacaaatg tgaaaaggat ttttttttaa aacattacag atatagttgg   1500
agtttcgtat gtacccttc acattccat tccattcta cccctcttc ctccatctct       1560 caagataata tagttggatc aaacaaaaac aacacaattt gtcccgataa ttatcaaaca   1620
gcacagctac ttgccttaat tttagagtta ctcacatttt gtgtggaaca tcacacatat   1680
cacataaaaa actatattat gaacaaggac ttgctaagaa gagtcttggt cttgatgaat   1740
tcaaagcaca cttttctggc cttgtgtgcc cttcgcttta tgaggcggat aattggactt   1800
aaagatgaat tttataatcg ttacatcacc aagggaaatc ttttgagcc agttataaat    1860 gcacttctgg ataatggaac tcggtataat ctgttgaatt cagctgttat tgagttgttt   1920
gaatttataa gagtggaaga tatcaagtct cttactgccc atatagttga aaactttat    1980 aaagcacttg aatcgattga atatgttcag acattcaaag gattgaagac taaatatgag   2040
caagaaaaag acagacaaaa tcagaaactg aacagtgtac catctatatt gcgtagtaac   2100
agatttcgca gagatgcaaa agccttggaa gaggatgaag aaatgtggtt taatgaagat   2160
gaagaagagg aaggaaaagc agttgtggca ccagtggaaa aacctaagcc agaagatgat   2220
tttccagata attatgaaaa gtttatggag actaaaaaag caaagaaag tgaagacaag    2280 gaaaaccttc ccaaaaggac atctcctggt ggcttcaaat ttactttctc ccactctgcc   2340
agtgctgcta atgaacaaa cagtaaatct gtagtggctc agataccacc agcaacttct    2400
aatggatcct cttccaaaac cacaaacttg cctacgtcag taacagccac caaggaagt    2460 ttggttggct tagtggatta tccagatgat gaagaggaag atgaagaaga agaatcgtcc   2520
cccaggaaaa gacctcgtct tggctcataa                                    2550
```

<210> SEQ ID NO 9
<211> LENGTH: 3143
<212> TYPE: DNA
<213> ORGANISM: Dictyostelium discoideum

<400> SEQUENCE: 9

```
atggaaccac ttagaaaaag agttaaagtc tatcaattag ataatagcgg aaagtgggat    60
gataaaggta caggtcatgt atcatgtata tatgtagatg cattatgtgc aatgggatta   120
attgttagat cagagagtga taacagtgta attttacaaa ctcgactatc agcagaggat   180
atatatcaaa acaacaagaa ttccttaatc gtttggacag aaccagattc acaattagat   240
ttagccctat catttcaaga ttcattgggt tgtcaggata tttgggagaa catattacaa   300
tatcaaaatc aaagaactgg tagttgtgat agtgtagatt tagatttacc accagtttca   360
atcaataatc ttcaaacaat taatgaatta ttagaagctt cattaccaat gttagataaa   420
gataaaatta taaattcaat ttttaaagag gatttagtaa gatcattatt agatttattt   480
gatgaaattg aaaaatcagg tgaaggagga gttcacttgt ttcaaatatt caatattttt   540
aaaaacctta ttttattcaa tgatacatca attttagagg ttatttttatc agaagattat   600 ttagtaagag ttatgggtgc attagaatat gacccagaaa tttcagaaaa taatagaatt   660
aaacatagag aattttaaa tcaacaagta gttttaaac aagttataaa gttcccatca     720
aaatcattaa ttggaactat tcatcaaaca tttagaattc aatatctaaa agatgttgtt   780
```

-continued

```
ttaccaagag tattggatga tgtcactttc tcatcattaa attcattaat ttattttaat      840
aatatagata tagtttcaca aattcaaaat gattcagatt ttttagaaaa tttattttca      900
gaaatccaaa aaagtgaaaa gaattcagaa gaaagaaaag atttaatatt atttcttcaa      960
gatttatgta atttagcaaa aggattacaa attcaaagta aatcaacatt ttttacagtt     1020
gtagtttcat taggattatt taaaacttta tcagcaatct tggatgatga aaatgtacaa     1080
accagagtat catgtacaga gattgtatta tcgacattat tacatgatcc agaaatttta     1140
agatcatatc tatgttctcc aaccagtgga aatagtaaat tcttggttca attaataaat     1200
ttattcataa ctgataaaga tattggtgtt aaaaatcaaa ttgttgaaat tattaaaact     1260
ttattggaag ctgattctta tgattcaagc gatttctttta gattatttta tgataaaggt     1320
atagatttat tagtatcacc attgaatgaa gtttataaag gagagcctac aataccaggt     1380
gatccaagta gtaatttaga ttcatttgta ctctataata aatggagtt ggtaatctat     1440
tgtattaaac atcattgcta tcgtattaaa cattttatag ttgaagaagg tattgcaaaa     1500
aagatattaa ggtatacgaa ccctacaggt agtgggggtg gtggtggtgg tggtggaaat     1560
agtgaaagat atttaatact tggatcaatt agattttta gatcaatggt aaatatgaaa     1620
gatgacctat ataatcaaca tatcattcaa gagaatctat ttgaaccaat cattgaagtt     1680
ttcaaatcaa acatttctag gtataatcta ttaaattcag caatcataga actatttcaa     1740
tacatctaca aagagaacat tagggattta attgtttatt tagtcgaaag gtatagagaa     1800
ttgtttgaat cggtaaccta taccgacgtt ttaaaacaat tgattttaaa gtatgaacaa     1860
attaaggatt cttcatttga aagtccagaa acatcttgta ataataacga tagcagtagc     1920
aatgatattg atagcaaacc tatcattggt aataataaaa ttaatcataa ttatcaaaga     1980
actcaaagag aaatcgatga ggaagaagaa gaagcttatt ttaatagaga tgatgattct     2040
gaagattctg atgatgaaga tgaattaatt ccgatttcaa ttaataataa taataataac     2100
aataataata ataaacaaat ttgtacaaat aatgaaaata atatggagaa aaatgatgat     2160
aatatagaaa aggataatga aaatactaat aatggaaatg gtagtagtca tataaagatt     2220
gtagattatg aagacgaaga tgatgaagat gatgaaatta ataaatctgt agaaagtgat     2280
gatattgttg aaaaacatga aataatagat aaaaatgaaa aaaagatga aataatgaaa     2340
gaaaataatg atagtgataa tgatgataat gataataatg ataatgacaa tgataatgat     2400
aataaatagcg atatagaaaa taaaaatcat cttaataata atggtaataa tgaaaataat     2460
gaaaataatg acgatgttca agataaaagt aacaacaaaa acaatagtga taaaataaac     2520
gaagatgaaa aaatagaaaa acaagatgaa atgaaagaga atttagaaat ggaagaaata     2580
gatgaaaaag ttaaagaaaa acaacccaaa gatattaaaa aagaaaacca atcacagcca     2640
gacgaaactg tttttaatgg taaaagtaat aattcaaata ataataataa taataataat     2700
aataatagca ataatcaaga gattggagat aataggaaaa caacaccaaa aagaaaattg     2760
gattatgaaa aaaatgaatc tgttgtttca agaaaattg ataaaagtaa tggaccaact     2820
tcaatagaca aagatattaa tggttgcgat gaatcaccaa ataaaaaatt aaataataat     2880
aatagtaaca ataataataa taataataat ataataataa taataataat taataataat     2940
aataataata ataataataa taataataat aacaacaatc aaaatgatga aatgaattaa     3000
tcaagtgcat cagaagaaga agaagaacag ttagagaatg gaaaacatat aaagaaattc     3060
aaaagaggga aaaagattc aaataattcc agtaataatt caaataatag tagtccaact     3120
cctagtgaac tacatgttta aat                                             3143
```

<210> SEQ ID NO 10
<211> LENGTH: 3258
<212> TYPE: DNA
<213> ORGANISM: Caenorhabditis elegans

<400> SEQUENCE: 10

| | | | | | |
|---|---|---|---|---|---|
| atgtcggaca | caaaagaggt | atctgatgat | ccgatggagc | ttggaacgag | ttcaacagtt | 60 |
| atcgctaagg | aggaaaatga | caaggaaagc | ctgaaaagaa | tggaagtaga | cgatgagaaa | 120 |
| gaacctgaag | aagaaatcgt | tgagaaaact | gaagagaaac | aggaagaaga | agacgtgaca | 180 |
| gtaaagctag | aagatgaaac | agaaactgag | gtggaaagtg | tggatggtgg | tcaagaagaa | 240 |
| aaagaagttg | ttgatgaaaa | acaggtggat | gcagagcgag | taaataccaa | aacagaagag | 300 |
| ttatcaccga | aaaagaagt | taaagcggag | gaagatcctg | aaactgaaac | aaagaagaag | 360 |
| gatccttctg | agcaaacgaa | tggtcaggtc | aaaaagaaaa | gtgataagca | gagtccaaaa | 420 |
| aagaaagaga | atctgaggg | aaaagaaaat | agtcccggct | caaagctcac | caacagagat | 480 |
| catattcttg | accatcttga | tataaaacga | gacgcaacca | accgtgtgaa | gctttacgtt | 540 |
| ctctgcgatc | aacgaatctg | ggaggaccga | ggtactggtc | atgtcgtcac | tcatcagtta | 600 |
| tcagctgaag | atggagctcc | gtcgaatgct | ggaaatacaa | tggtcctcgt | ccgacttgag | 660 |
| gggcaaaata | aaaacatgct | cgagtcacgg | attcagatgg | acacagtcta | ccaaaaacaa | 720 |
| caggaaactc | taattgtttg | gtccgaaaacc | gatgtgatgg | atttggcatt | atcattccaa | 780 |
| gaaaagtcgg | gatgcgaaga | attatggcaa | aaaatctgcg | aagtacaagg | gagagatcct | 840 |
| ggagatcctg | atgccacttt | cgatgacgga | gacgacagtg | atgttggaga | aatgccatca | 900 |
| tctgctagtc | gcctacaact | tccgccaatt | gaaattggga | ggctgggtga | gcttgatgcg | 960 |
| cttcttcata | tgcatcttac | gacaaacagt | gccagggaaa | aaatgactct | tgctatagaa | 1020 |
| aacgataatg | tcgttacaaa | actttgtgaa | gttttccgga | tgtgcgaaga | tattgaacat | 1080 |
| acagaaggac | tacgaacttt | ttattcaatc | gtgaagaacc | tgttcatgct | caaccgaaac | 1140 |
| actgttatcg | aaatgcttct | cgacgataat | aatatcaaag | acgtaatagg | gatgtttgag | 1200 |
| ttcgatccgg | cttacaaaca | tccaaggaag | caccgtgatt | ttgtctataa | aaaggccaaa | 1260 |
| tttcgcgagg | ttttgaacat | ttcatgtgac | gaacttcgcg | acaagattca | tcggctctac | 1320 |
| cgtgctcaat | acattcagga | tgcgtgtctt | cccagtttgg | gactttttcga | agaaaatctt | 1380 |
| ctctccacac | ttagtagtca | tgtattttc | tgccgtgtcg | acattgtaac | gctacttcaa | 1440 |
| aaagacaaaa | aagcaatgtc | tgagcttttt | gggcaactga | tcagtgaaga | aacagatgtt | 1500 |
| attcgtcggc | gagatctggc | acttttccta | aaagagatga | ttagcctaag | taccagcatc | 1560 |
| ccatcaaacg | gaccagccgc | gacaaaggaa | acctttttca | aattacagct | ccagaacatg | 1620 |
| ttcaactctg | agattttgga | ttcgctggag | ccttgtttca | aatcacctga | tcatgaaaca | 1680 |
| agagcagtaa | tggtggatgt | acttcgaaca | atggtcgatg | cgaatgctca | aatgatccgt | 1740 |
| gactttctgc | tcaagcaatc | caaaacgaaa | gacaaaaatg | aggatgtgct | gctgaatatg | 1800 |
| atgatcagac | atttgttaac | tgatattgat | gttcatttga | cgtctggatc | agagattgtt | 1860 |
| ttgattatga | aaactctgct | agatcccgaa | aatatgacaa | cagtgaaatc | agaagaagc | 1920 |
| gatttcttgc | agctattcta | caatcgttgc | tacgaaagtc | ttctaaagcc | aattcttgag | 1980 |
| aatgtcagcg | gaggaaatat | caaaaaggat | gattacatga | ttgccaatcg | tcaatcggtt | 2040 |
| attcttcgac | ttttaacatt | ctgcgtagaa | catcactcat | tttcaatgcg | acaacgatgt | 2100 |

```
gtatcaaatg atttgatgaa taaggttctt gtattgctca agtcgaagca ttcattcctt    2160
gtcttgtctg cactgaagct tcttcaacgt gtggttactg tcaaagatga taaatacatt    2220
cggtacattg tgaaggagaa ggttctggac ccagtcatgg aatgtttccg taaaaatggc    2280
aaccgctata acattatcaa ctcttctgtc ttgcatttgt tcgagtttgt gagaagcgaa    2340
gatgttcgtc cactcataaa atatgttgtc gaaaatcata tggaagtcgt tgattctgta    2400
aactatgtaa aaacattcaa agagatcaag attcgatacg accaacatcg tgatcgtgaa    2460
gatacgatga gcgttcgttc tgaggacaac tcattggcaa gtccacgaag tttccgcaag    2520
gatcgtaatg aagatcaatg gtttgatgag gatgaagacc tggaagttgg aacaatgctt    2580
gaatcaatcg aaaaggactc agtcgcagtg tctcccaaaa agaagaggc tggacagagg    2640 aagactggta tggagcccat gtttccatca ttactgaagc gcaaaaatgc atttgatgac    2700
gacgaagctc cagtattcgg tggaggatct gctactgtta ttaataatac cgaaaagaaa    2760
attgttataa aggttaacag cgatcgttct ccgtctcgta caccgtctcc tgcatcgtcg    2820
ccccgagcaa gttcctcacc aggaccatcc agagacgatg aagtaacttc atctcaaaac    2880
aacaaagaaa gcagtccgac tcctacggtc aagtcgctgg tcgattacga cgaatcggat    2940
gattctgatg atgatccacc atctcctgac gcagttccct catcttcaac tggaagtcct    3000
gaaaaagaag gagactccgc tgatggaaag aaaggagatt cgccagaata taacgatgta    3060
tcgtcaacta gcaacgaaga gaagttcgac tcacgaaacg gagcgccagt cactaatgaa    3120
aacggaggag tagaagctgc ggcaccaaca gttgaaatca gccgtaaacg cactagtgac    3180
ggtattgatc ctgatgcaaa gagaattcga actgaagaga ctgcaccagc ggcaactgcc    3240
acagtttcgc aggcctaa                                                  3258

<210> SEQ ID NO 11
<211> LENGTH: 2577
<212> TYPE: DNA
<213> ORGANISM: Saccharomyces cerevisiae

<400> SEQUENCE: 11
atgtcattac cgggtacacc tactacatct ccgaccccga tggatgagga tactgaacaa     60
gccgtttcgg ttaatactga acccaaaaga gtaaaggttt acattttaga gaacaacgaa    120
tggaaagaca caggtacagg gttttgtata ggggaggtgg acgaaggtaa gttcgcatat    180
cttgttgtct cagatgaaga ctccccaact gaaactttac taaaatccaa actagaagga    240
aatattgaat atcaacggca ggaggaaacg cttattgttt ggaaggattt agggggggaaa   300 gatatagcct tgagttttga agaaagtatg ggatgtgaca ccttatgtga attcattgtt    360
cacgtccaaa ggaacataga gtcaaatatt tctttagtca ccgtaaaatc cagcgacaac    420
ggactcgggt ctgttcacga cattataacg ggccctgtga ccttgccctc caacgaccag    480
caacagaata gtcaaacttt actagaagct ctaaagattt tgaatgaaaa tacttctttc    540 gatttttga aaaacgaaac cattgagttt atcctccagt caaattacat tgatacactg    600
atttctcatt tccacaaagc agaagaagaa agataccga aggatttatt tttgctaagt    660
aacatcatca aactttgat actttacaat aaaagagaca tattggagtc aatggtggag    720
gacgatagga ttatgggaat agttgggatt tagaatacg atactgaata ccctacatca    780
aaggcaaatc ataggaaata tttaggatca aaaggtccca atttcaaaga ggttattcca    840
ttggaaaatg aggacttaaa aataataatg aaaaatgtt tcgcttaca gttcttaaaa    900 gacgtggtat tagtacgatt tttagacgat cataatttca acttaatctc ggaaattgtc    960
```

```
atggacctgg aaacgtgtat aatcgacttt cttcaagtag ggacgttttt ggacagacta    1020
atagagcttt atgataccaa aacccttcca gaaagctctt cagagaagga gaagtttgta    1080
caaaaacgaa aagacgggat tagattgttg caacagtgtg ttcaaatgtc aatcaattta    1140
gatgcggttg accgttctaa gttctataaa acacttgttc gaaagggtct attcaaagtt    1200
ttagattatg catttcacat ggagacggat agtaatgtta ggattttagc tacggatact    1260
atcattacta taatcgaaca cgatatcttg ttaattcaca cgttcagaa tgaagattct     1320 ttcaaacggc aacataaatc agcgcccgat gacaagtctt cccatcggaa atatccgcag    1380
gattacagct ccagtactga ttccaagttg ttattgatac tttcaaccat tcttctgtcc    1440
gacaggagtc ccggattgcg agaacaagtt gtgcaagcgc taaatacttt gcttcaccct    1500
gaaggatgtg tgggtaatgg agaaggttca tatgatctta tgggcagatc aaattatgaa    1560
gctaagaaca catctgaaga tttcccaagt ttcagttatg gtttaaactc ggattcaatc    1620
aatttaaata actatcacta tagcagcgat gaaatgaata atctagagcc agaatctgaa    1680
tctgaatttc aagtaatgga atattttgca aatttctata ataaaatcgc acccatactg    1740
tttggtccat taatcaagaa ggatatcaca acggaaatgg cagaaataga tgggcaaata    1800
gaaaaggtta caaagacga tctttttgtta attcatttag tgaaattggt atcatttgtt    1860
tgcactgagc atgatcgtgt cttatccaga agattcatat tagaaaacgg tatactagat    1920
tctgttagca aacttatcgg cggtaatcat atgatgcagc taaggttaac agcagtaaga    1980
tgcattaaaa accttatgtg tctcgatgat aaatactatc atcgatatat gatttcaaaa    2040
aatttatatg cgccggtttt taaactcttc caggagaaca tagataagaa taatcttgca    2100
aattcatgca ttcaagattt ttttccgcatt attataacag aatgtagagc ttatcaaagt    2160
gatggccata acagaaagga aaaaaccaat ggttcttatg atggcaacgg taatgacgtc    2220
aaaacgaacg tgaacaacaa taggacaaac tttaccattt taaacaaata cttagttcaa    2280
acatatggtg atgtcttgag aaaagctact gatatcccctt tcatccagga tatgctagaa    2340
accggggaag aaaaccaacc cgatcattct agctttgaaa atagcattga gggggggaat    2400
gacatttctg taaatatgtc aacagatgga tttgcttcga atcatttaga agatattgac    2460
attaaaaacg tcaaaagatt acattctgag attgaacact ttgaaaatga ccccccattat    2520 tctggtgatc agttagcatt taaaaaaagc gttgaccaaa tgaatgcaag tacttga      2577
```

<210> SEQ ID NO 12  
<211> LENGTH: 20  
<212> TYPE: DNA  
<213> ORGANISM: Artificial Sequence  
<220> FEATURE:  
<223> OTHER INFORMATION: Primer act-1 forward

<400> SEQUENCE: 12
gagcacggta tcgtcaccaa                                                20

<210> SEQ ID NO 13  
<211> LENGTH: 22  
<212> TYPE: DNA  
<213> ORGANISM: Artificial Sequence  
<220> FEATURE:  
<223> OTHER INFORMATION: Primer act-1 reverse

<400> SEQUENCE: 13
tgtcatgcca gatcttctcc at                                             22

<210> SEQ ID NO 14
<211> LENGTH: 23
<212> TYPE: DNA
<213> ORGANISM: Artificial Sequence
<220> FEATURE:
<223> OTHER INFORMATION: Primer sod-3 forward

<400> SEQUENCE: 14
ctaaggatgg tggagaacct tca                                           23

<210> SEQ ID NO 15
<211> LENGTH: 22
<212> TYPE: DNA
<213> ORGANISM: Artificial Sequence
<220> FEATURE:
<223> OTHER INFORMATION: Primer sod-3 reverse

<400> SEQUENCE: 15
cgcgcttaat agtgtccatc ag                                            22

<210> SEQ ID NO 16
<211> LENGTH: 27
<212> TYPE: DNA
<213> ORGANISM: Artificial Sequence
<220> FEATURE:
<223> OTHER INFORMATION: Primer smk-1a forward

<400> SEQUENCE: 16
accaacagag atcatattct tgaccat                                       27

<210> SEQ ID NO 17
<211> LENGTH: 26
<212> TYPE: DNA
<213> ORGANISM: Artificial Sequence
<220> FEATURE:
<223> OTHER INFORMATION: Primer smk-1a reverse

<400> SEQUENCE: 17
ggttgcgtct cgttttatat caagat                                        26

<210> SEQ ID NO 18
<211> LENGTH: 21
<212> TYPE: DNA
<213> ORGANISM: Artificial Sequence
<220> FEATURE:
<223> OTHER INFORMATION: Primer daf-16a forward

<400> SEQUENCE: 18
ggaagaactc gatccgtcac a                                             21

<210> SEQ ID NO 19
<211> LENGTH: 22
<212> TYPE: DNA
<213> ORGANISM: Artificial Sequence
<220> FEATURE:
<223> OTHER INFORMATION: Primer daf-16a reverse

<400> SEQUENCE: 19
ttcgcatgaa acgagaatga ag                                            22

<210> SEQ ID NO 20
<211> LENGTH: 23
<212> TYPE: DNA
<213> ORGANISM: Artificial Sequence
<220> FEATURE:
<223> OTHER INFORMATION: Primer daf-15 forward -continued

```
<400> SEQUENCE: 20
gcaatgtgtt cccgttttta gtg                                            23

<210> SEQ ID NO 21
<211> LENGTH: 25
<212> TYPE: DNA
<213> ORGANISM: Artificial Sequence
<220> FEATURE:
<223> OTHER INFORMATION: Primer daf-15 reverse

<400> SEQUENCE: 21
taagtcagca catgttcgaa gtcaa                                          25

<210> SEQ ID NO 22
<211> LENGTH: 36
<212> TYPE: DNA
<213> ORGANISM: Artificial Sequence
<220> FEATURE:
<223> OTHER INFORMATION: Primer for N' fragment forward

<400> SEQUENCE: 22
gttttgcggc cgcatgtcgg acacaaaaga ggtatc                              36

<210> SEQ ID NO 23
<211> LENGTH: 20
<212> TYPE: DNA
<213> ORGANISM: Artificial Sequence
<220> FEATURE:
<223> OTHER INFORMATION: Primer for N' fragment reverse

<400> SEQUENCE: 23
agtgccagat ctcgccgacg                                                20

<210> SEQ ID NO 24
<211> LENGTH: 20
<212> TYPE: DNA
<213> ORGANISM: Artificial Sequence
<220> FEATURE:
<223> OTHER INFORMATION: Primer for C' fragment forward

<400> SEQUENCE: 24
tgctgccctc ccggcatctc                                                20

<210> SEQ ID NO 25
<211> LENGTH: 31
<212> TYPE: DNA
<213> ORGANISM: Artificial Sequence
<220> FEATURE:
<223> OTHER INFORMATION: Primer for C' fragment reverse

<400> SEQUENCE: 25
gttttggtac cctggcctgc gaaactgtgg c                                   31

<210> SEQ ID NO 26
<211> LENGTH: 1046
<212> TYPE: PRT
<213> ORGANISM: Dictyostelium discoideum

<400> SEQUENCE: 26

Met Glu Pro Leu Arg Lys Arg Val Lys Val Tyr Gln Leu Asp Asn Ser
 1               5                  10                  15

Gly Lys Trp Asp Asp Lys Gly Thr Gly His Val Ser Cys Ile Tyr Val
            20                  25                  30
```

-continued

```
Asp Ala Leu Cys Ala Met Gly Leu Ile Val Arg Ser Glu Ser Asp Asn
             35                  40                  45

Ser Val Ile Leu Gln Thr Arg Leu Ser Ala Glu Asp Ile Tyr Gln Lys
 50                  55                  60

Gln Gln Asp Ser Leu Ile Val Trp Thr Glu Pro Asp Ser Gln Leu Asp
65                  70                  75                  80

Leu Ala Leu Ser Phe Gln Asp Ser Leu Gly Cys Gln Asp Ile Trp Glu
                 85                  90                  95

Asn Ile Leu Gln Tyr Gln Asn Gln Arg Thr Gly Ser Cys Asp Ser Val
            100                 105                 110

Asp Leu Asp Leu Pro Pro Val Ser Ile Asn Asn Leu Gln Thr Ile Asn
        115                 120                 125

Glu Leu Leu Glu Ala Ser Leu Pro Met Leu Asp Lys Asp Lys Ile Ile
    130                 135                 140

Asn Ser Ile Phe Lys Glu Asp Leu Val Arg Ser Leu Leu Asp Leu Phe
145                 150                 155                 160

Asp Glu Ile Glu Lys Ser Gly Glu Gly Val His Leu Phe Gln Ile
                165                 170                 175

Phe Asn Ile Phe Lys Asn Leu Ile Leu Phe Asn Asp Thr Ser Ile Leu
            180                 185                 190

Glu Val Ile Leu Ser Glu Asp Tyr Leu Val Arg Val Met Gly Ala Leu
        195                 200                 205

Glu Tyr Asp Pro Glu Ile Ser Glu Asn Asn Arg Ile Lys His Arg Glu
    210                 215                 220

Phe Leu Asn Gln Gln Val Val Phe Lys Gln Val Ile Lys Phe Pro Ser
225                 230                 235                 240

Lys Ser Leu Ile Gly Thr Ile His Gln Thr Phe Arg Ile Gln Tyr Leu
                245                 250                 255

Lys Asp Val Val Leu Pro Arg Val Leu Asp Asp Val Thr Phe Ser Ser
            260                 265                 270

Leu Asn Ser Leu Ile Tyr Phe Asn Asn Ile Asp Ile Val Ser Gln Ile
        275                 280                 285

Gln Asn Asp Ser Asp Phe Leu Glu Asn Leu Phe Ser Glu Ile Gln Lys
    290                 295                 300

Ser Glu Lys Asn Ser Glu Glu Arg Lys Asp Leu Ile Leu Phe Leu Gln
305                 310                 315                 320

Asp Leu Cys Asn Leu Ala Lys Gly Leu Gln Ile Gln Ser Lys Ser Thr
                325                 330                 335

Phe Phe Thr Val Val Ser Leu Gly Leu Phe Lys Thr Leu Ser Ala
            340                 345                 350

Ile Leu Asp Asp Glu Asn Val Gln Thr Arg Val Ser Cys Thr Glu Ile
        355                 360                 365

Val Leu Ser Thr Leu Leu His Asp Pro Glu Ile Leu Arg Ser Tyr Leu
    370                 375                 380

Cys Ser Pro Thr Ser Gly Asn Ser Lys Phe Leu Val Gln Leu Ile Asn
385                 390                 395                 400

Leu Phe Ile Thr Asp Lys Asp Ile Gly Val Lys Asn Gln Ile Val Glu
                405                 410                 415

Ile Ile Lys Thr Leu Leu Glu Ala Asp Ser Tyr Asp Ser Ser Asp Phe
            420                 425                 430

Phe Arg Leu Phe Tyr Asp Lys Gly Ile Asp Leu Leu Val Ser Pro Leu
        435                 440                 445

Asn Glu Val Tyr Lys Gly Glu Pro Thr Ile Pro Gly Asp Pro Ser Ser
```

```
                450                 455                 460
Asn Leu Asp Ser Phe Val Leu Tyr Asn Ile Met Glu Leu Val Ile Tyr
465                 470                 475                 480
Cys Ile Lys His His Cys Tyr Arg Ile Lys His Phe Ile Val Glu Glu
                    485                 490                 495
Gly Ile Ala Lys Lys Ile Leu Arg Tyr Thr Asn Pro Thr Gly Ser Gly
                500                 505                 510
Gly Gly Gly Gly Gly Gly Asn Ser Glu Arg Tyr Leu Ile Leu Gly
                515                 520                 525
Ser Ile Arg Phe Phe Arg Ser Met Val Asn Met Lys Asp Asp Leu Tyr
530                 535                 540
Asn Gln His Ile Ile Gln Glu Asn Leu Phe Glu Pro Ile Ile Glu Val
545                 550                 555                 560
Phe Lys Ser Asn Ile Ser Arg Tyr Asn Leu Leu Asn Ser Ala Ile Ile
                565                 570                 575
Glu Leu Phe Gln Tyr Ile Tyr Lys Glu Asn Ile Arg Asp Leu Ile Val
                580                 585                 590
Tyr Leu Val Glu Arg Tyr Arg Glu Leu Phe Glu Ser Val Thr Tyr Thr
                595                 600                 605
Asp Val Leu Lys Gln Leu Ile Leu Lys Tyr Glu Gln Ile Lys Asp Ser
                610                 615                 620
Ser Phe Glu Ser Pro Glu Thr Ser Cys Asn Asn Asn Asp Ser Ser Ser
625                 630                 635                 640
Asn Asp Ile Asp Ser Lys Pro Ile Ile Gly Asn Asn Lys Ile Asn His
                645                 650                 655
Asn Tyr Gln Arg Thr Gln Arg Glu Ile Asp Glu Glu Glu Glu Ala
                660                 665                 670
Tyr Phe Asn Arg Asp Asp Asp Ser Glu Asp Ser Asp Asp Glu Asp Glu
                675                 680                 685
Leu Ile Pro Ile Ser Ile Asn Asn Asn Asn Asn Asn Asn Asn
                690                 695                 700
Lys Gln Ile Cys Thr Asn Asn Glu Asn Asn Met Glu Lys Asn Asp Asp
705                 710                 715                 720
Asn Ile Glu Lys Asp Asn Glu Asn Thr Asn Asn Gly Asn Gly Ser Ser
                725                 730                 735
His Ile Lys Ile Val Asp Tyr Glu Asp Glu Asp Glu Asp Asp Glu
                740                 745                 750
Ile Asn Lys Ser Val Glu Ser Asp Asp Ile Val Glu Lys His Glu Ile
                755                 760                 765
Ile Asp Lys Asn Glu Lys Lys Asp Glu Ile Met Lys Glu Asn Asn Asp
                770                 775                 780
Ser Asp Asn Asp Asp Asn Asp Asn Asn Asp Asn Asp Asn Asp Asn Asp
785                 790                 795                 800
Asn Asn Ser Asp Ile Glu Asn Lys Asn His Leu Asn Asn Asn Gly Asn
                    805                 810                 815
Asn Glu Asn Asn Glu Asn Asn Asp Asp Val Gln Asp Lys Ser Asn Asn
                820                 825                 830
Lys Asn Asn Ser Asp Lys Ile Asn Glu Asp Glu Lys Ile Glu Lys Gln
                835                 840                 845
Asp Glu Met Lys Glu Asn Leu Glu Met Glu Glu Ile Asp Glu Lys Val
                850                 855                 860
Lys Glu Lys Gln Pro Lys Asp Ile Lys Lys Glu Asn Gln Ser Gln Pro
865                 870                 875                 880
```

```
Asp Glu Thr Val Phe Asn Gly Lys Ser Asn Asn Ser Asn Asn Asn
            885                 890                 895
Asn Asn Asn Asn Asn Asn Ser Asn Asn Gln Glu Ile Gly Asp Asn Arg
        900                 905                 910
Lys Thr Thr Pro Lys Arg Lys Leu Asp Tyr Glu Lys Asn Glu Ser Val
            915                 920                 925
Val Ser Lys Lys Ile Asp Lys Ser Asn Gly Pro Thr Ser Ile Asp Lys
            930                 935                 940
Asp Ile Asn Gly Cys Asp Glu Ser Pro Asn Lys Lys Leu Asn Asn Asn
945                 950                 955                 960
Asn Ser Asn Asn Asn Asn Asn Asn Asn Asn Asn Asn Asn Asn Asn
            965                 970                 975
Asn Asn Asn Asn Asn Asn Asn Asn Asn Asn Asn Asn Asn Asn Asn
            980                 985                 990
Asn Gln Asn Asp Glu Asn Glu Leu Ser Ser Ala Ser Glu Glu Glu
            995                 1000                1005
Glu Gln Leu Glu Asn Gly Lys His Ile Lys Lys Phe Lys Arg Gly Lys
    1010                1015                1020
Lys Asp Ser Asn Asn Ser Ser Asn Asn Ser Asn Asn Ser Ser Pro Thr
1025                1030                1035                1040
Pro Ser Glu Leu His Val
            1045

<210> SEQ ID NO 27
<211> LENGTH: 2463
<212> TYPE: DNA
<213> ORGANISM: Homo sapiens

<400> SEQUENCE: 27
atgaccgaca cccggcggcg ggtgaaggtg tacacgctca acgaggaccg gcagtgggac      60
gaccggggca ccgggcatgt gtcgtctggc tacgtggagc ggctgaaggg catgtccctg     120
cttgtcaggt ctgagagcga cggttctcta cttttagagt cgaaaataaa tcctaacact     180
gcataccaga acaacagga cactctgatt gtgtggtctg aagcagaaaa ttatgacttg     240
gcccttagct ttcaagaaaa agctggatgt gatgaaattt gggagaaaat atgtcaggtt     300
caaggaaagg acccttccgt ggacatcact caggaccttg tggatgaatc tgaagaggag     360
cgttttgatg atatgtcatc gccaggctta gaattgccat cttgtgaatt aagtcgcctt     420
gaagaaattg cagaacttgt ggcatcatct ttaccttcac ctcttcgtcg tgaaaaactt     480
gcactggcac tagaaaatga gggttatatt aaaaagctcc tggagctttt tcatgtgtgt     540
gaagatttgg aaaatattga aggactgcac cacttgtatg aaattatcaa aggcatcttt     600
ctcttgaatc gaactgctct ttttgaagtt atgttctctg aagaatgtat aatggacgtc     660
attggatgtt tagaatatga tcctgcttta tcacaaccac gaaaacacag ggaatttcta     720
acaaaaacag ccaagtttaa agaagtgatt cccatatcag atcctgagct gaaacaaaaa     780
attcatcaga catacagagt tcagtatata caagatatgt ttctaccaac tccttcggtc     840
tttgaagaaa acatgttatc aacacttcac tcttttatct ttttcaataa ggtagagatt     900
gttggcatgt tgcaggaaga tgaaaaattt ctgacagatt tgtttgcaca actaacagat     960
gaagcaacag atgaggaaaa aagacaggaa ttggttaact ttttaaaaga attttgtgcg    1020
ttttcccaaa cgctacagcc tcaaaacaga gatgcttttt tcaagacttt gtcaaacatg    1080
ggcatattac cagctttaga agtcatcctt ggcatggatg atacacaggt gcgaagtgct    1140
```

```
gctactgata tattctcata cttggttgaa tataatccat ccatggtacg agagtttgtc    1200
atgcaggagg cacaacagaa tgatgatgat attttgctca tcaacctcat tatagaacat    1260
atgatttgtg atacagatcc tgaacttgga ggagcagtcc agcttatggg cctgcttcga    1320
actttagttg acccagagaa catgctagcc actgccaata aaacagaaaa gactgaattt    1380
ctgggtttct tctacaagca ctgtatgcat gttctcactg ctcctttact agcaaataca    1440
acagaagaca aacctagtaa agatgatttt cagactgccc aactattggc acttgtattg    1500
gaattgttaa cattttgtgt ggagcaccat acctaccaca taagaactca cattattaat    1560
aaggatatcc tccggagagt gctagttctt atggcctcga agcatgcttt cttggcatta    1620
tgtgcccttc gttttaaaag aaagattatt ggattaaaag atgagtttta caaccgctac    1680
ataatgaaaa gttttttgtt tgaaccagta gtgaaagcat ttctcaacaa tggatcccgc    1740
tacaatctga tgaactctgc cataatagag atgtttgaat ttattagagt ggaagatata    1800
aaatcattaa ctgctcatgt aattgaaaat tactggaaag cactggaaga tgtagattat    1860
gtacagacat ttaaaggatt aaaactgaga tttgaacaac aaagagaaag gcaagataat    1920
cccaaacttg acagtatgcg ttccattttg aggaatcaca gatatcgaag agatgccaga    1980
acactagaag atgaagaaga gatgtggttt aacacagatg aagatgacat ggaagatgga    2040
gaagctgtag tgtctccatc tgacaaaact aaaaatgatg atgatattat ggatccaata    2100
agtaaattca tggaaaggaa gaaattaaaa gaagtgaggg aaaaggaagt gcttctgaaa    2160
acaaaccttt ctggacggca gagcccaagt ttcaagcttt ccctgtccag tggaacgaag    2220
actaacctca ccagccagtc atctacaaca aatctgcctg gttctccggg atcacctgga    2280
tccccaggat ctccaggctc tcctggatcc gtacctaaaa atacatctca gacggcagct    2340
attactacaa agggaggcct cgtgggtctg gtagattatc ctgatgatga tgaagatgat    2400
gatgaggatg aagataagga agatacgtta ccattgtcaa agaaagcaaa atttgattca    2460
taa                                                                  2463
```

<210> SEQ ID NO 28
<211> LENGTH: 2550
<212> TYPE: DNA
<213> ORGANISM: Homo sapiens

<400> SEQUENCE: 28

```
atgtcggata cgcggcggcg agtgaaggtc tataccctga cgaagaccg gcaatgggac      60 gaccgaggca ccgggcacgt ctcctccact tacgtggagg agctcaaggg gatgtcgctg     120
ctggttcggg cagagtccga cggatcacta ctcttggaat caaagataaa tccaaatact     180
gcatatcaga acaacagga tacattaatt gtttggtcag aagcagagaa ctatgatttg     240
gctctgagtt ttcaggagaa agctggctgt gatgagatcc gggaaaaaat ttgtcaggtt     300
caaggtaaag acccatcagt ggaagtcaca caggacctca ttgatgaatc tgaagaagaa     360
cgatttgaag aaatgcctga aactagtcat ctgattgacc tgcccacgtg tgaactcaat     420
aaacttgaag agattgctga cttagttacc tcagtgctct cctcacctat ccgtagggaa     480
aagctggctc tcgccttgga aaatgaaggc tatattaaaa actattgca gctgttccaa     540 gcttgcgaga acctagaaaa cactgaaggc ttacaccatt tgtatgaaat tattagagga     600
atcttattcc taaataaggc aactctttt gaggtaatgt tttctgatga gtgtatcatg     660
gatgtcgtgg gatgccttga atatgaccct gctttggctc agccaaaaag acatagagaa     720
```

```
ttcttgacca aaactgcaaa gttcaaggaa gttataccaa taacagactc tgaactaagg      780
caaaaaatac atcagactta cagggtacag tacattcagg acatcatttt gcccacacca      840
tctgttttg  aagagaattt tctttctact cttacgtctt ttattttctt caacaaagtt      900
gagatagtca gcatgttgca ggaagatgag aagtttttgt ctgaagtttt tgcacaatta      960
acagatgagg ctacagatga tgataaacgg cgtgaattgg ttaattttt  caaggagttt     1020
tgtgcatttt ctcagacatt acaacctcaa acagggatg  cattttcaa  aacattggca     1080
aaattgggaa ttcttcctgc tcttgaaatt gtaatgggca tggatgattt gcaagtcaga     1140
tcagctgcta cagatatatt ttcttatcta gtagaattta gtccatctat ggtccgagag     1200
tttgtaatgc aagaagctca gcagagtgat gacgatattc ttcttattaa tgtggtaatt     1260
gaacaaatga tctgtgatac tgatcctgag ctaggaggcg ctgttcagtt aatgggactt     1320
cttcgtactc taattgatcc agagaacatg ctggctacaa ctaataaaac cgaaaaaagt     1380
gaatttctaa attttttcta caaccattgt atgcatgttc tcacagcacc acttttgacc     1440
aatacttcag aagacaaatg tgaaaaggat ttttttttaa aacattacag atatagttgg     1500
agtttcgtat gtaccccttc acattcccat tcccattcta ccccctcttc ctccatctct     1560
caagataata tagttggatc aaacaaaaac aacacaattt gtcccgataa ttatcaaaca     1620
gcacagctac ttgccttaat tttagagtta ctcacatttt gtgtgaaaca tcacacatat     1680
cacataaaaa actatattat gaacaaggac ttgctaagaa gagtcttggt cttgatgaat     1740
tcaaagcaca cttttctggc cttgtgtgcc cttcgcttta tgaggcggat aattggactt     1800
aaagatgaat tttataatcg ttacatcacc aagggaaatc ttttttgagcc agttataaat     1860
gcacttctgg ataatggaac tcggtataat ctgttgaatt cagctgttat tgagttgttt     1920
gaatttataa gagtggaaga tatcaagtct cttactgccc atatagttga aaactttat      1980
aaagcacttg aatcgattga atatgttcag acattcaaag gattgaagac taaatatgag     2040
caagaaaaag acagacaaaa tcagaaactg aacagtgtac catctatatt gcgtagtaac     2100
agatttcgca gagatgcaaa agccttggaa gaggatgaag aaatgtggtt taatgaagat     2160
gaagaagagg aaggaaaagc agttgtggca ccagtggaaa aacctaagcc agaagatgat     2220
tttccagata attatgaaaa gtttatggag actaaaaaag caaagaaag  tgaagacaag     2280
gaaaaccttc ccaaaaggac atctcctggt ggcttcaaat ttactttctc ccactctgcc     2340
agtgctgcta atgaacaaa  cagtaaatct gtagtggctc agataccacc agcaacttct     2400
aatggatcct cttccaaaac cacaaacttg cctacgtcag taacagccac caaggaagt      2460
ttggttggct tagtggatta tccagatgat gaagaggaag atgaagaaga agaatcgtcc     2520
cccaggaaaa gacctcgtct tggctcataa                                      2550
```

<210> SEQ ID NO 29
<211> LENGTH: 3143
<212> TYPE: DNA
<213> ORGANISM: Dictyostelium discodeum

<400> SEQUENCE: 29

```
atggaaccac ttagaaaaag agttaaagtc tatcaattag ataatagcgg aaagtgggat       60
gataaaggta caggtcatgt atcatgtata tatgtagatg cattatgtgc aatgggatta      120
attgttagat cagagagtga taacagtgta attttacaaa ctcgactatc agcagaggat      180
atatatcaaa acaacaagaa ttccttaatc gtttggacag aaccagattc acaattagat      240
ttagccctat catttcaaga ttcattgggt tgtcaggata tttgggagaa catattacaa      300
```

-continued

```
tatcaaaatc aaagaactgg tagttgtgat agtgtagatt tagatttacc accagtttca    360
atcaataatc ttcaaacaat taatgaatta ttagaagctt cattaccaat gttagataaa    420
gataaaatta taaattcaat ttttaaagag gatttagtaa gatcattatt agatttattt    480
gatgaaattg aaaaatcagg tgaaggagga gttcacttgt ttcaaatatt caatattttt    540
aaaaacctta ttttattcaa tgatacatca atttagagg ttattttatc agaagattat     600
ttagtaagag ttatgggtgc attagaatat gacccagaaa tttcagaaaa taatagaatt    660
aaacatagag aattttaaa tcaacaagta gttttaaac aagttataaa gttcccatca      720
aaatcattaa ttggaactat tcatcaaaca tttagaattc aatatctaaa agatgttgtt    780
ttaccaagag tattggatga tgtcactttc tcatcattaa attcattaat ttatttaat    840
aatatagata tagtttcaca aattcaaaat gattcagatt ttttagaaaa tttattttca    900
gaaatccaaa aaagtgaaaa gaattcagaa gaaagaaaag atttaatatt atttcttcaa    960
gatttatgta atttagcaaa aggattacaa attcaaagta aatcaacatt ttttacagtt    1020
gtagtttcat taggattatt taaaacttta tcagcaatct tggatgatga aaatgtacaa    1080
accagagtat catgtacaga gattgtatta tcgacattat tacatgatcc agaaatttta    1140
agatcatatc tatgttctcc aaccagtgga aatagtaaat tcttggttca attaataaat    1200
ttattcataa ctgataaaga tattggtgtt aaaaatcaaa ttgttgaaat tattaaaact    1260
ttattggaag ctgattctta tgattcaagc gatttcttta gattatttta tgataaaggt    1320
atagatttat tagtatcacc attgaatgaa gtttataaag gagagcctac aataccaggt    1380
gatccaagta gtaatttaga ttcatttgta ctctataata taatggagtt ggtaatctat    1440
tgtattaaac atcattgcta tcgtattaaa cattttatag ttgaagaagg tattgcaaaa    1500
aagatattaa ggtatacgaa ccctacaggt agtgggggtg gtggtggtgg tggtggaaat    1560
agtgaaagat atttaatact tggatcaatt agatttttta gatcaatggt aaatatgaaa    1620
gatgacctat ataatcaaca tatcattcaa gagaatctat ttgaaccaat cattgaagtt    1680
ttcaaatcaa acatttctag gtataatcta ttaaattcag caatcataga actatttcaa    1740
tacatctaca aagagaacat tagggattta attgtttatt tagtcgaaag gtatagagaa    1800
ttgtttgaat cggtaaccta taccgacgtt ttaaaacaat tgattttaaa gtatgaacaa    1860
attaaggatt cttcatttga aagtccagaa acatcttgta ataataacga tagcagtagc    1920
aatgatattg atagcaaacc tatcattggt aataataaaa ttaatcataa ttatcaaaga    1980
actcaaagag aaatcgatga ggaagaagaa gaagcttatt ttaatagaga tgatgattct    2040
gaagattctg atgatgaaga tgaattaatt ccgatttcaa ttaataataa taataataac    2100
aataataata taaacaaat ttgtacaaat aatgaaaata tatggagaa aaatgatgat      2160
aatatagaaa aggataatga aaatactaat aatggaaatg gtagtagtca tataaagatt    2220
gtagattatg aagacgaaga tgatgaagat gatgaaatta ataaatctgt agaaagtgat    2280
gatattgttg aaaacatga aataatagat aaaaatgaaa aaaagatga aataatgaaa      2340
gaaaataatg atagtgataa tgatgataat gataataatg taatgacaa tgataatgat    2400
aataatagcg atatagaaaa taaaaatcat cttaataata atggtaataa tgaaaataat    2460
gaaaataatg acgatgttca agataaaagt aacaacaaaa acaatagtga taaaataaac    2520
gaagatgaaa aaatagaaaa acaagatgaa atgaaagaga atttagaaat ggaagaaata    2580
gatgaaaaag ttaagaaaaa acaacccaaa gatattaaaa aagaaaacca atcacagcca    2640
```

-continued

| | |
|---|---|
| gacgaaactg tttttaatgg taaaagtaat aattcaaata ataataataa taataataat | 2700 |
| aataatagca ataatcaaga gattggagat aataggaaaa caacaccaaa aagaaaattg | 2760 |
| gattatgaaa aaaatgaatc tgttgtttca aagaaaattg ataaaagtaa tggaccaact | 2820 |
| tcaatagaca aagatattaa tggttgcgat gaatcaccaa ataaaaaatt aaataataat | 2880 |
| aatagtaaca ataataataa taataataat aataataata ataataataa taataataat | 2940 |
| aataataata ataataataa taataataat aacaacaatc aaaatgatga aaatgaatta | 3000 |
| tcaagtgcat cagaagaaga agaagaacag ttagagaatg gaaacatat aaagaaattc | 3060 |
| aaaagaggga aaaaagattc aaataattcc agtaataatt caaataatag tagtccaact | 3120 |
| cctagtgaac tacatgttta aat | 3143 |

<210> SEQ ID NO 30
<211> LENGTH: 3258
<212> TYPE: DNA
<213> ORGANISM: Caenorhabditis elegans

<400> SEQUENCE: 30

| | |
|---|---|
| atgtcggaca caaaagaggt atctgatgat ccgatggagc ttggaacgag ttcaacagtt | 60 |
| atcgctaagg aggaaaatga caaggaaagc ctgaaaagaa tggaagtaga cgatgagaaa | 120 |
| gaacctgaag aagaaatcgt tgagaaaact gaagagaaac aggaagaaga agacgtgaca | 180 |
| gtaaagctag aagatgaaac agaaactgag gtggaaagtg tggatggtgg tcaagaagaa | 240 |
| aaagaagttg ttgatgaaaa acaggtggat gcagagcgag taaataccaa aacagaagag | 300 |
| ttatcaccga aaaagaagt taaagcggag aagatcctg aaactgaaac aaagaagaag | 360 |
| gatccttctg agcaaacgaa tggtcaggtc aaaaagaaaa gtgataagca gagtccaaaa | 420 |
| aagaaagaga atctgaggg aaaagaaaat agtcccggct caaagctcac caacagagat | 480 |
| catattcttg accatcttga tataaaacga gacgcaacca accgtgtgaa gctttacgtt | 540 |
| ctctgcgatc aacgaatctg ggaggaccga ggtactggtc atgtcgtcac tcatcagtta | 600 |
| tcagctgaag atggagctcc gtcgaatgct ggaaatacaa tggtcctcgt ccgacttgag | 660 |
| gggcaaaata aaaacatgct cgagtcacgg attcagatgg acacagtcta ccaaaaacaa | 720 |
| caggaaactc taattgtttg gtccgaaacc gatgtgatgg atttggcatt atcattccaa | 780 |
| gaaaagtcgg gatgcgaaga attatggcaa aaaatctgcg aagtacaagg agagatcct | 840 |
| ggagatcctg atgccacttt cgatgacgga gacgacagtg atgttggaga atgccatca | 900 |
| tctgctagtc gcctacaact tccgccaatt gaaattggga ggctgggtga gcttgatgcg | 960 |
| cttcttcata tgcatcttac gacaaacagt gccagggaaa aaatgactct tgctatagaa | 1020 |
| aacgataatg tcgttacaaa actttgtgaa gttttccgga tgtgcgaaga tattgaacat | 1080 |
| acagaaggac tacgaacttt ttattcaatc gtgaagaacc tgttcatgct caaccgaaac | 1140 |
| actgttatcg aaatgcttct cgacgataat aatatcaaag acgtaatagg gatgtttgag | 1200 |
| ttcgatccgg cttacaaaca tccaaggaag caccgtgatt tgtctataa aaaggccaaa | 1260 |
| tttcgcgagg ttttgaacat ttcatgtgac gaacttcgcg acaagattca tcggctctac | 1320 |
| cgtgctcaat acattcagga tgcgtgtctt cccagtttgg gacttttcga agaaaatctt | 1380 |
| ctctccacac ttagtagtca tgtatttttc tgccgtgtcg acattgtaac gctacttcaa | 1440 |
| aaagacaaaa aagcaatgtc tgagcttttt gggcaactga tcagtgaaga aacagatgtt | 1500 |
| attcgtcggc gagatctggc acttttccta aaagagatga ttagcctaag taccagcatc | 1560 |
| ccatcaaacg gaccagccgc gacaaaggaa accttttttca aattacagct ccagaacatg | 1620 |

```
ttcaactctg agattttgga ttcgctggag ccttgtttca aatcacctga tcatgaaaca    1680
agagcagtaa tggtggatgt acttcgaaca atggtcgatg cgaatgctca aatgatccgt    1740
gactttctgc tcaagcaatc caaaacgaaa gacaaaaatg aggatgtgct gctgaatatg    1800
atgatcagac atttgttaac tgatattgat gttcatttga cgtctggatc agagattgtt    1860
ttgattatga aaactctgct agatcccgaa aatatgacaa cagtgaaatc agaaagaagc    1920
gatttcttgc agctattcta caatcgttgc tacgaaagtc ttctaaagcc aattcttgag    1980
aatgtcagcg gaggaaatat caaaaaggat gattacatga ttgccaatcg tcaatcggtt    2040
attcttcgac ttttaacatt ctgcgtagaa catcactcat tttcaatgcg acaacgatgt    2100
gtatcaaatg atttgatgaa taaggttctt gtattgctca agtcgaagca ttcattcctt    2160
gtcttgtctg cactgaagct tcttcaacgt gtggttactg tcaaagatga taaatacatt    2220
cggtacattg tgaaggagaa ggttctggac ccagtcatgg aatgtttccg taaaaatggc    2280
aaccgctata acattatcaa ctcttctgtc ttgcatttgt tcgagtttgt gagaagcgaa    2340
gatgttcgtc cactcataaa atatgttgtc gaaaatcata tggaagtcgt tgattctgta    2400
aactatgtaa aaacattcaa agagatcaag attcgatacg accaacatcg tgatcgtgaa    2460
gatacgatga gcgttcgttc tgaggacaac tcattggcaa gtccacgaag tttccgcaag    2520
gatcgtaatg aagatcaatg gtttgatgag gatgaagacc tggaagttgg aacaatgctt    2580
gaatcaatcg aaaaggactc agtcgcagtg tctcccaaaa agaagaggc tggacagagg    2640
aagactggta tggagcccat gtttccatca ttactgaagc gcaaaaatgc atttgatgac    2700
gacgaagctc cagtattcgg tggaggatct gctactgtta ttaataatac cgaaaagaaa    2760
attgttataa aggttaacag cgatcgttct ccgtctcgta caccgtctcc tgcatcgtcg    2820
ccccgagcaa gttcctcacc aggaccatcc agagacgatg aagtaacttc atctcaaaac    2880
aacaaagaaa gcagtccgac tcctacggtc aagtcgctgg tcgattacga cgaatcggat    2940
gattctgatg atgatccacc atctcctgac gcagttccct catcttcaac tggaagtcct    3000
gaaaaagaag gagactccgc tgatggaaag aaaggagatt cgccagaata taacgatgta    3060
tcgtcaacta gcaacgaaga gaagttcgac tcacgaaacg gagcgccagt cactaatgaa    3120
aacggaggag tagaagctgc ggcaccaaca gttgaaatca gccgtaaacg cactagtgac    3180
ggtattgatc ctgatgcaaa gagaattcga actgaagaga ctgcaccagc ggcaactgcc    3240
acagtttcgc aggcctaa                                                 3258
```

<210> SEQ ID NO 31
<211> LENGTH: 2577
<212> TYPE: DNA
<213> ORGANISM: Saccharomyces cerevisiae

<400> SEQUENCE: 31

```
atgtcattac cgggtacacc tactacatct ccgaccccga tggatgagga tactgaacaa     60
gccgtttcgg ttaatactga acccaaaaga gtaaaggttt acattttaga gaacaacgaa    120
tggaaagaca caggtacagg gttttgtata ggggaggtgg acgaaggtaa gttcgcatat    180
cttgttgtct cagatgaaga ctccccaact gaaactttac taaaatccaa actagaagga    240
aatattgaat atcaacggca ggaggaaacg cttattgttt ggaaggattt agggggaaa     300
gatatagcct tgagttttga agaaagtatg ggatgtgaca ccttatgtga attcattgtt    360
cacgtccaaa ggaacataga gtcaaatatt tctttagtca ccgtaaaatc cagcgacaac    420
```

```
                                                               -continued
ggactcgggt ctgttcacga cattataacg ggccctgtga ccttgccctc caacgaccag       480
caacagaata gtcaaacttt actagaagct ctaaagattt tgaatgaaaa tacttctttc       540 gatttttga aaaacgaaac cattgagttt atcctccagt caaattacat tgatacactg       600
atttctcatt tccacaaagc agaagaagaa aagataccga aggatttatt tttgctaagt       660
aacatcatca aaactttgat actttacaat aaaagagaca tattggagtc aatggtggag       720
gacgatagga ttatgggaat agttgggatt ttagaatacg atactgaata ccctacatca       780
aaggcaaatc ataggaaata tttaggatca aaaggtccca atttcaaaga ggttattcca       840
ttggaaaatg aggacttaaa aataataatg aaaaaatgtt ttcgcttaca gttcttaaaa       900
gacgtggtat tagtacgatt tttagacgat cataatttca acttaatctc ggaaattgtc       960
atggacctgg aaacgtgtat aatcgacttt cttcaagtag ggacgttttt ggacagacta      1020
atagagcttt atgataccaa aacccttcca gaaagctctt cagagaagga gaagtttgta      1080
caaaaacgaa aagacgggat tagattgttg caacagtgtg ttcaaatgtc aatcaattta      1140
gatgcggttg accgttctaa gttctataaa acacttgttc gaaagggtct attcaaagtt      1200
ttagattatg catttcacat ggagacggat agtaatgtta ggattttagc tacggatact      1260
atcattacta taatcgaaca cgatatcttg ttaattcaca acgttcagaa tgaagattct      1320
ttcaaacggc aacataaatc agcgcccgat gacaagtctt cccatcggaa atatccgcag      1380
gattacagct ccagtactga ttccaagttg ttattgatac tttcaaccat tcttctgtcc      1440
gacaggagtc ccggattgcg agaacaagtt gtgcaagcgc taaatacttt gcttcaccct      1500
gaaggatgtg tgggtaatgg agaaggttca tatgatctta tgggcagatc aaattatgaa      1560
gctaagaaca catctgaaga tttcccaagt ttcagttatg gtttaaactc ggattcaatc      1620
aatttaaata actatcacta tagcagcgat gaaatgaata atctagagcc agaatctgaa      1680
tctgaatttc aagtaatgga atattttgca aatttctata ataaaatcgc acccatactg      1740
tttggtccat taatcaagaa ggatatcaca acggaaatgg cagaaataga tgggcaaata      1800
gaaaaggtta caaaagacga tcttttgtta attcatttag tgaaattggt atcatttgtt      1860
tgcactgagc atgatcgtgt cttatccaga agattcatat tagaaaacgg tatactagat      1920
tctgttagca aacttatcgg cggtaatcat atgatgcagc taaggttaac agcagtaaga      1980
tgcattaaaa accttatgtg tctcgatgat aaatactatc atcgatatat gatttcaaaa      2040
aatttatatg cgccggtttt taaactcttc caggagaaca tagataagaa taatcttgca      2100
aattcatgca ttcaagattt tttccgcatt attataacag aatgtagagc ttatcaaagt      2160
gatggccata acagaaagga aaaaaccaat ggttcttatg atggcaacgg taatgacgtc      2220
aaaacgaacg tgaacaacaa taggacaaac tttaccattt taaacaaata cttagttcaa      2280
acatatggtg atgtcttgag aaaagctact gatatccctt tcatccagga tatgctagaa      2340
accggggaag aaaaccaacc cgatcattct agctttgaaa atagcattga aggggggaat      2400
gacatttctg taaatatgtc aacagatgga tttgcttcga atcatttaga agatattgac      2460
attaaaaacg tcaaaagatt acattctgag attgaacact ttgaaaatga ccccattat       2520 tctggtgatc agttagcatt taaaaaaagc gttgaccaaa tgaatgcaag tacttga        2577
```

INCREASING LIFE SPAN BY MODULATION OF SMEK

RELATED APPLICATIONS

This application is a continuation of U.S. patent application Ser. No. 11/165,819 filed Jun. 24, 2005 now U.S. Pat. No. 7,288,385, which claims the benefit of U.S. Provisional Application No. 60/583,284 filed Jun. 25, 2004, both incorporated herein by reference in their entirety.

GOVERNMENT SUPPORT

This invention was made with United States government support under Grant No. RO1 CA082683, Grant No. 5 F32 DK060367, Grant No. CA054418, and Grant No. DK070696 from the National Institutes of Health. The United States Government has certain rights in this invention.

BACKGROUND OF THE INVENTION

1. Field of the Invention

The field of the invention relates to methods of modulating at least one trait in an animal. Such traits include increased life span, enhanced stress resistance and other traits associated with the stress response pathway. Also encompassed are transgenic animals produced by the disclosed methods.

2. Description of the Related Art

Stress response is a physiological phenomenon universal to all living species, which are constantly exposed to internal and external environmental challenges. Naturally the ability of an organism to react to various stress conditions plays a critical role in determining its chances of survival. One interesting example is the phenomenon of organismal longevity, i.e. long-term survival of an organism, which is closely associated stress resistance from species diverse as yeast and mammals (Guarente and Kenyon 2000; Kenyon 2001; Burgering and Kops 2002; Hekimi and Guarente 2003). Recent studies in model organisms, especially *C. elegans*, showed that the aging process is regulated by a conserved mechanism (Kenyon 2001). It has been well established that mutations in the insulin/IGF-1 signaling pathway in worm leads to extended life span, which is dependent on Daf16, a homolog of the vertebrate forkhead transcription factors (FOXOs) (Kenyon 2001). Among multiple processes perturbed in these long lived mutants, it is striking that stress resistance is the one that is most tightly coupled to longevity (Kenyon 2001). This raises the possibility that signaling pathways mediating stress response might play a direct role in life span extension, which is supported by recent findings on the stress-dependent regulation of FOXO by histone deacetylase SIRT1 (Brunet, Sweeney et al. 2004; Motta, Divecha et al. 2004).

Stress response pathways mediate cellular responses towards various physiological and environmental stress signals. Members of a family of stress activated kinases, including JNK and p38 MAP kinases, play a central role in stress response pathways (Chang and Karin 2001; Morrison and Davis 2003). Only a few studies, however, have directly examined and demonstrated a role for stress signaling proteins in the aging process (Wang, Bohmann et al. 2003). Indeed the molecular links that connect stress signaling to aging, and how signals from distinct pathways such as stress response pathway and insulin/IGF-1 pathway may be integrated to specify life span, are poorly understood. Filling such a gap by unifying these two major signaling routes will not only advance our understanding of the mechanisms of aging, but also provide insights into the signaling network implicated in various human diseases including cancer and diabetes. Thus there is a need for identification of the molecular links that connect the stress response to aging. Further, there is a need for methods of modulation of that molecular link to extend life span and increase stress tolerance of animals.

SUMMARY OF THE INVENTION

The present invention meets the above needs by providing the identity of a key protein family that ties the stress signaling pathway with aging. Identification of this protein family, Suppressor of MEK null (Smek), has led to various aspects of the present invention as set forth below including, without limitation, methods of increasing the lifespan of animals, methods of screening for compounds that increase the life span of an animal and/or modulate the stress response of an animal, and transgenic animals and cells that have a longer life span and/or enhanced resistance to stress.

One aspect of the present invention includes a method of increasing the life span of animal by modulating the activity or expression of a Smek protein. The method includes administering to the animal a compound that modulates the activity or expression of a Smek protein. In certain embodiments in higher organisms, a Smek protein may be either Smek1 or Smek2. In preferred examples of such embodiments, the compound selectively modulates a Smek1 protein or a Smek2 protein, but not both. In yet other embodiments, the compound may decrease or preferably increase the activity or expression of the Smek protein of interest. In some embodiments, the increase in activity or expression of a Smek protein is due to enhanced transcription, enhanced translation, enhanced phosphorylation, or enhanced affinity for the FOXO transcription factor. In various embodiments, the animal may be a vertebrate animal, a mammal, or a human, pig, cow, sheep, horse, cat, dog, chicken, or turkey.

Another aspect of the present invention includes methods of increasing the life span of an animal by administering to the animal a therapeutically effective amount of a Smek protein. In certain embodiments in higher organisms, the Smek protein may be either Smek1 or Smek2. In various embodiments, the animal may be a vertebrate animal, a mammal, or a human, pig, cow, sheep, horse, cat, dog, chicken, or turkey.

Yet another aspect of the present invention is a method of identifying a compound that increases the lifespan of an animal. The method includes contacting an isolated cell that expresses a Smek protein with a compound;

detecting the activity or expression of the Smek protein; and comparing the activity or expression of the Smek protein after contacting and the activity or expression of the Smek protein in the absence of the compound to determine whether the compound increases the activity or expression of the Smek protein thereby increasing lifespan.

In certain embodiments in higher organisms, the Smek protein may be either Smek1 Smek2. In various embodiments, the animal may be a vertebrate animal, a mammal, or a human, pig, cow, sheep, horse, cat, dog, chicken, or turkey. In various other embodiments, the isolated cell may be a prokaryotic cell, a eukaryotic cell, a plant cell, a vertebrate animal cell, a mammal cell, or a human cell, a pig cell, a cow cell, a sheep cell, a horse cell, a cat cell, a dog cell, a chicken cell, a turkey cell, a mouse cell, a rat cell, a hamster cell, a *C. elegans* cell, or a yeast cell. In certain embodiments, the detection may be performed by measuring the level of Smek mRNA, the level of Smek protein, or the level of a Smek-related activity.

In one aspect of the present invention, the above methods may be used to identify a compound that inhibits the activity or expression of the Smek protein by comparing the activity or expression of the Smek protein after contacting and the activity or expression of the Smek protein in the absence of the compound to determine whether the compound inhibits the activity or expression of the Smek protein. Such aspect includes all embodiments of the above methods.

The present invention also includes methods of identifying a compound that increases the lifespan of an animal by enhancing phosphorylation of a Smek protein. The method includes
  contacting an isolated cell that expresses a Smek protein with a compound;
  detecting the phosphorylation level of the Smek protein; and
  comparing the phosphorylation level of the Smek protein after contacting and the phosphorylation level of Smek1 in the absence of the compound to determine whether the compound enhances phosphorylation of the Smek protein.

The above method includes all the above mentioned embodiments.

The present invention further includes methods of identifying a compound that inhibits phosphorylation of a Smek protein. The method includes
  contacting an isolated cell that expresses the Smek protein with a compound;
  detecting the phosphorylation level of the Smek protein; and
  comparing the phosphorylation level of the Smek1 protein after contacting and the phosphorylation level of the Smek protein in the absence of the compound to determine whether the compound inhibits phosphorylation of the Smek protein.

The present invention further includes methods of identifying a compound that bind to a Smek protein. The method includes
  contacting a Smek protein with a compound; and
  measuring binding between the compound and the Smek protein.

The above aspects relating to methods of increasing the life span of an animal and identifying compounds that increase the life span of an animal may also be used to enhance the stress tolerance of an animal and identify compounds that enhance the stress tolerance of an animal in all of the above embodiments and variations.

Another aspect of the present invention includes methods of inhibiting the activity of Smek in a cell. The method includes
  contacting a cell with an antisense or siRNA molecule.

In certain embodiments, the antisense molecule comprises a polynucleotide strand substantially complementary to a region of a Smek gene. In preferred embodiments, the antisense molecule is at least about 75% identical to, at least about 80% identical to, at least about 85% identical to, at least about 90% identical to, at least about 95% identical to, at least about 97% identical to, or is identical to a region of SEQ ID NO: 7, 8, 9, 10, or 11. In yet other embodiments, the region is at least about 15 nucleotides long, at least about 20 nucleotides long, at least about 25 nucleotides long, at least about 30 nucleotides long, at least about 40 nucleotides long, at least about 50 nucleotides long, or at least about 75 nucleotides long. In certain embodiments, the siRNA molecule comprises a first poly nucleotide strand that is at least about 80% identical to, at least about 90% identical to, at least about 95% identical to, or identical to a region of SEQ ID NO: 7, 8, 9, 10, or II and a second polynucleotide strand that is at least about 80% identical to, at least about 90% identical to, at least about 95% identical to, or identical to a nucleotide sequence complementary to the region of SEQ ID NO: 7, 8, 9, 10, or 11, respectively. In various embodiments, the region is at least about 18, at least about 19, at least about 20, at least about 21, at least about 22, or at least about 23 nucleotides long.

One aspect of the present invention includes stress-resistant non-human animals comprising a transcriptional regulatory sequence active in the animal operably linked to a recombinant nucleic acid encoding a Smek protein. In a preferred embodiment, the Smek protein is Smek1. More preferably, the Smek1 protein is at least about 50%, at least about 60%, at least about 70%, at least about 75%, at least about 80%, at least about 85%, at least about 90%, at least about 95%, at least about 97%, at least about 98%, or at least about 99% identical to the sequence shown in SEQ ID NO: 1. In another embodiment, the Smek protein is Smek2. Preferably, the Smek2 protein is at least about 50%, at least about 60%, at least about 70%, at least about 75%, at least about 80%, at least about 85%, at least about 90%, at least about 95%, at least about 97%, at least about 98%, or at least about 99% identical to the sequence shown in SEQ ID NO: 2. In certain embodiments, the animal is a vertebrate animal, a mammal, or a pig, a cow, a sheep, a horse, a cat, a dog, a chicken, or a turkey. In various embodiments, the transcriptional regulatory element may be heterologous to a Smek protein encoding recombinant nucleic acid, and such element may promote constitutive expression, inducible expression or developmentally regulated expression.

Yet another aspect of the claimed invention includes stress-resistant, isolated animal cells comprising a transcriptional regulatory sequence active in the animal cell operably linked to a recombinant nucleic acid encoding a Smek protein. The stress resistant cell includes all of the above variations and embodiments and includes human cells as well.

Another aspect of the present invention covers isolated stress induced animal cells comprising a Smek gene wherein Smek activity or expression is repressed. In various embodiments, the animal cell may be a vertebrate animal, a mammal, or a pig, a cow, a sheep, a horse, a cat, a dog, a chicken, or a turkey cell. In certain embodiments, the Smek gene is the Smek1 gene and more preferred the Smek1 activity is specifically repressed. In certain other embodiments, the Smek gene is the Smek2 gene and more preferred the Smek2 activity is specifically repressed. In preferred embodiments, Smek activity is repressed at least about 10%, at least about 20%, at least about 30%, at least about 40%, at least about 50%, or at least about 75%.

Another aspect of the present invention covers isolated non-stress induced animal cells comprising a Smek gene wherein Smek activity or expression is elevated. In various embodiments, the animal cell may be a vertebrate animal, a mammal, or a human, a pig, a cow, a sheep, a horse, a cat, a dog, a chicken, or a turkey cell. In certain embodiments, the Smek gene is the Smek1 gene and more preferred the Smek1 activity is specifically elevated. In certain other embodiments, the Smek gene is the Smek2 gene and more preferred the Smek2 activity is specifically elevated. In preferred embodiments, Smek activity is elevated at least about 10%, at least about 20%, at least about 30%, at least about 50%, at least about 75%, at least about 100%, at least about 150%, at least about 250%, or at least about 500% above the normal level of activity.

In one embodiment, the present invention includes a Smek protein or a nucleic acid molecule encoding a Smek protein. In a preferred embodiment, the Smek protein has the amino acid sequence set forth in SEQ ID NO: 1, 2, 3, 4, 5 or 6 or a conservative variant of the sequence shown in SEQ ID NO: 1, 2, 3, 4, 5 or 6. In another preferred embodiment, the nucleic acid molecule has the sequence shown in SEQ ID NO: 7, 8, 9, 10, or 11 or homologous sequence to the sequence shown in SEQ ID NO: 7, 8, 9, 10, or 110. In certain embodiments, Smek protein is at least about 50%, at least about 60%, at least about 70%, at least about 75%, at least about 80%, at least about 85%, at least about 90%, at least about 95%, at least about 97%, at least about 98%, or at least about 99% identical to the sequence shown in SEQ ID NO: 1, 2, 3, 4, 5, or 6. In other embodiments, Smek protein is encoded by a nucleotide sequence that hybridizes to SEQ ID NO: 7, 8, 9, 10, or 11 under very high stringency hybridization, under high stringency hybridization, under moderate stringency hybridization or under low stringency hybridization. In still other embodiments, Smek protein-encoding nucleic acid is at least about 50%, at least about 60%, at least about 70%, at least about 75%, at least about 80%, at least about 85%, at least about 90%, at least about 95%, at least about 97%, at least about 98%, or at least about 99% identical to the sequence shown in SEQ ID NO: 7, 8, 9, 10, or 11.

In another embodiment, the present invention includes the above nucleic acids molecules operably linked to a promoter. In certain embodiments, the promoter may be a constitutive promoter, an inducible promoter, or regulated promoter such as a developmentally regulated, spatially regulated or temporally regulated promoter. In other embodiments, the promoter is functional in animals, in vertebrates, or in mammals. Another embodiment of the present invention includes any of the above nucleic acids in a vector or other genetic construct such as a viral genome.

In still another embodiment, the present invention includes transgenic non-human animals expressing a Smek protein as exemplified above or comprising any of the above nucleic acids, vectors or other constructs. In certain embodiments, the expression of Smek protein may be limited to particular developmental times, or particular tissues, such as during adulthood, or in the white adipose tissue (WAT). In *C. elegans*, the intestine is an essential site of activity of DAF-16 (the FOXO homolog) and the nervous system is crucial site of activity of DAF-2. In mammals, recent experiments show that knockout of the insulin receptor in fat tissue increases longevity and stress resistance. This tissue shares many similarities with the intestines of worms, where fat is stored in this animal. In certain embodiments, the animals may be pigs, cows, sheep, horses, cats, dogs, chickens, or turkeys.

In one embodiment, the present invention is drawn to a method of modulating at least one trait in an animal which includes altering the level or the activity of Smek protein in an animal. In a preferred embodiment, the trait is longevity or stress resistance. In a preferred embodiment, Smek protein has the amino acid sequence set forth in SEQ ID NO. 1, 2, 3, 4, 5, or 6 or a conservative variant of the sequence shown in SEQ ID NO: 1, 2, 3, 4, 5, or 6. In certain embodiments, Smek protein is at least about 50%, at least about 60%, at least about 70%, at least about 75%, at least about 80%, at least about 85%, at least about 90%, at least about 95%, at least about 97%, at least about 50%, or at least about 99% identical to the sequence shown in SEQ ID NO: 1, 2, 3, 4, 5, or 6. In other embodiments, Smek protein is encoded by a nucleotide sequence that hybridizes to SEQ ID NO: 7, 8, 9, 10, or 11 under very high stringency hybridization, under high stringency hybridization, under moderate stringency hybridization or under low stringency hybridization.

In one embodiment, the level of Smek protein is altered by producing an animal having an expression vector having a gene encoding Smek protein. Such animals shall preferably display either the trait of increased longevity or enhanced stress resistance. In a preferred embodiment, the gene encoding Smek protein has a nucleotide sequence that encodes the amino acid sequence set forth in SEQ ID NO. 1, 2, 3, 4, 5, or 6 or a conservative variant of the sequence shown in SEQ ID NO: 1, 2, 3, 4, 5, or 6. In another preferred embodiment, the gene encoding Smek protein has the nucleotide sequence set forth in SEQ ID NO. 7, 8, 9, 10, or 11.

In one embodiment, the present invention is drawn to a method of modulating a Smek-related trait in an animal. The method includes transforming a animal cell with an expression vector including a gene that encodes a Smek protein; and culturing the animal cell into a animal under conditions that allow the expression of the Smek protein thereby modulating a Smek-related trait.

In a preferred embodiment, Smek protein is overexpressed in the animal. In a preferred embodiment, the Smek protein is encoded by a gene including the nucleotide sequence shown in SEQ ID NO: 7, 8, 9, 10, or 11. In another preferred embodiment, Smek protein is encoded by a gene including the nucleotide sequence shown in SEQ ID NO: 7, 8, 9, 10, or 11. In one preferred embodiment, the expression vector includes a constitutive promoter. In an alternate preferred embodiment, the expression vector includes an inducible promoter. In yet another embodiment, the expression vector includes a developmentally regulated promoter. Each of the foregoing promoters is operably linked to a Smek gene. In certain embodiments, the promoter may be heterologous including, without limitation, promoters from the same organism but a different gene and promoters from different organisms. In certain embodiments, the transgenic overexpression or modified expression is achieved by operably linking a heterologous promoter to an endogenous Smek protein gene.

In another aspect, the above described nucleic acids and vectors are overexpressed in a cell. Preferably, the animal or animal cell is a pig, cow, sheep, horse, cat, dog, chicken, or turkey or a cell derived from the foregoing. In some preferred embodiments of methods not involving a whole transgenic animal, the animal or animal cell is a human or a human cell.

In a preferred embodiment, the Smek-related trait is a trait selected from the group including: longevity, stress resistance, affinity for FOXO, transcription of stress related genes, and phosphorylation of the Smek protein. In a more preferred embodiment, the Smek-related trait is longevity, and the longevity is increased.

In one embodiment, the present invention is drawn to a method of modulating a Smek-related trait in an animal which includes contacting an animal cell, or animal, with an inhibitor or activator of a Smek gene such that expression of the Smek gene is reduced or increased, respectively, compared to an animal not contacted with the inhibitor or activator. Preferably, a Smek gene includes the nucleotide sequence shown in SEQ ID NO: 7, 8, 9, 10, or 11. In another preferred embodiment, a Smek gene includes the nucleotide sequence shown in 7, 8, 9, 10, or 11.

In a preferred embodiment, the inhibitor includes an expression vector expressing a protein, an antisense nucleic acid molecule or an siRNA that inhibits expression of a Smek gene. In yet another preferred embodiment, the inhibitor is an siRNA molecule or an antisense nucleic acid molecule directed to a Smek gene, the p38γ MAP kinase gene, or the p38δ MAP kinase gene.

In a preferred embodiment, the Smek-related trait is a trait selected from the group including longevity, stress resistance, affinity for FOXO, transcription of stress related genes, and phosphorylation of the Smek protein. In a more preferred embodiment, the Smek-related trait is longevity, and said longevity is increased. In certain embodiments, the longevity is increased at least about 10%, at least about 20%, at least about 30%, at least about 40%, at least about 50%, at least about 75%, at least about 100%, at least about 150%, at least about 2000%, at least about 300%, or at least about 500%.

In one aspect, the present invention is drawn to a transgenic animal having at least one modulated Smek-related trait as compared to a non-transgenic animal, wherein the transgenic animal includes a recombinant expression vector that expresses a nucleic acid encoding a Smek gene. In a preferred embodiment, a Smek gene is overexpressed. In a preferred embodiment, a Smek gene includes the nucleotide sequence shown in SEQ ID NO: 7, 8, 9, 10 or 11. In a preferred embodiment, the expression vector includes a constitutive promoter. In an alternate preferred embodiment, the expression vector includes an inducible promoter. In another preferred embodiment, the expression vector includes a developmentally regulated promoter. In each of the foregoing, the promoter is operably linked to a Smek gene.

In a preferred embodiment, the Smek-related trait in the transgenic animal is a trait selected from the group including: longevity, stress resistance, affinity for FOXO, transcription of stress related genes, and phosphorylation of the Smek protein. In a more preferred embodiment, the Smek-related trait is longevity, and said longevity is increased.

In another aspect, the present invention includes methods of generating recombinant nucleic acid molecules encoding a Smek protein as well as the recombinant nucleic acid molecules produced from such methods. The method includes providing genetic material from an animal and isolating from the nuclear material the nucleic acid molecule encoding a Smek protein. In various embodiments, the genetic material may be genomic DNA, RNA, cDNA generated from an animal. In certain embodiments, the genetic material is encompassed in a library, which in certain embodiments may be an expression library. In certain embodiments, the animal may be selected from the group including human, pig, cow, sheep, horse, cat, dog, chicken, or turkey. The nucleic acid molecule may be isolated by any method available to one of ordinary skill in the art. In certain embodiments, the nucleic acid molecule is isolated by hybridization to a Smek encoding polynucleotide or fragment thereof. Examples of such isolation include hybridization to amplify the nucleic acid molecule, hybridization to identify the nucleic acid molecule in a library, and hybridization to directly purify the nucleic acid molecule. In another embodiment, the isolation is performed by screening an expression library with an antibody to a Smek protein including without limitation the Smek proteins disclosed herein.

BRIEF DESCRIPTION OF THE DRAWINGS

Figure 1A:
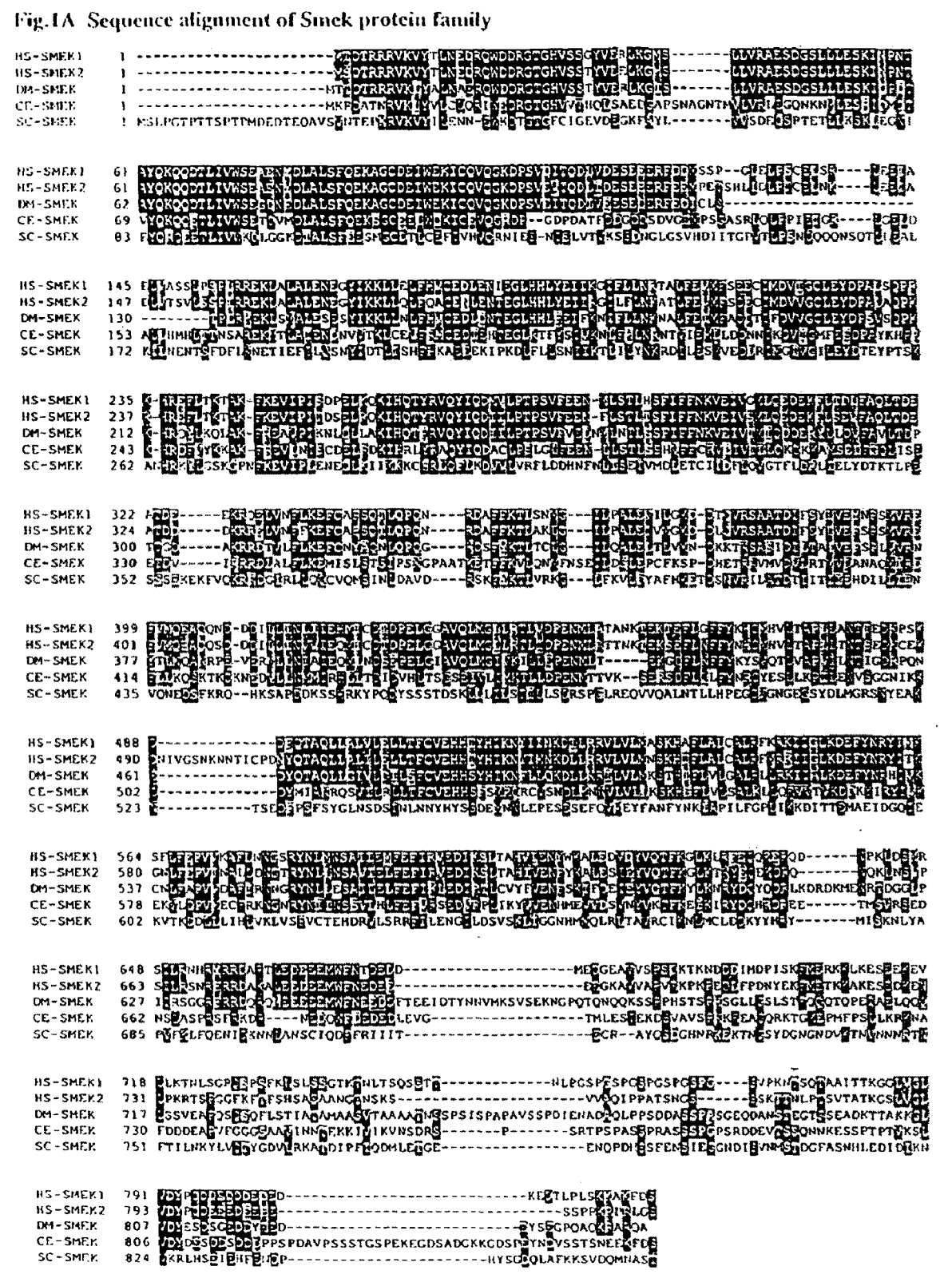

FIG. 1: A) Sequence alignment of Smek orthologs from human, *Drosophila*, *C. elegans* and *S. cerevisiae*. B) Localization of Smek1 and Smek2 in the human genome. C) Domain structure of human Smek1

FIG. 2: Localization of Smek1 isoforms in 293T cells. A) Nuclear localization of GFP-tagged Smek1. B) Immunofluorescence staining of endogenous Smek1. C) Blocking of nuclear staining of Smek1 by antigen. D) Cytoplasmic localization of Smek1-S1-GFP. E) Nuclear translocation of Smek1-S1-GFP after UV stimulation (180 J/m$^2$, 6 hrs). F) Control GFP localization after same UV treatment as in E).

FIG. 3: A) Dose-dependent phosphorylation of Smek1 upon osmotic stress. 293T cells were stimulated with 0.3M and 0.6M sorbitol, respectively, lysed at different time points as indicated, followed by western blot analysis using Smek1 antibodies. B) Dose-dependent phosphorylation of Smek1 after UV treatment. HeLa cells were stimulated with different UV dosages and lysed after incubating for 1 hr at 37 degrees. C) Sustained phosphorylation of Smek1 in response to UV stress. 293T cells were treated with UV (180 J/m$^2$), and cell lysates were collected every hour afterwards for 5 hrs followed by western blot analysis using Smek1 antibodies. D) The phosphorylation of Smek1 induced by stress was abolished by treating anti-Smek1 IPs with potato acid phosphatase (PAP).

FIG. 4: A) Lack of phosphorylation of GST-Smek1 by JNK MAPK in vitro. GST-cJUN was used a positive control for JNK activity. B) phosphorylation of GST-Smek1 by p38 MAPKs in vitro. Flag-tagged p38 MAPK isoforms were transfected into 293T cells, activated by stimulating cells with UV (120 J/m$^2$), and immunoprecipitated using anti-Flag antibodies for in vitro kinase assay. GST-ATF2 was used as a positive control for p38 MAPK activity. The top panel showed the protein levels of different p38 MAPK isoforms in the lysates. The lower panel showed the differential phosphorylation of GST-Smek1 by p38 MAPKs. C) Identification of potential phosphorylation sites of Smek1. Top panel showed the autoradiograph of p38 Kinase assay using GST-Smek and GST-Smek1-5A mutant as substrate, respectively. GST-ATF2 was the positive control, and kinase inactive p38δ-KM and p38γ-AF were negative controls; middle panel showed the protein levels of p38δ and p38γ in cell lysates; the bottom panel showed the predicted p38 MAP kinase phosphorylation sites in Smek1. D) Lack of phosphorylation of Smek1-5A mutant in response to stress in vivo. 293T cells transiently expressing FLAG-tagged Smek1-5A mutant were treated with various stress stimuli as indicated, and cell lysates were analyzed by western blotting in comparison to the wild type controls shown on the left.

FIG. 5: Interaction between Smek1 and FOXO proteins. A) Left panel: 293T cells were transfected with FLAG-Smek1 in the absence or presence of HA-FOXO3a were lysed for immunoprecipitation using anti-FLAG antibodies. The immunoprecipitates were resolved by SDS-PAGE and probed with anti-HA and anti-FLAG antibodies separately to show protein levels in the IPs (top) and lysates (bottom). Right panel: similar experiment was performed with Smek1, FOXO4 and FOXO4-TM mutant. The sample lanes were numbered at the bottom for convenience. B) Left panel: 293T cells were transfected with HA-FOXO3a in the absence or presence of FLAG-Smek1 or Smek1-5A mutant, followed by cell lysis, anti-FLAG immunoprecipitation and western blot analysis using anti-HA antibodies. IgG and α-tubulin were used as controls for protein levels in IPs (top) and lysates (bottom), respectively. Right panel: the same blot was stripped and probed with anti-FLAG antibodies to show Smek1 proteins levels in IPs (top) and lysates (bottom).

FIG. 6: Activation of FOXO3a-driven transcription by Smek1. A) Activation of a synthetic FOXO luciferase reporter by Smek1. HepG2 hepatocytes were transfected with the indicated plasmids with a synthetic luciferase reporter containing three copies of FOXO binding sites (pGL2-3xIRS) and a β-galactosidase reporter construct. Forty hours later cell lysates were collected for luciferase assay and the data were normalized to the value of β-galactosidase activity and presented as a percent of activity of vector control. B) Dosage-dependent activation of FOXO reporter by Smek1. 293 cells were transfected with constitutively active FOXO3a-TM mutant and various amount of Smek1 in the presence of pGL2-3xIRS and a β-galactosidase reporter constructs. The data were normalized to the value of β-galactosidase activity and presented as fold of the activity by expressing FOXO3a-TM alone. C) and D) Activation of native promoters of FOXO target gene by Smek1. Cells were transfected as indicated together with a luciferase reporter driven by the native promoter of FOXO3a target genes, GADD45 and catalase, respectively. The data are shown as a percent of vector control calculated from duplicated samples.

FIG. 7: Working model. The figure shows two signaling pathways: (i) the insulin/IGF-1-PI3K-AKT signaling pathway and (ii) the stress activated pathway represented by the upstream kinase ASK1-downstream p38 MAPK cascade. The two pathways were shown to converge on a protein complex containing Smek1 and FOXO proteins in the nucleus. While AKT phosphorylation negatively regulates Smek1-FOXO interaction by excluding FOXO from the nucleus, stress signaling promotes the Smek1-FOXO interaction via phosphorylation of both Smek1 and FOXO, which represents a balance that exists under physiological circumstances. As a result, the integrated response may be translated into changes in gene expression that are important in stress resistance and life span regulation.

FIGS. 8-13B: Additional Sequences. FIG. 8) shows the predicted *Dictyostelium* (*Dictyostelium discoideum*) Smek 1 protein sequence (SEQ ID NO 26), FIGS. 9A-9B) show the Human Smek1 cDNA sequence (SEQ ID NO 27), FIGS. 10A-10B) show the Human Smek2 cDNA sequence (SEQ ID NO 28), FIGS. 11A-11C) show the predicted *Dictyostelium discoideum* Smek1 cDNA sequence (SEQ ID NO 29), FIGS. 12A-12C) show the *C. elegans* Smek1 cDNA sequence (SEQ ID NO 30), FIGS. 13A-13B) show the *S. cerevisiae* Smek1 cDNA sequence (SEQ ID 31).

FIG. 14A) daf-2 (e1370) long-lived mutant animals. FIG. 14B) N2, wild-type animals. FIG. 14C) isp-1(qm150) long-lived mutant animals. FIG. 14D) Long-lived cyc-1 RNAi (complex III) treated animals. FIG. 14E) daf-16(mu86) null mutant animals. FIG. 14F) glp-1(e2141) long-lived mutant animals. All statistical data for life span analysis can be found in Table 1.

DETAILED DESCRIPTION OF THE PREFERRED EMBODIMENT

Figure 14A:
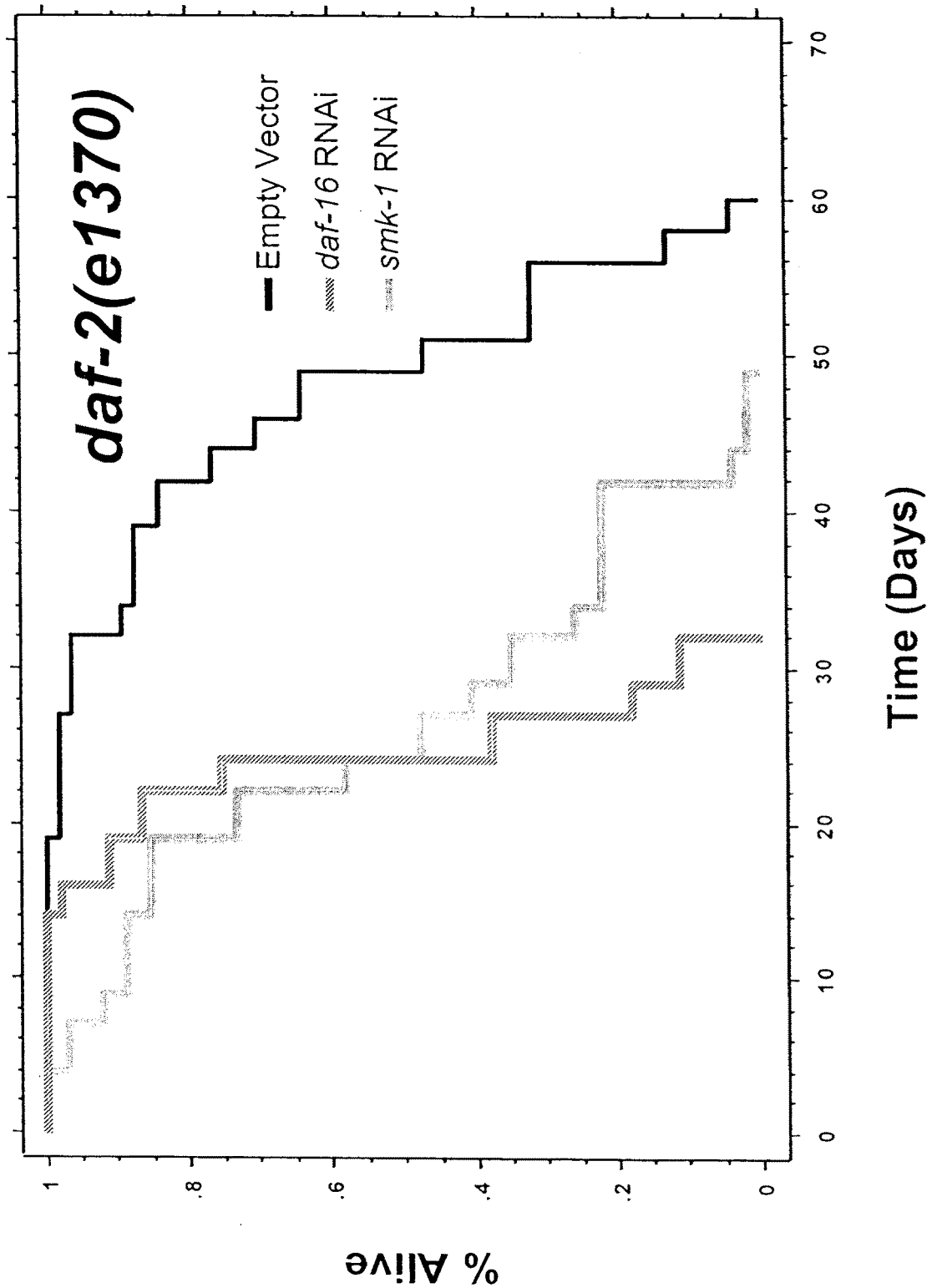
FIGS. 14A-14F. smk-1 is required for the increased longevity of insulin/IGF-1 signaling. In all cases, the solid black line depicts animals grown on bacteria with an empty vector all of their life. The solid grey line depicts animals grown on bacteria producing smk-1 dsRNA. In cases where daf-16 RNAi was required, the cross-hatched line depicts animals grown on bacteria expressing daf-16 RNAi.
Figure 14B:
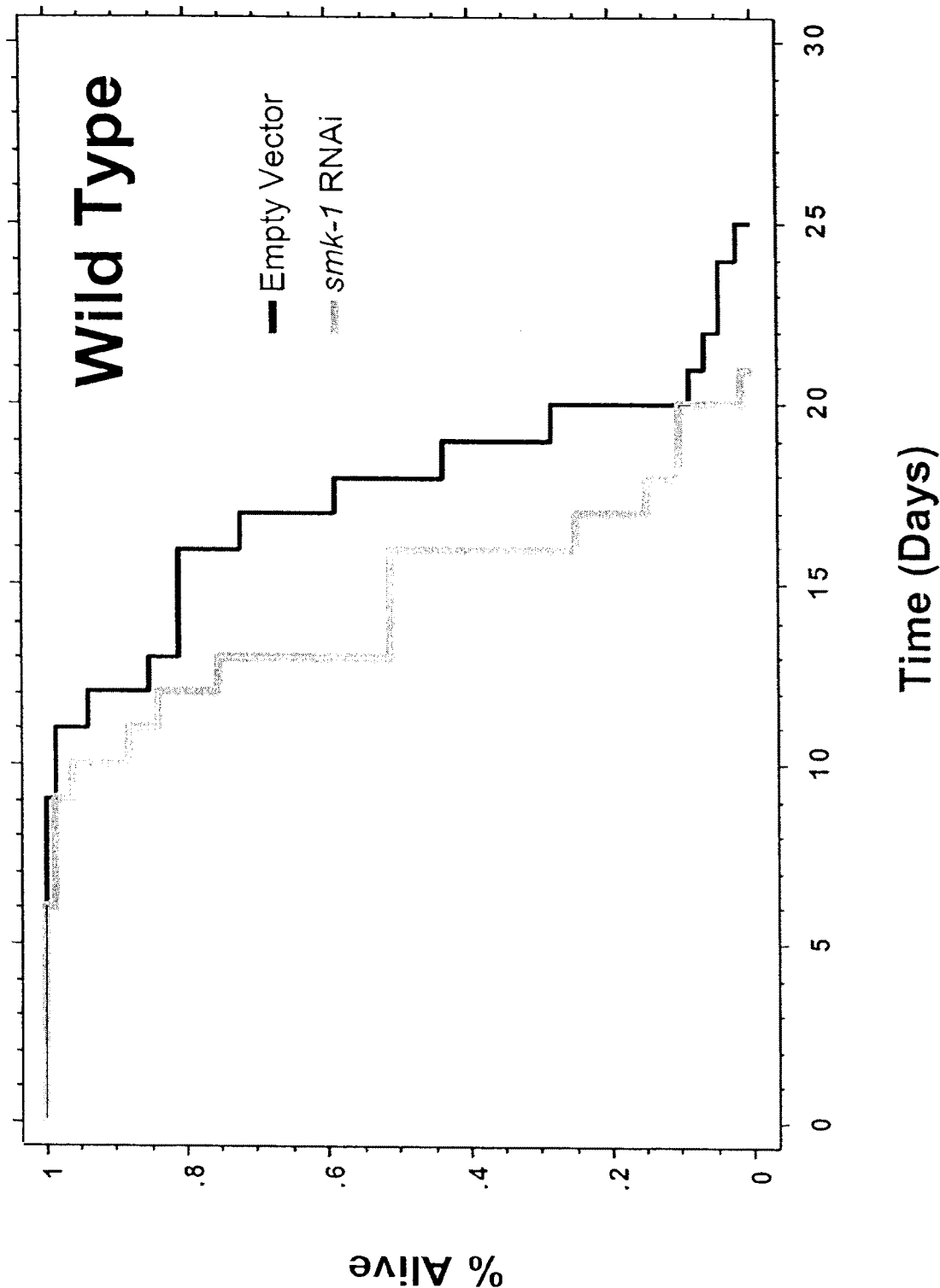
Figure 14C:
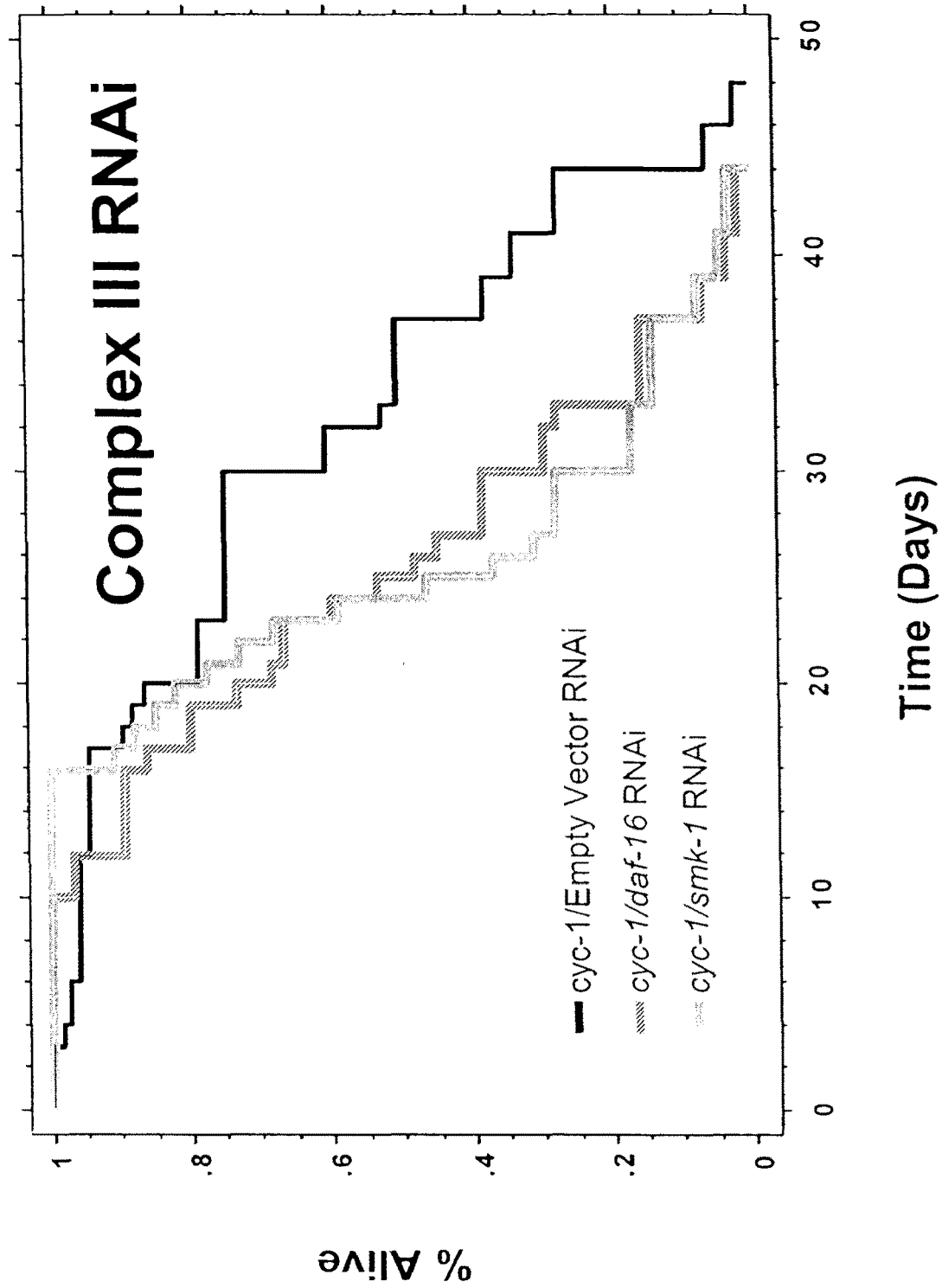
Figure 14D:
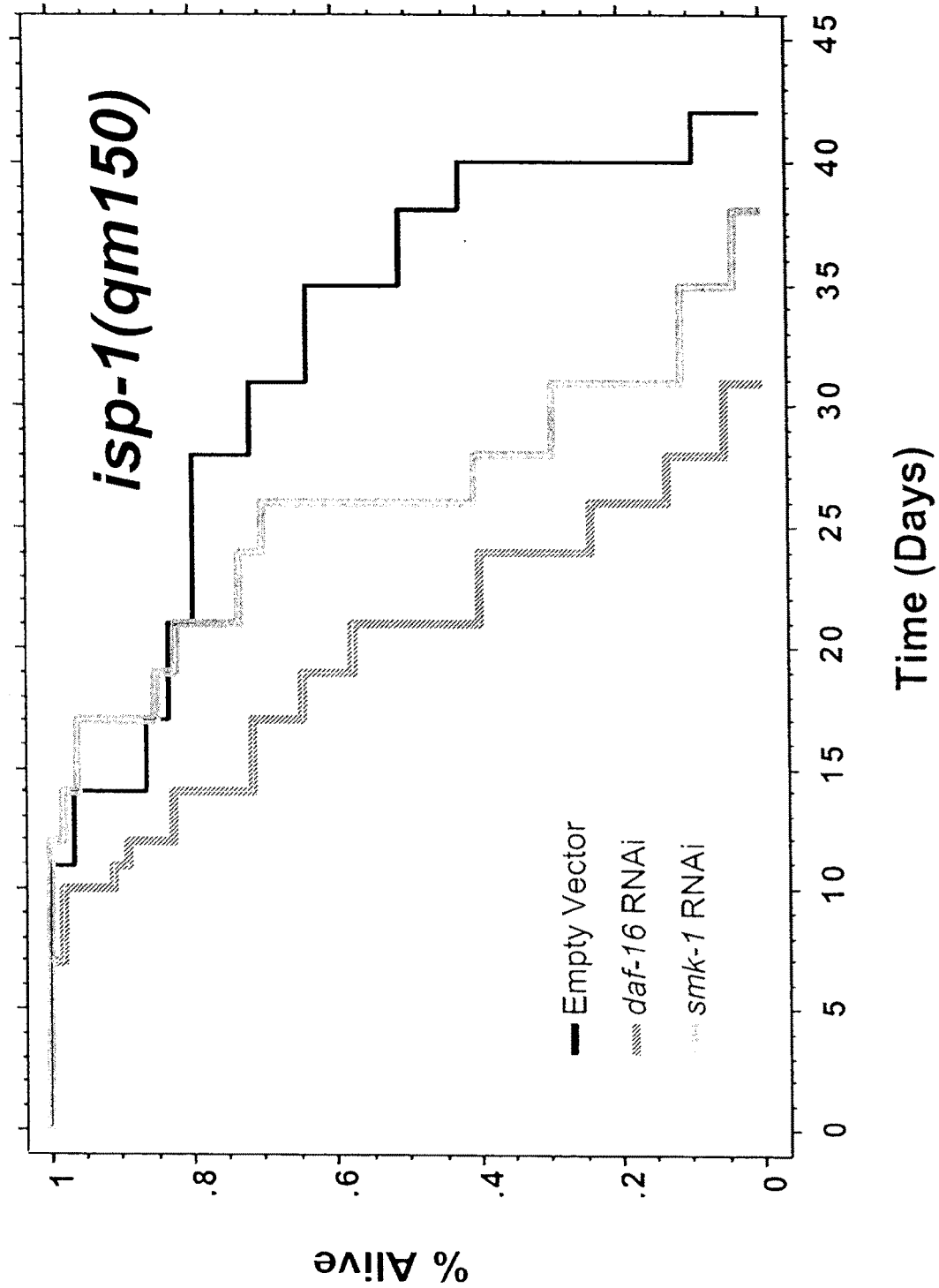
Figure 14E:
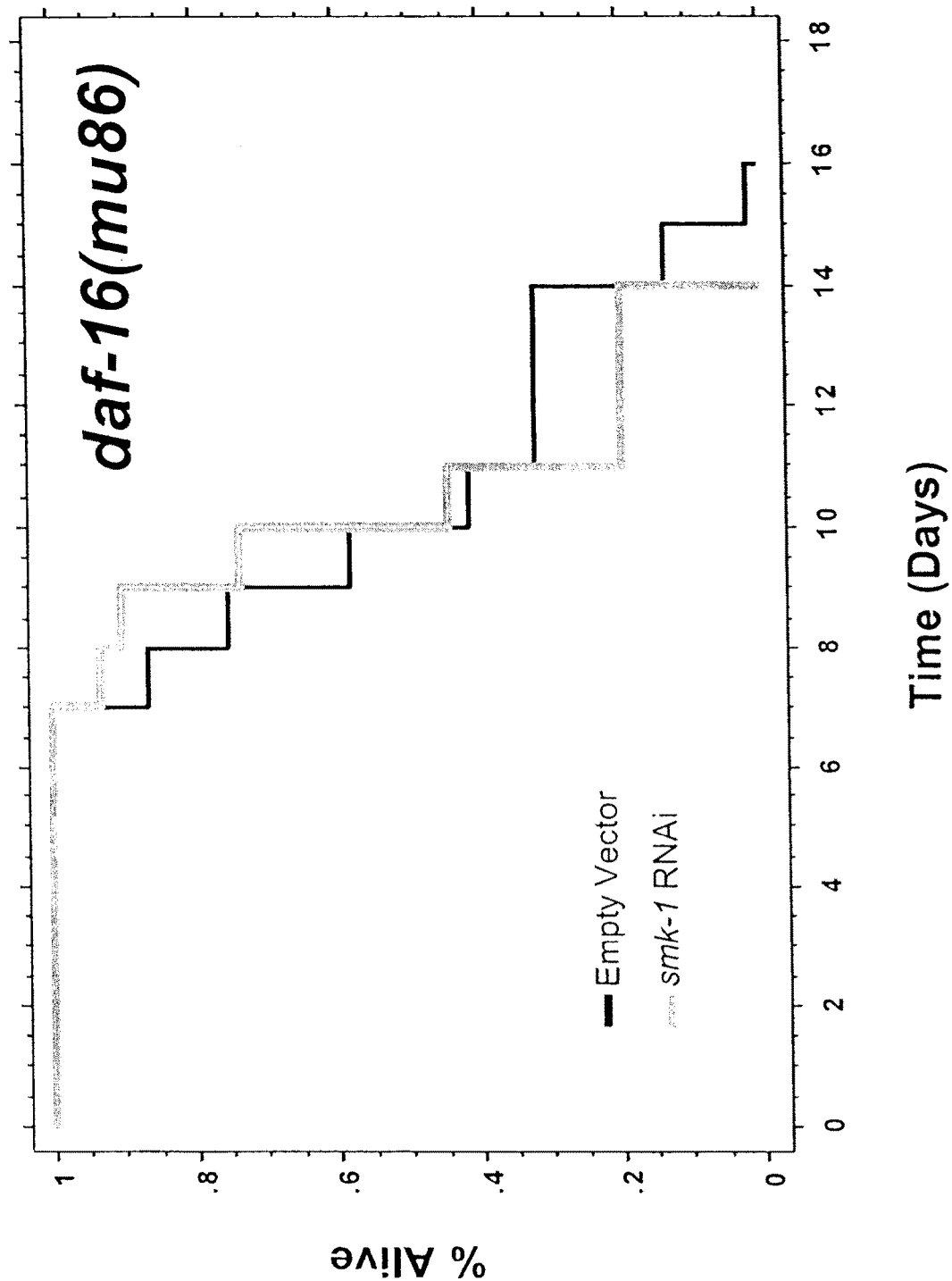
Figure 14F:
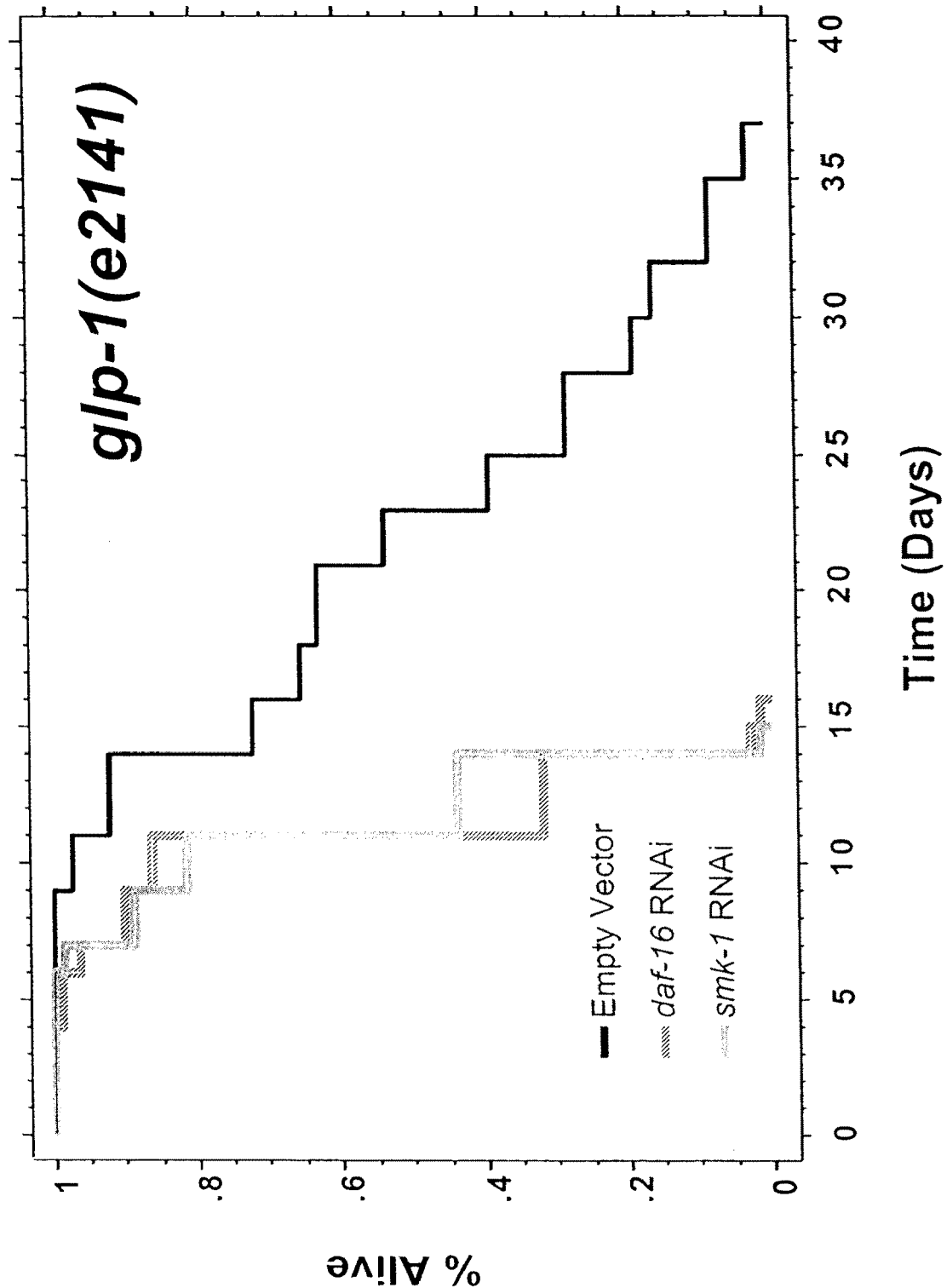

Embodiments of the invention are based, in part, upon the identification of a Smek protein as the link between the stress response pathway and the insulin/IGF signaling pathway. Thus, one embodiment of the invention provides isolated nucleic acids including nucleotide sequences comprising or derived from Smek genes and/or encoding polypeptides comprising or derived from Smek proteins. Smek sequences include the specifically disclosed sequence, and splice variants, allelic variants, synonymous sequences, and homologous or orthologous variants thereof. Thus, for example, embodiments of the invention include genomic and cDNA sequences from a Smek gene.

Embodiments of the invention also include allelic variants and homologous or orthologous sequences. For example, these variants are useful in allele specific hybridization screening or PCR amplification techniques. Moreover, subsets of a Smek sequence, including both sense and antisense sequences, and both normal and mutant sequences, as well as intronic, exonic and untranslated sequences, may be employed for these techniques. Such sequences may comprise a small number of consecutive nucleotides from the sequence disclosed or otherwise enabled herein but preferably include at least 8-10, and more preferably 9-25, consecutive nucleotides from a Smek sequence. Various nucleic acid constructs in which Smek sequences, either complete or subsets, are operably joined to exogenous sequences to form cloning vectors, expression vectors, fusion vectors, transgenic constructs, and the like are also contemplated.

Embodiments of the invention also include functional Smek polypeptides, and functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of Smek polypeptide", refers to all fragments of Smek that retain Smek activity, e.g., ability to confer a modulated Smek-related trait or particular activities of the Smek protein such as the ability to bind to FOXO and the ability to enhance transcription by FOXO. Biologically functional fragments, for example, can vary in size from a polypeptide fragment as small as an epitope capable of binding an antibody molecule to a large polypeptide capable of participating in the characteristic induction or programming of phenotypic changes within a cell. A "Smek-related trait" refers to a trait that is mediated through a Smek protein such as longevity, lifespan and response to stress.

Modifications of a Smek primary amino acid sequence may result in an animal having reduced or abolished, or conversely an enhanced, Smek activity. Such modifications may be deliberate, as by site-directed mutagenesis, or may be spontaneous. All of the polypeptides produced by these modifications are included herein as long as the biological activity of Smek is present. Further, deletion of one or more amino acids can also result in a modification of the structure of the resultant molecule without significantly altering its activity. This can lead to the development of a smaller active molecule which could have broader utility. For example, it may be possible to remove amino or carboxy terminal amino acids without altering Smek activity.

Smek polypeptides include amino acid sequences substantially the same as the sequence set forth in SEQ ID NO: 1, 2, 3, 4, 5, or 6. The term "substantially the same" refers to amino acid sequences that provide nearly the same amino acid sequence, or retain the activity of Smek as described herein. In preferred embodiments, the Smek protein is at least about 50%, at least about 60%, at least about 70%, at least about 75%, at least about 80%, at least about 85%, at least about 90%, at least about 95%, at least about 97%, at least about 98%, or at least about 99% identical to the sequence shown in SEQ ID NO: 1, 2, 3, 4, 5, or 6. Identity may be determined using any of the methods described herein which align the polypeptides or fragments being compared and determines the extent of amino acid identity or similarity between them, e.g., by using the publicly available program BLASTP. It will be appreciated that amino acid "identity" is a comparison of amino acids that are identical between two or more sequences being compared, which is different than homology which includes comparison of amino acids that are identical or are conserved variations. Identity may also be used in the context of polynucleotides, in which case one of skill in the art could use a publicly available program such as BLASTN. The Smek polypeptides of the invention include conservative variations of the polypeptide sequence.

The term "conservative variation" as used herein denotes the replacement of an amino acid residue by another, biologically similar residue. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

FIG. 1A shows the amino acid sequence alignment of several Smek proteins. The sequence alignment shows which regions of the protein are more conserved than the others. In addition, one of skill in the art may perform additional sequence alignments using other known methods. Such sequence alignments provide a good indication of the degree of variation of amino acid residues at any given position that may be tolerated. One of skill in the art would understand that highly conserved regions may be less able to tolerate significant variation and retain functional activity while less conserved regions may be able to tolerate variation and retain functional activity. Also, one of skill in the art will appreciate that where corresponding residues vary between the sequences, such variation gives an indication of the nature of changes that are likely to be tolerated without disturbing the function of the protein.

Smek proteins can be analyzed by standard SDS-PAGE and/or immunoprecipitation analysis and/or Western blot analysis, for example. Embodiments of the invention also provide an isolated polynucleotide sequence encoding a polypeptide having the amino acid sequence of SEQ ID NO: 7, 8, 9, 10, or 11 as well as nucleotide sequence encoding any of the above described Smek proteins. The term "isolated" as used herein includes polynucleotides or polypeptides, as applicable, substantially free of other nucleic acids, proteins, lipids, carbohydrates or other materials with which they are naturally associated. Polynucleotide sequences of the invention include DNA, cDNA and RNA sequences which encode Smek. It is understood that polynucleotides encoding all or varying portions of Smek are included herein, as long as they encode a polypeptide with Smek activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription.

Moreover, Smek polynucleotides include polynucleotides having alterations in the nucleic acid sequence that still encode a polypeptide having the ability to modulate a Smek-related trait such as longevity, lifespan and response to stress. Alterations in Smek nucleic acid include but are not limited to intragenic mutations (e.g., point mutation, nonsense (stop), antisense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Embodiments of the invention also include anti-sense polynucleotide sequences.

The polynucleotides described herein include sequences that are degenerate as a result of the genetic code. There are 20 naturally occurring amino acids, most of which are specified by more than one codon. Therefore, all degenerate nucleotide sequences are included in the invention as long as the amino acid sequence of Smek polypeptide encoded by such nucleotide sequences retains Smek activity A "functional polynucleotide" denotes a polynucleotide which encodes a functional polypeptide as described herein. In addition, embodiments of the invention also include a polynucleotide encoding a polypeptide having the biological activity of an amino acid sequence of SEQ ID NO: 1, 2, 3, 4, 5, or 6 and having at least one epitope for an antibody immunoreactive with Smek polypeptide.

As used herein, the terms "polynucleotides" and "nucleic acid sequences" refer to DNA, RNA and cDNA sequences and include all analogs and backbone substitutes such as PNA that one of skill in the art would recognize as capable of substituting for naturally occurring nucleotides and backbones thereof.

Polynucleotides encoding Smek include the nucleotide sequence of SEQ ID NOS: 7, 8, 9, 10, and 11. cDNA sequences are shown in SEQ ID NO: 7, 8, 9, 10, and 11. Nucleic acid sequences complementary to SEQ ID NOS: 7, 8, 9, 10, and 11 are also encompassed within the present invention. A complementary sequence may include an antisense nucleotide. When the sequence is RNA, the deoxyribonucleotides A, G, C, and T of SEQ ID NOS: 7, 8, 9, 10, or 11 are replaced by ribonucleotides A, G, C, and U, respectively. Also included in the invention are fragments ("probes") of the above-described nucleic acid sequences that are at least 15 bases in length, or preferably at least 16 bases in length, or preferably at least 18 bases in length, or preferably at least 20 bases in length, which is sufficient to permit the probe to selectively hybridize to DNA that encodes the protein of SEQ ID NO: 7, 8, 9, 10, or 11.

"Antisense" nucleic acids are DNA or RNA molecules that are complementary to at least a portion of a specific mRNA molecule (Weintraub, *Scientific American* 262 40, 1990). In the cell, the antisense nucleic acids hybridize to the corresponding mRNA, forming a double-stranded molecule. This interferes with the translation of the mRNA since the cell will not translate a mRNA that is double-stranded. Antisense oligomers of at least about 15 nucleotides are preferred, of at least about 20 nucleotides are preferred, of at least about 25 nucleotides are preferred, of at least about 30 nucleotides are preferred, of at least about 35 nucleotides are preferred, of at least about 40 nucleotides are preferred, or of at least about 50 nucleotides are preferred, since they are easily synthesized and are less likely to cause non-specific interference with translation than larger molecules. The use of antisense methods to inhibit the in vitro translation of genes is well known in the art (Marcus-Sakura *Anal. Biochem.* 172: 289, 1998). In the present case, animals transformed with constructs containing antisense fragments of the Smek gene would display a modulated Smek-related phenotype such as altered longevity.

Short double-stranded RNAs (dsRNAs; typically <30 nt) can be used to silence the expression of target genes in animals and animal cells. Upon introduction, the long dsRNAs enter the RNA interference (RNAi) pathway which involves the production of shorter (20-25 nucleotide) small interfering RNAs (siRNAs) and assembly of the siRNAs into RNA-induced silencing complexes (RISCs). The siRNA strands are then unwound to form activated RISCs, which cleave the target RNA. Double stranded RNA has been shown to be extremely effective in silencing a target RNA. Introduction of double stranded RNA corresponding to the Smek gene would be expected to modify the Smek-related traits discussed herein including, but not limited to, longevity and stress tolerance.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 ng/ml sheared and denatured salmon sperm DNA. Hybridization could occur under medium stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art. "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes SMEK-related sequences from unrelated nucleotide sequences.

In another aspect of the invention, very high stringency hybridization conditions can include at least one wash at 0.1×SSC, 0.1% SDS, at 60° C. for 15 minutes. High stringency hybridization conditions can include at least one wash at 0.2×SSC, 0.1% SDS, at 60° C. for 15 minutes. Moderate stringency hybridization conditions can include at least one wash at 0.5×SSC, 0.1% SDS, at 60° C. for 15 minutes. Low stringency hybridization conditions can include at least one wash at 1.0×SSC, 0.1% SDS, at 60° C. for 15 minutes.

Another aspect of the invention is polypeptides or fragments thereof which have at least about 70%, at least about 80%, at least about 85%, at least about 90%, at least about 95%, or more than about 95% homology to SEQ ID NO: 1, 2, 3, 4, 5, or 6, and sequences substantially identical thereto, or a fragment comprising at least 5, 10, 15, 20, 25, 30, 35, 40, 50, 75, 100, or 150 consecutive amino acids thereof. Homology may be determined using any of the methods described herein which align the polypeptides or fragments being compared and determines the extent of amino acid identity or similarity between them. It will be appreciated that "homology" includes polypeptides having conservative amino acid substitutions such as those described above. "Homolog" includes a gene related to a second gene by descent from a common ancestral DNA sequence. The term, homolog, may apply to the relationship between genes separated by the event of speciation or to the relationship between genes separated by the event of genetic duplication. "Orthologs" are genes in different species that evolved from a common ancestral gene by speciation. Normally, orthologs retain the same function in the course of evolution. Identification of orthologs is critical for reliable prediction of gene function in newly sequenced genomes.

The polypeptides or fragments having homology to SEQ ID NO: 1, 2, 3, 4, 5, or 6, and sequences substantially identical thereto, or a fragment comprising at least about 5, 10, 15, 20, 25, 30, 35, 40, 50, 75, 100, or 150 consecutive amino acids thereof may be obtained by isolating the nucleic acids encoding them using the techniques described herein.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to the polypeptide of SEQ ID NO: 1, 2, 3, 4, 5, or 6, and sequences substantially identical thereto, or a fragment comprising at least about 5, 10, 15, 20, 25, 30, 35, 40, 50, 75, 100, or 150 consecutive amino acids thereof using any of the programs described above.

Also included in embodiments of the invention are nucleotide sequences that are greater than 70% homologous with SEQ ID NOS: 7, 8, 9, 10, or 11, but still retain the ability to modulate a Smek-related trait such as longevity, lifespan and stress tolerance. Other embodiments of the invention include nucleotide sequences that are greater than 75%, 80%, 85%, 90% or 95% homologous with SEQ ID NOS: 7, 8, 9, 10, or 11, but still retain the ability to confer a modulated Smek-related trait which includes altered longevity, lifespan and stress tolerance.

Also included in embodiments of the invention are nucleotide sequences that are greater than 70% identical to SEQ ID NOS: 7, 8, 9, 10, or II, but still retain the ability to modulate a Smek-related trait such as longevity. Other embodiments of the invention include nucleotide sequences that are greater than 75%, 80%, 85%, 90% or 95% identical to SEQ ID NOS: 7, 8, 9, 10, or 11, but still retain the ability to confer a modulated Smek-related trait which includes altered longevity.

Specifically disclosed herein is a cDNA sequence for Smek as well as two genomic DNA sequences. DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Screening procedures which rely on nucleic acid hybridization make it possible to isolate any gene sequence from any organism, provided the appropriate probe is available. Oligonucleotide probes, which correspond to a par of the Smek sequence encoding the protein in question, can be synthesized chemically. This requires that short, oligopeptide stretches of the amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA.

Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9, 879, 1981). Alternatively, a subtractive library is useful for elimination of non-specific cDNA clones.

Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al. *Nucl. Acid Res,* 11, 2325, 1983).

A cDNA expression library, such as lambda gt11, can be screened indirectly for Smek peptides using antibodies specific for Smek. Such antibodies can be either polyclonally or monoclonally derived and used to detect expression product indicative of the presence of Smek cDNA.

Another embodiment of the invention relates to animals that have at least one modulated Smek-related trait. Such modulated traits include among others an altered longevity and an altered stress tolerance, "Longevity" refers to the life span of the animal. Thus, longevity refers to the number of years in the life span of an animal. "Stress tolerance" refers to an animal's ability to tolerate exposure to various internal and external environmental challenges such as exposure to UV light, exposure to high osmolarity, exposure to infection, exposure to oxidative damage, exposure to metal compounds, and exposure to certain toxins. Those of skill in the art will recognize that an increase in the lifespan of an animal can readily be measured by various assays known in the art. The field of gerontology is one such example of a relevant art. By way of example, longevity may be assessed by various markers such as number of generations to senescence in non-immortalized somatic cells, graying hair, wrinkling, and other such alterations physiological markers associated with aging. Those of skill in the art will also recognize that alterations in an animals ability to tolerate stress, i.e., its response to stress, may be assessed by various assays, including by way of example, by assessing changes in expression or activity of molecules involved in the stress response by measuring expression of stress response genes, protein levels of specific stress response proteins, or activity levels of specific stress response proteins.

Animals having a modified Smek-related trait include transgenic animals with an altered longevity or an altered stress tolerance due to transformation with constructs using antisense or siRNA technology that affect transcription or expression from a Smek gene. Such animals exhibit an altered longevity (or life span) and an altered stress tolerance.

Accordingly, in another series of embodiments, the present invention provides methods of screening or identifying proteins, small molecules or other compounds which are capable of inducing or inhibiting the activity or expression of Smek genes and proteins. The assays may be performed, by way of example, in vitro using transformed or non-transformed cells, immortalized cell lines, or in vivo using transformed animal models enabled herein. An example of a preferred animal model would be a transgenic mouse with one or both of the endogenous Smek genes replaced with the corresponding human Smek genes. In particular, the assays may detect, for example, the presence of increased or decreased activity or expression of Smek (from human or other animal) genes or proteins on the basis of increased or decreased mRNA expression, increased or decreased levels of Smek protein products, or increased or decreased levels of expression of a marker gene (e.g., beta-galactosidase, green fluorescent protein, alkaline phosphatase or luciferase) operably joined to an Smek 5' regulatory region in a recombinant construct, increased or decreased phosphorylation of the Smek protein, increased or decreased affinity for FOXO proteins. Cells known to express a particular Smek, or transformed to express a particular Smek, are incubated and one or more test compounds are added to the medium under conditions in which Smek nucleic acid or protein is know to be modulated. In addition, in higher organisms with at least two Smek genes, such as humans, compounds that selectively induce or inhibit the activity or expression of one Smek protein and not another may be identified in such assays. Such assays could, for example, use pairs of cell-lines, each only expressing one such Smek gene and comparing the effect of the compound on each cell-line. After allowing a sufficient period of time (e.g., 0-72 hours) for the compound to induce or inhibit the activity or expression of Smek, any change in levels of activity or expression from an established baseline may be detected using any of the techniques described above.

In another series of embodiments, the present invention provides methods for identifying proteins and other compounds which bind to, or otherwise directly interact with Smek protein. The proteins and compounds include endogenous cellular components which interact with Smek in vivo and which, therefore, provide new targets for therapeutic or diagnostic products, as well as recombinant, synthetic and otherwise exogenous compounds which may have Smek binding capacity and, therefore, are candidates for modulating Smek-related traits. In addition, in higher organisms with at least two Smek proteins, such as humans, compounds that selectively bind to one protein and not the other may be identified in such assays. Such assays could use parallel or sequential binding assays against the two proteins. Thus, in one series of embodiments, High Throughput Screening-derived proteins, DNA chip arrays, cell lysates or tissue homogenates may be screened for proteins or other compounds which bind to one of the normal or mutant Smek genes. Alternatively, any of a variety of exogenous compounds, both naturally occurring and/or synthetic (e.g., libraries of small molecules or peptides), may be screened for Smek binding capacity.

In each of these embodiments, an assay is conducted to detect binding between Smek and another moiety. Smek in these assays may be any polypeptide comprising or derived from a normal or mutant Smek protein, including functional domains or antigenic determinants of Smek. Binding may be detected by non-specific measures (e.g., transcription modulation, altered chromatin structure, peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of Smek components and bound proteins or other compounds by immunoprecipitation; (3) BIAcore analysis; and (4) the yeast two-hybrid systems.

Embodiments of the invention also include methods of identifying proteins, small molecules and other compounds capable of modulating the activity of normal or mutant Smek. Using normal cells or animals, the transformed cells and animal models of the present invention, or cells obtained from subjects bearing normal or mutant Smek genes, the present invention provides methods of identifying such compounds on the basis of their ability to affect the expression of Smek, the activity of Smek, the activity of other Smek-regulated genes, the activity of proteins, such as FOXO, that interact with normal or mutant Smek proteins, the intracellular localization of Smek, changes in transcription activity, the presence or levels of membrane bound Smek, the level of phosphorylation of Smek, or other biochemical, histological, or physiological markers which distinguish cells bearing normal and modulated Smek activity in animals.

In accordance with another aspect of the invention, the proteins of the invention can be used as starting points for rational chemical design to provide ligands or other types of small chemical molecules. Alternatively, small molecules or other compounds identified by the above-described screening assays may serve as "lead compounds" in design of modulators of Smek-related traits in animals.

DNA sequences encoding Smek can be expressed in vitro by DNA transfer into a suitable host cell. "Host cells" are cells in which a vector can be propagated and its DNA expressed. The term also includes any progeny or graft material, for example, of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

As part of the present invention, Smek polynucleotide sequences may be inserted into a recombinant expression vector. The terms "recombinant expression vector" or "expression vector" refer to a plasmid, virus or other vehicle known in the art that has been manipulated by insertion or incorporation of a Smek genetic sequence. Such expression vectors contain a promoter sequence which facilitates the efficient transcription of the inserted Smek sequence. The expression vector typically contains an origin of replication, a promoter, as well as specific genes which allow phenotypic selection of the transformed cells.

Methods which are well known to those skilled in the art can be used to construct expression vectors containing Smek coding sequence and appropriate transcriptional/translational control signals. These methods include in vitro recombinant DNA techniques, synthetic techniques, and in vivo recombination/genetic techniques.

A variety of host-expression vector systems may be utilized to express a Smek coding sequence. These include but are not limited to microorganisms such as bacteria transformed with recombinant bacteriophage DNA, plasmid DNA or cosmid DNA expression vectors containing a Smek coding sequence; yeast transformed with recombinant yeast expression vectors containing a Smek coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing a Smek coding sequence; insect cell systems infected with recombinant virus expression vectors (e.g., baculovirus) containing a Smek coding sequence; or animal cell systems infected with recombinant virus expression vectors (e.g., retroviruses, adenovirus, vaccinia virus) containing a Smek coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al. *Methods in Enzymology* 153, 516-544, 1987). For example, when cloning in bacterial systems, inducible promoters such as pL of bacteriophage 7, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted Smek coding sequence.

Isolation and purification of recombinantly expressed polypeptide, or fragments thereof, may be carried out by conventional means including preparative chromatography and immunological separations involving monoclonal or polyclonal antibodies. In addition, the recombinantly expressed polypeptide, of fragments thereof, may include an affinity tag, such as a FLAG-tag, a his-tag, a GST or MBP fusion. Such affinity tags may be preferable when the polypeptide is to be used in identification of compounds that bind to Smek or modulate the activity of Smek owing to the ease of manipulation.

In another embodiment of the invention provide a method for producing a genetically modified non-human animal having at least one modulated Smek-related trait such as having an altered longevity as compared to an animal which has not been genetically modified. One of skill in the art will recognize that a Smek-related traits such as longevity and stress tolerance may vary from individual to individual, so the average over several individuals in a population needs to be determined when comparing such traits. The method includes the steps of contacting an animal cell with at least one vector containing at least one nucleic acid sequence encoding a Smek gene or a mutant, homolog or fragment thereof, wherein the nucleic acid sequence is operably associated with a promoter or a transcriptional regulatory element, to obtain a transformed animal cell; producing a transgenic animal from the transformed animal cell; and thereafter selecting an animal exhibiting a modulated Smek-related trait such as an altered longevity. One of skill in the art will appreciate that the present invention also includes transgenic modulation of endogenous Smek gene expression by introducing a heterologous promoter or transcriptional regulatory element into the genome of an animal such that the promoter or element is operably linked to the Smek gene.

Transgenic animals that result in at least one modulated Smek-related trait such as an altered longevity may be obtained by reduced expression of the Smek gene. Thus, one embodiment of the invention includes animals transformed with antisense polynucleotides complementary to a Smek gene or fragments thereof wherein production of the antisense polynucleotides results in reduced expression of the Smek gene. In an alternate embodiment, reduced expression of Smek may also be achieved by methods such as expression of siRNAs targeting a Smek gene by operatively linking an siRNA gene to a promoter. In an alternate embodiment, transgenic animals overexpressing a Smek gene are described.

Such animals might be expected to display a modulated Smek-related trait such as an altered longevity, lifespan, or stress tolerance.

The term "genetic modification" as used herein refers to the introduction of one or more heterologous nucleic acid sequences, e.g., a Smek sequence or a Smek mutant encoding sequence, into one or more animal cells, which can generate whole, adult animal by nuclear transplantation or pronuclear injection into an embryo or oocyte and implantation of such embryo or oocyte into the uterus of a host animal. The term "genetically modified" as used herein refers to an animal which has been generated through the aforementioned process. Genetically modified animals of the invention are capable of interbreeding with other animals of the same species so that the foreign gene, carried in the germ line, can be inserted into or bred into agriculturally useful animal varieties. The term "animal cell" as used herein refers to immortalized cell lines, embryonic stem cells, and non-immortalized cell lines. Accordingly, an embryo comprising multiple animal cells capable of developing to term into an adult animal, is included in the definition of "animal cell".

As used herein, the term "animal" refers to either a whole animal, an animal organ, an animal cell, or a group of animal cells, such as an animal tissue, for example, depending upon the context. Animals included in the invention are any animals amenable to transformation techniques, including vertebrate and non-vertebrate animals and mammals. Examples of mammals include, but are not limited to, pigs, cows, sheep, horses, cats, dogs, chickens, or turkeys.

The term "exogenous nucleic acid sequence" as used herein refers to a nucleic acid foreign to the recipient animal host or, native to the host if the native nucleic acid is substantially modified from its original form. For example, the term includes a nucleic acid originating in the host species, where such sequence is operably linked to a promoter that differs from the natural or wild-type promoter. In one embodiment, at least one nucleic acid sequence encoding Smek or a variant thereof is operably linked with a promoter. It may be desirable to introduce more than one copy of a Smek polynucleotide into an animal for enhanced expression. For example, multiple copies of the gene would have the effect of increasing production of the Smek gene product in the animal.

Genetically modified animals of the present invention are produced by contacting an animal cell with a vector including at least one nucleic acid sequence encoding a Smek or a variant thereof. To be effective once introduced into animal cells, a Smek nucleic acid sequence is operably associated with a promoter which is effective in the animal cell to cause transcription of Smek. Additionally, a polyadenylation sequence or transcription control sequence, also recognized in animal cells may also be employed. It is preferred that the vector harboring the nucleic acid sequence to be inserted also contain one or more selectable marker genes so that the transformed cells can be selected from non-transformed cells in culture, as described herein.

The term "operably linked" refers to functional linkage between a promoter sequence and a nucleic acid sequence regulated by the promoter. The operably linked promoter controls the expression of the nucleic acid sequence.

The expression of structural genes may be driven by a number of promoters. Although the endogenous, or native promoter of a structural gene of interest may be utilized for transcriptional regulation of the gene, preferably, the promoter is a foreign regulatory sequence. For mammalian expression vectors, promoters capable of directing expression of the nucleic acid preferentially in a particular cell type may be used (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the α-fetoprotein promoter (Campes and Tilghman, 1989. Genes Dev. 3: 537-546).

Promoters useful in the invention include both natural constitutive and inducible promoters as well as engineered promoters. To be most useful, an inducible promoter should 1) provide low expression in the absence of the inducer; 2) provide high expression in the presence of the inducer; 3) use an induction scheme that does not interfere with the normal physiology of the animal; and 4) have no effect on the expression of other genes. Examples of inducible promoters useful in animals include those induced by chemical means, such as the yeast metallothionein promoter which is activated by copper ions (Mett, et al. Proc. Natl. Acad. Sci., U.S.A. 90, 4567, 1993); and the GRE regulatory sequences which are induced by glucocorticoids (Schena, et al. Proc. Natl. Acad. Sci., U.S.A. 88, 10421, 1991). Other promoters, both constitutive and inducible will be known to those of skill in the art.

The particular promoter selected should be capable of causing sufficient expression to result in the production of an effective amount of structural gene product to modulate a Smek-related trait such as longevity. The promoters used in the vector constructs of the present invention may be modified, if desired, to affect their control characteristics.

Optionally, a selectable marker may be associated with the nucleic acid sequence to be inserted. As used herein, the term "marker" refers to a gene encoding a trait or a phenotype which permits the selection of, or the screening for, an animal or animal cell containing the marker. Preferably, the marker gene is an antibiotic resistance gene whereby the appropriate antibiotic can be used to select for transformed cells from among cells that are not transformed. Suitable markers will be known to those of skill in the art.

Vector(s) employed in the present invention for transformation of a animal cell include a nucleic acid sequence encoding Smek, operably linked to a promoter. To commence a transformation process in accordance with the present invention, it is first necessary to construct a suitable vector and properly introduce it into the animal cell. Details of the construction of vectors utilized herein are known to those skilled in the art of animal genetic engineering.

A transgenic animal of the present invention can be created by introducing Smek protein-encoding nucleic acid into the male pronuclei of a fertilized oocyte (e.g., by microinjection, retroviral infection) and allowing the oocyte to develop in a pseudopregnant female foster animal. Sequences including SEQ ID NO: 7, 8, 9, 10, or 11 can be introduced as a transgene into the genome of a non-human animal. Alternatively, a non-human homolog of the human Smek gene, such as a mouse Smek1 gene, can be isolated based on hybridization to the human Smek1 gene and used as a transgene. Intronic sequences and polyadenylation signals can also be included in the transgene to increase the efficiency of expression of the transgene. A tissue-specific regulatory sequence(s) can be operably-linked to the Smek transgene to direct expression of Smek protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: Manipulating the Mouse Embryo, Cold Spring Harbor Laboratory Press, Cold Spring Harbor, N.Y. Similar methods are used for production of other transgenic animals. A transgenic founder animal can be identified based upon the presence of the Smek transgene in its genome and/or expression of Smek mRNA in tissues or cells of the animals. A transgenic founder animal can then be used to breed additional animals carrying the transgene. Moreover, transgenic animals carrying a transgene-encoding Smek protein can further be bred to other transgenic animals carrying other transgenes.

To create a homologous recombinant animal, a vector is prepared which contains at least a portion of a Smek gene into which a deletion, addition or substitution has been introduced to thereby alter, e.g., functionally disrupt, the Smek gene. The Smek gene can be a human gene (e.g., the DNA of SEQ ID NO: 7 or 8), but may also be a non-human homolog of a human Smek gene. For example, a mouse homolog of the human Smek1 gene or Smek2 gene of SEQ ID NO: 7 or 8 can be used to construct a homologous recombination vector suitable for altering an endogenous Smek gene in the mouse genome. In one embodiment, the vector is designed such that, upon homologous recombination, the endogenous Smek gene is functionally disrupted (i.e., no longer encodes a functional protein; also referred to as a "knock out" vector).

Alternatively, the vector can be designed such that, upon homologous recombination, the endogenous Smek gene is mutated or otherwise altered but still encodes functional protein (e.g., the upstream regulatory region can be altered to thereby alter the expression of the endogenous Smek protein). In the homologous recombination vector, the altered portion of the Smek gene is flanked at its 5'- and 3'-termini by additional nucleic acid of the Smek gene to allow for homologous recombination to occur between the exogenous Smek gene carried by the vector and an endogenous Smek gene in an embryonic stem cell. The additional flanking Smek nucleic acid is of sufficient length for successful homologous recombination with the endogenous gene. Typically, several kilobases of flanking DNA (both at the 5'- and 3'-termini) are included in the vector. See, e.g., Thomas, et al., 1987. Cell 51: 503 for a description of homologous recombination vectors. The vector is then introduced into an embryonic stem cell line (e.g., by electroporation) and cells in which the introduced Smek gene has homologously-recombined with the endogenous Smek gene are selected. See, e.g., Li, et al., 1992. Cell 69: 915.

The selected cells are then injected into a blastocyst of an animal (e.g., a mouse) to form aggregation chimeras. See, e.g., Bradley, 1987. In: Teratocarcinomas and Embryonic Stem Cells: A Practical Approach, Robertson, ed. IRL, Oxford, pp. 113-152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described further in Bradley, 1991. Curr. Opin. Biotechnol. 2: 823-829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. Proc. Natl. Acad. Sci. USA 89: 6232-6236. Another example of a recombinase system is the FLP recombinase system of Saccharomyces cerevisiae. See, O'Gorman, et al., 1991. Science 251:1351-1355. If a Cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. Nature 385: 810-813. In brief, a cell (e.g., a somatic cell) from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell (e.g., the somatic cell) is isolated As used herein, the term "contacting" refers to any means of introducing Smek into an animal cell, including chemical and physical means as described above.

Transgenic animals exhibiting a modulated Smek-related trait such as an increased life span or an enhanced stress tolerance as compared with non-transgenic animals can be selected by observation. While life span varies from animal to animal the average life span can be observed by averaging the life span of several examples of the animal. Stress tolerance can be measured by exposing an animal to various levels of stress and measuring the response, and comparing to the stress response in non-transgenic animals. The invention includes animal produced by the method of the invention, as well as animal tissues and animal cells.

In yet another embodiment, the invention provides a method for producing a genetically modified animal cell such that an animal produced from the cell has a modulated Smek-related trait such as an increased life span compared with a non-transgenic animal. The method includes contacting the animal cell with an Smek nucleic acid sequence to obtain a transformed animal cell; transferring the nucleus of the transformed animal cell into an oocyte; implanting the oocyte into the uterus of an animal and allowing the transgenic animal to develop to term to obtain a transgenic animal having a modulated Smek-related trait such as an increased life span.

It will be understood by those of skill in the art that numerous and various modifications can be made without departing from the spirit of the present invention. A more complete understanding can be obtained by reference to the following specific examples which are provided herein for purposes of illustration only and are not intended to limit the scope of the invention.

EXAMPLES

The following examples include the characterization of a novel protein Smek1 (Suppressor of mek null), which belongs to a protein family conserved among eukaryotic organisms from yeast to mammals. The examples reveal that Smek1 is a nuclear target for a p38 MAP kinase-related stress response pathway in mammalian cells. To define the biological function of Smek1, RNAi in C. elegans was used to deplete the single Smek1 homolog. This analysis indicated that worm Smek1 plays a role in regulating stress resistance and organismal longevity (See Example 6). Since Smek1 appears to function in parallel to the FOXO homolog Daf-16, the key regulator of stress resistance and longevity (Kenyon 2001) and Smek1 binds to FOXO in mammalian cells as demonstrated below, Smek1 and FOXO function as a complex. Example 4 demonstrated that Smek1 indeed interacts with forkhead transcription factors (FOXOs) in mammalian cells.

The following examples further indicate that Smek1 is regulated by phosphorylation in response to stress, while FOXO proteins are well-defined downstream targets for Akt kinase, which has been shown to inhibit transcriptional activity of FOXO by causing its cytoplasmic retention upon phosphorylation (Brunet, Bonni et al. 1999). Interestingly, Example 2 indicates that stress-induced phosphorylation of Smek1 and phosphorylation of FOXO via insulin-PI3K-Akt pathway play an opposing role in regulating Smek1-FOXO interaction, showing the molecular mechanism for the stress response pathway and insulin/IGF-1 signaling pathway to crosstalk and counteract one another in relevant biological processes. Furthermore, Example 5 shows that Smek1 is able to regulate gene expression in part by promoting FOXO-driven transcription. Thus, a protein complex containing Smek1 and FOXO arose during evolution to serve as a nodal point to integrate signals from insulin/IGF-1 pathway and stress response pathway, and perhaps other signaling pathways. Consequently the status of this complex in turn determines the relevant gene expression output that underlies physiological phenomena such as aging. Thus, the present invention focuses on the Smek protein as a target for modulation of aging and other important physiological phenomena.

Finally, the examples include genetic analysis that indicates that loss of smk-1 specifically influences the aging related function of the DAF-2 Insulin/IGF-1 signaling pathway. Localization analysis of DAF-16 places SMK-1 downstream of DAF-16's phosphorylation-dependent relocation to the nucleus, transcriptional assays indicate that SMK-1 is required for maximal DAF-16/FOXO3a transcription, and physiological evidence suggests that DAF-16 and SMK-1 are capable of functional interaction in the nuclei of intestinal cells and neurons. Taken together, the examples indicate that SMK-1 is a new component of the Insulin/IGF-1 signaling longevity pathway, and the first that plays a role in longevity without affecting other processes regulated by Insulin/IGF-1 signaling, presumably by modulating DAF-16 transcriptional specificity.

Example 1

Smek Belongs to a Conserved Novel Protein Family

Smek (suppressor of mek1 null) was identified from Dictyostelium in a second site suppressor screen in a null strain background defective in the MAP kinase DdMEK1. Loss of DdSmek partially suppressed the chemotaxis and developmental defects of Dictyostelium mek1 null cells (unpublished data). Based on the results of Genbank database searches, the Smek orthologs comprise a novel gene family conserved in diverse eukaryotic organisms including yeast, fly, worm, plant and mammals (FIG. 1A). There are two Smek genes in the human genome (Smek1 and Smek2), which are localized on the chromosome 14 and chromosome 2, respectively (FIG. 1B). In addition, an intron-less pseudogene was identified on the X chromosome, which does not have any matching EST clones.

Human Smek1 is composed of 820 amino acid residues. Similar to other Smek homologs, the only region of Smek1 that shares significant homology to any identified protein domain is the N-terminal region (approximately residues 1-100) EVH1 domain, a domain known to bind proline-rich sequences (Volkman, Prehoda et al. 2002) (FIG. 1C). The central region of Smek1 (approximately residues 200-600) is highly hydrophobic and contains a novel domain DUF625 (Domain of Unidentified Function), which appears to be conserved only among Smek orthologs. The C-terminal region of Smek1 is rich in charged residues and is more divergent among Smek homologs. According to the diverse sources of EST clones in the database, human Smek1, as well as Smek2, are widely expressed in various tissues, including brain, liver, pancreas, kidney, testis, ovary and breast. Furthermore, multiple Smek1 EST sequences were identified to contain stop codons within the junction of central and C-terminal domains, demonstrating that Smek1 transcripts are regulated by alternative splicing.

Example 2

SMEK1 is a Stress Response Protein

First, the localization of Smek1 in the cell was investigated by transiently expressing a C-terminal GFP tagged full-length Smek1 in cultured mammalian cells, which revealed that Smek1 is localized in the nucleus (FIG. 2A). This observation was confirmed by immunofluorescence staining of the endogenous protein using an affinity-purified antiserum raised against Smek1 (FIG. 2B). The nuclear staining of Smek1 antibody was effectively blocked by incubating the serum with corresponding antigen (FIG. 2C). Interestingly, the GFP fusion of a natural Smek1 isoform with a truncated C-terminus (Smek1-S1) localized exclusively in the cytoplasm (FIG. 2D), indicating the presence of potential NLS (nuclear localization signal) within the C-terminus.

The conditions under which cytoplasmic Smek1-S1 can translocate into the nucleus were identified. Various conditions were tested with cultured mammalian cell lines expressing a GFP-tagged Smek1-S1, including serum starvation, growth factor stimulation, stress treatments and variations of glucose concentrations in the medium. These experiments revealed that when cells were exposed to a high dose of UV irradiation, Smek1-S1 was translocated into the nucleus (FIG. 2E), demonstrating that Smek1 proteins are involved in the stress response pathway. Similar nuclear translocation of Smek1-S1 was observed in cells treated with high osmolarity (data not shown).

Given that full length Smek1 contains multiple potential phosphorylation sites, especially a cluster of five Serine-Proline (SP) sites in the C-terminal region, Smek1 is regulated by phosphorylation, in particular by stress-activated MAP kinases. Western blot analysis anti-Smek1 antibodies showed that a slower mobility band was induced by treating cells with high osmolarity or UV irradiation (FIG. 3A, B). The effect of potato acid phosphatase treatment confirmed that the mobility shift was caused by phosphorylation induced by sorbitol treatment (FIG. 3D). Further experiments showed that Smek1 phosphorylation could be induced by various stress stimuli besides UV and sorbitol, including inhibitors of protein synthesis, MMS, $H_2O_2$ and IL-1 (data not shown). However, it was not triggered by the stimulation of the Fas death receptor using anti-Fas antibody, or by certain DNA-damaging reagents including etoposide, hydroxy urea and γ irradiation. In order to identify the protein kinase(s) responsible for the stress-induced phosphorylation of Smek1, various kinase inhibitors were tested, including SB203580, U0126, PD98059, wortmannin and rapamycin. However, none of these abolished the stress induced phosphorylation.

Example 3

Smek1 is a Substrate for p38 MAP Kinases

The stress-induced phosphorylation of Smek1 is sustained rather than transient (FIG. 3C), which is similar to the kinetics of stress-activated MAP kinases including the JNK and p38 MAP kinase families (Chang and Karin 2001). To determine whether Smek1 can be phosphorylated by JNK MAP kinase, GST-Smek1 fusion protein was purified from bacteria and tested as a substrate in an in vitro kinase assay with immunoprecipitated JNK. The results indicated that Smek1 was not phosphorylated by JNK in vitro, although the positive control GST-cJun was strongly phosphorylated by JNK (FIG. 4A). Furthermore, the phosphorylation pattern of Smek1 was not altered in jnk1−/−jnk2−/− double knockout MEF cells (data not shown), suggesting that other stress kinases were involved. The lack of inhibition of Smek1 phosphorylation by SB203580, which blocks p38α and p38β activation, suggests that neither are essential; however, the other two p38 isoforms, p38γ and p38δ, are insensitive to SB203580. To test whether p38γ and p38δ could be the kinases responsible for Smek1 phosphorylation, immunoprecipitated p38 isoforms were analyzed in kinase assays using GST-Smek1 as a substrate. The results from this study indicated that Smek1 was differentially phosphorylated by p38 MAP kinases (FIG. 4B). It is clear that p38δ had highest activity towards GST-Smek1 among the four p38 isoforms, whereas p38γ showed modest activity. In contrast, p38α and β only caused minor phosphorylation of GST-Smek1 compared to the positive control GST-ATF2, which is consistent with the lack of effect of SB203580 in vivo. To confirm that the observed phosphorylation of GST-Smek1 was not due to a co-precipitated kinase, p38γ and p38δ mutants lacking kinase activity (p38γ-AF and p38δ-KM) were tested and as expected, these mutant proteins did not cause detectable phosphorylation of GST-Smek1 (FIG. 4C).

The serine residues within the SP cluster of Smek1 are the major phosphorylation sites by a stress-activated kinase in vivo. Based on visual examination of Smek1 sequence, the cluster of five consecutive SP sites in the C-terminal region of Smek1 conform to the consensus phosphorylation sites for p38 MAP kinases. To prove these were the major phosphorylation sites, a mutant Smek1 containing five Serine to Alanine mutations was created using site-directed mutagenesis. In the kinase assay, GST fusion of the mutant protein (GST-Smek1-5A) showed dramatically decreased phosphorylation by p38δ and p38γ compared to wildtype Smek1 (FIG. 4C). Furthermore, when FLAG-tagged Smek1-5A was expressed in mammalian cells, no mobility shift was observed in response to various stress stimuli (FIG. 4D).

Example 4

Smek1 Interacts with FOXO Transcription Factors

Experiments depleting the single Smek1 homolog in C. elegans using RNAi demonstrated that the worm Smek1 homolog plays a role in regulating stress resistance and organismal longevity (See Example 6). The similar physiological role of Smek1 and FOXO homolog Daf16 suggested that they might function within a complex. Flag-tagged Smek1 and HA-tagged FOXO3a or FOXO4 were co-expressed in 293T cells, and both FOXO3a and FOXO4 were detected in immunoprecipitates containing Smek1 (FIG. 5A, lane 3 and 4). Similarly Smek1 was also detected in the immunoprecipitates of FOXO3a. To investigate the effect of stress-induced phosphorylation of Smek1 on Smek1-FOXO interaction, we co-expressed FOXO3a with wildtype Smek1 and mutant Smek1 (Smek1-5A), respectively, and analyzed their interactions by co-immunoprecipitation and western blotting. The results from this experiment showed that Smek1 mutant lacking the phosphorylation sites had significantly weaker affinity for FOXO3a (FIG. 5B, left panel), suggesting that stress signaling might promote Smek1-FOXO interaction. The difference in FOXO binding is not due to differences in expression level or localization, as similar amounts of FOXO3a, Smek1 and Smek1/5A proteins were detected in cell lysates and immunoprecipitates by western blot analysis (FIG. 5B). In addition, Smek1-5A is still localized in the nucleus.

FOXO proteins are well-known downstream target for the insulin/IGF-1-PI3K-Akt pathway. The phosphorylation of FOXOs by Akt has been shown to cause cytoplasmic retention of FOXOs through 14-3-3 binding, thereby inhibiting the transcriptional activity of FOXOs (Brunet, Bonni et al. 1999). To determine whether the phosphorylation via Akt negatively regulates the interaction between Smek1 and FOXO, wildtype FOXO4 and a mutant FOXO4 lacking the three Akt phosphorylation sites (FOXO4-TM), were co-expressed with Smek1 in 293T cells for immunoprecipitation analysis. The results indicated that FOXO4-TM bound Smek1 several times more strongly than wildtype FOXO4, although both proteins were expressed at similar levels (FIG. 5A, lane 4 and 5). As FOXO4-TM is constitutively nuclear, this observation raises the possibility that Smek1 and FOXO might interact in the nucleus.

Example 5

Smek1 Promotes FOXO-Driven Transcription

Smek1 plays a role in regulating FOXO-driven transcription. Co-expression of Smek1 and FOXO3a with luciferase reporters for FOXO proteins in mammalian cells demonstrated the effects of Smek1 on transcription by FOXO. First, the activity of FOXO3a towards a synthetic reporter containing three FOXO binding sites (pGL2-3xIRS-luc) in the absence or presence of Smek1 in HepG2 hepatocytes was tested. The data showed that Smek1 alone did not activate transcription of the synthetic reporter transcription. However, it promoted FOXO-driven transcription when co-expressed with either FOXO3a or FOXO3a-TM (FIG. 6A). Different levels of Smek1 protein were tested in the reporter assay to further analyze the transcriptional activation by Smek1. The increase in FOXO-mediated transcription correlated with the amount of Smek1 co-expressed with FOXO3a-TM (FIG. 6B). Co-expression of Smek1 consistently resulted in robust activation of gene expression driven by FOXO3a mutant lacking the Akt phosphorylation sites, which is consistent with its stronger interaction with Smek1.

Further, Smek1 acts on luciferase reporters driven by a native promoter of FOXO target genes. The reporters for two genes involved in the cellular protective response, GADD45 and catalase, were tested. The results showed that Smek1 by itself caused a modest activation of pGADD45-luc reporter and a strong activation of catalase promoter, which might result from its activation of endogenous FOXO (FIG. 6C). Furthermore, co-expression of Smek1 and FOXO3a led to synergistic activation of both reporter gene transcription (FIG. 6C). In the case of catalase reporter, the enhanced transcription is not observed with a dominant negative FOXO3a mutant consisting of only the DNA binding domain, FOXO3a-DB (Dijkers, Birkenkamp et al. 2002) (FIG. 6D), suggesting that FOXO3a activation domain is required for the effect.

Example 6

C. elegans RNAi Depletion of the Worm Smek1 Homolog

In worms, the single Smek1 homolog is most highly conserved with the human Smek1. Both have a nuclear localization sequence at the C-terminus, an EVH1 domain required for protein interactions and a conserved domain, DUF625, whose function is unknown. Also conserved is a short amino stretch at the C-terminus that resembles a DNA binding domain. Given the homology, several experiments involving depletion of the Smek1 homology in C. elegans using RNAi were conducted to further elucidate the role of Smek1.

To confirm the link between Smek1 in the regulation of daf-16 (the worm homolog of FOXO), Smek1 was depleted, using RNAi, in long-lived daf-2(e1370) mutant animals, completely suppressing the long life span of the mutant animals when compared to non-mutant animals. This demonstrated that Smek1 was an essential component of insulin/IGF-1 signaling in the worm. In fact, lower Smek1 activity reduced the long lifespan of daf-2(e1370) mutant animals to the same extent as did RNAi directed towards daf-16. Furthermore, wild type animals treated with Smek1 RNAi demonstrated a moderate reduction of lifespan. This reduced lifespan was similar to daf-16 RNAi treated animals, or daf-16(mu86) null mutant animals.

To further confirm the link, Smek1 was depleted in daf-16 (mu86) mutant animals. As expected, unlike wild type animals, reduced Smek1 activity did not reduce the lifespan of daf-16 null mutant animals.

Smek1 is specific to the insulin/IGF-1 signaling pathway. Because lower Smek1 gene activity results in reduced longevity, demonstration of specificity to the insulin/IGF-1 signaling pathway requires demonstration that reduced Smek1 activity does not result in a general decline of longevity in all long-lived mutant animals. Besides the insulin/IGF-1 pathway, RNAi or mutation of components of the mitochondrial electron transport chain (ETC) increases longevity. In contrast to the insulin/IGF-1 pathway, the ETC pathway is required during larval development and does not depend upon daf-6 for increased longevity. Three ETC pathway mutants were tested with Smek1 depletion: cyc-1 RNAi (complex III component), isp-1(qm150) or clk-1(qm30) animals. In all three cases, Smek1 was not required for the long lifespan of animals with compromised complex III activity, cyc-1 RNAi treated, isp-1(qm150) mutant animals. Smek1 RNAi also did not suppress the long lifespan of clk-1 mutant animals, which have defects in mitochondrial ubiquinone synthesis. Therefore, reduced Smek1 gene function does not cause a general sickness that results in reduced longevity.

Taken together, three pieces of data indicate that Smek1 is an essential component of the insulin/IGF-1 pathway to regulate the aging process in worms. One, reduced Smek1 activity completely suppresses the long lifespan of daf-2(e1370) mutant animals. Two, reduced Smek1 activity did not further shorten the lifespan of daf-16(mu86) null mutant animals, but did decrease the longevity of wild type animals, much like daf-16 mutations do. Three, much like daf-16, Smek1 is not required for the long lifespan cause by altered mitochondrial activity.

Smek1 does not act by regulation of nuclear entry of daf-16 (the worm FOXO homolog). In wild-type animals, daf-16 is predominantly in the cytoplasm due to inhibitory phosphorylation of serine and threonine residues by the akt and sgk kinases. However, in daf-2 long-lived mutant animals, daf-16 accumulates in the nucleus due to the lack of inhibitory phosphorylation. Using a complementing DAF-16::GFP fusion protein, wild type animals treated with daf-2 RNAi readily accumulated DAF-16 within nuclei, Animals treated with daf-2 and Smek1 RNAi simultaneously also accumulated DAF-16 in the nuclei of many cells, similar to animals treated with an equally diluted cocktail of daf-2 and control plasmid RNAi. Therefore, DAF-16 can still enter the nucleus of cells with reduced Smek1 activity in response to lower insulin/IGF-1 signaling daf-2. However, the increased nuclear entry of DAF-16 in the absence of Smek1 does not result an increased lifespan. Therefore, much like results of Lin et. al, nuclear entry of daf-16 is not sufficient to confer increased longevity of worms.

Smek1 does play an important role in the transcriptional activation of daf-16 target genes. sod-3, a well characterized daf-16 regulated gene, required Smek1 activity for expression. In all cases, reduced Smek1 activity abolished the normally robust sod-3::GFP reporter expression in response to lower daf-2 activity. In fact, reduced Smek1 activity resulted in comparable loss of SOD-3::GFP expression when compared to animals with reduced daf-16 activity.

Collectively, the data obtained from depletion of Smek1 in C. elegans confirmed that Smek1 is an essential co-factor of daf-16 (FOXO) and the combined action of both Smek1 and daf-16 is required for the proper transcriptional activation of daf-16 target genes.

As discussed above, longevity and stress resistance are highly correlated as are longevity and the insulin/IGF-1 pathway. Smek1 provides an essential link between the pathways as demonstrated above. Furthermore, additional RNAi depletion experiments further confirm this essential role of Smek1. Wild type or daf-2(e1370) mutant animals treated with Smek1 were not sensitive to heat stress indicating the Smek1 does not play a role in thermotolerance. Smek1 is, however, essential for other stress resistance pathways. For example, wild type animals or daf-2(e1370) mutant animals with reduced Smek1 activity were sensitive to UV and oxidative stresses, such as paraquat. Furthermore, Smek1 is required for innate immunity, since reduced Smek1 activity resulted in wild type or daf-2(e1370) mutant animals that were more sensitive to *Pseudomonas* Aeurogis infection compared to control animals. Therefore, it is interesting to note that daf-2 (e1370) mutant animals treated with Smek1 RNAi are resistant to heat stress, but are not long-lived or resistance to oxidative stress or infection, indicating that the longevity conferred by lower insulin/IGF-1 signaling may depend more on resistance to oxidation and infection, rather than heat.

Finally, the insulin/IGF-1 pathway in worms independently regulates dauer development, reproductive timing and longevity. But Smek1 is not required for DAF-16's dauer development and reproduction functions. Reduced Smek1 activity did not alter dauer development or reproductive timing. Wild-type animals treated with Smek1 RNAi did not enter dauer diapuase at 25° C. and daf-2(e1370) mutant animals treated with Smek1 RNAi arrested as dauers at 25° C. Additionally, daf-2(e1370) mutant animals still paused for 24 hours during the L2 larval stage when treated with Smek1 RNAI, but not when treated with daf-16 RNAI. Thus indicating that Smek1 does not play a role in dauer development. Further, reduced Smek1 activity in either wild type or daf-2 (e1370) mutant animals did not affect reproduction. For example, wild type animals with reduced Smek1 activity reproduced at the same rate as animals on control bacteria and daf-2(e1370) mutant animals had a protracted reproductive schedule that was nearly identical to daf-2(1370) mutant animals treated with Smek1 RNAi. Thus, consistent with previous studies, the insulin/IGF-1 pathway can be diverged to regulate the timing of reproduction independently of longevity. Taken together, Smek1 appears to be a unique factor that is solely required for DAF-16's longevity function and is not required for the dauer developmental or reproductive functions of DAF-16. Thus, Smek appears to be an ideal target for modulation for affecting longevity given that its association with FOXO is necessary for longevity but not for FOXO's other roles. Thus modulation of Smek1 is less likely to have negative side effects than other genes known to be involved in longevity such as FOXO.

Example 7

Further Characterization of smk-1

Sequence and ontogenetic analysis links SMK-1 with cell cycle progression and carbohydrate metabolism, two processes regulated by insulin signaling and FOXO activity in mammals. RNAi against smk-1 results in phenotypes that include embryonic lethality, slow growth, and protruding vulvas, suggesting that smk-1, like daf->6, is important for development during the embryonic and reproductive stages of the worm life cycle (Kamath et al., 2003; Simmer et al., 2003). smk-1 shares 74% amino acid homology with human and mouse SMEK-1 (FIG. 1).

Several functional motifs are conserved between SMK-1 and the mammalian SMEK-1, including an EVH1 domain at the N-terminus, a conserved domain of unknown function (DUF625) in the central region and a third conserved region (CR3) near the C-terminus. SMK-1 additionally contains conserved LXXLL (LDALL) and LLXXL (LLSTL) motifs (LLINL and LLRTL in human and mouse SMEK-1). These motifs are used by mammalian transcriptional co-activators, such as PGC-1α and p300/CBP, to bind to either PPAR-γ, a nuclear hormone receptor, or the forkhead transcription factor, FOXO1 (Puigserver et al., 2003; Puigserver and Spiegelman, 2003).

Example 8 smk-1 is Expressed in the Nuclei of Intestinal and Neuronal Cells in Adult Worms We examined the timing and localization of SMK-1 within wild-type animals. Using a gfp tagged smk-1 cDNA construct under the control of the endogenous smk-1 promoter to create a stable transgenic line, we observed strong nuclear localization of SMK-1-GFP in intestinal cells. GFP fluorescence was also detected in the nuclei of several hypodermal cells, in many neurons in the head and tail, and in the intestinal cells of developing larvae. The GFP signal was reduced upon treatment with smk-1 RNAi with the most pronounce reduction in the intestinal cells. Endogenous SMK-1 could also be detected in the nuclei of intestinal cells by staining with affinity-purified SMK-1 antibodies. The timing and localization of SMK-1 expression in worms was consistent with the known developmental phenotypes of smk-1 caused by RNAi treatment. Importantly, these assays indicated that SMK-1 was temporally and spatially co-localized with active DAF-16, which is active in transcribing genes when expressed in the nuclei of these cells (Libina et al., 2003).

Example 9 smk-1 is Required for daf-16 Dependent Regulation of Longevity

In addition to its role in innate immunity (Garsin et al., 2003), daf-16 regulates genes necessary for daf-2 dependent longevity in worms. Using RNAi against smk-1, we tested whether smk-1, like daf-16, was required for the extension of dof-2 mutant lifespan. Reduced levels of smk-1 completely suppressed the extended longevity of daf-2(e1370) mutant animals (FIG. 9A, Table 1). However, snik-1 RNAi only moderately shortened the lifespan of wild-type worms (FIG. 9B, Table 1). The level of lifespan suppression in wild-type animals treated with smk-1 RNAi was similar to the reduced life spans observed in daf-16 RNAi treated animals or in daf-16(mu86) null mutant animals (Dillin et al., 2002a; Lin et al., 2001) (FIG. 9E, Table 1).

Because reduced smk-1 gene activity suppressed the extended lifespan of daf-2 mutant animals, we tested whether smk-1 RNAi was acting specifically on the insulin/IGF-1 pathway or whether it caused a general decline in longevity in all long-lived mutant animals. Mutation or reduced expression of components of the mitochondrial electron transport chain increases longevity independently of daf-16 activity (Dillin et al., 2002b; Feng, 2001; Lee et al., 2003b). smk-1 was tested to determine whether smk-1 was required for the increased longevity of isp-1(qm150), clk-1(qm30) mutants, or animals treated with cyc-1 RNAi (complex III component). We found that smk-1 RNAi only slightly suppressed the extended lifespans of the animals with compromised complex III activity, i.e., the cyc-1 RNAi-treated animals and isp-1(qm150) mutant animals (FIGS. 9C and 9D, respectively, and Table 1). Additionally, smk-1 RNAi did not fully suppress the long lifespan of clk-1(qm30) mutant animals (Table 1), which have defects in mitochondrial ubiquinone synthesis (Jonassen et al., 2001; Miyadera et al., 2001). In each of these experiments, smk-1 RNAi-treated animals lived as long or longer than the same animals treated with daf-16

RNAi. smk-1's dispensability for pathways that work independently of daf-16 activity confirms that smk-1 RNAi does not cause a general sickness in long-lived animals but rather specifically affects insulin/IGF-1 signaling(IIS)-regulated lifespan.

To further define the role of smk-1 in IIS, smk-1 was tested to determine whether the function of smk-1 was coincident with or separable from the requirements for daf-16 in DAF-2 pathway mediated longevity. Smk-1 was first tested to determine whether smk-1 reduced the lifespan of daf-16(mu86) mutant animals. Unlike its effects on wild-type animals, reduced smk-1 activity did not reduce the lifespan of daf-16 null mutant animals (Table 1). This result indicated that the requirement for smk-1 in the regulation of longevity in wild-type animals is coincident with the requirement for daf-16.

The overlapping function of smk-1 with daf-16 in wild-type animals suggests that smk-1 might be required for daf-16 dependent increases in longevity mediated by other mechanisms. Because daf-16 is essential for the extended lifespan observed in wild-type animals lacking a germline (Hsin and Kenyon, 1999), we asked whether genetically germline-ablated animals would show a reduction in lifespan when treated with smk-1 RNAi. Using glp-1(e2141) mutant animals that lack germline cells at the non-permissive temperature (25° C.), we found that these long-lived mutant animals required smk-1 for their increased longevity (FIG. 9F, Table 1). smk-1 RNAi suppressed the long lifespan of glp-1 mutant animals to the same extent as daf-16 RNAi. Together, these results indicate that smk-1 cannot act independently from daf-16 in wild-type animals and that smk-1 is required for both known forms of daf-16 dependent longevity.

Taken together, four pieces of data indicate that smk-1 is an essential component of the insulin/IGF-1 pathway that regulates the aging process in worms: 1) Reduced smk-1 activity completely suppressed the long lifespan of daf-2(e1370) mutant animals; 2)) smk-1 is not required for the long lifespan caused by altered mitochondrial activity; 3) Reduced smk-1 activity did not further shorten the lifespan of daf-16(mu86) null mutant animals, but did decrease longevity modestly in wild-type animals; 4) Reduced smk-1 activity completely suppressed the increased longevity due to loss of the germline.

Example 10 smk-1 is not a Transcriptional Target of DAF-16

One possible mechanism by which smk-1 could be required for DAF-16 dependent longevity is that smk-1 is a transcriptional target of DAF-16. Recently, through microarray analysis, several transcriptional targets of DAF-16 have been identified and found to be physiologically relevant for DAF-16-mediated longevity (Murphy et al, 2003). smk-1 was examined to determine whether it could be a transcriptional target of DAF-16 required for longevity in worms using quantitative real time PCR (Q-PCR); wild-type worms treated with daf-16 RNAi did not exhibit reduced levels of smk-1 mRNA compared to worms treated with empty vector RNAi. smk-1 mRNA levels were significantly diminished in worms treated with smk-1 RNAi, confirming the specificity and penetrance of the RNAi construct. Moreover, smk-1 and its mammalian homologue have not appeared as DAF-16/FOXO3a dependent genes in microarrays and screens identifying genes differentially regulated during the aging process (McCarroll et al., 2004; McElwee et al., 2004; Murphy et al., 2003). Additionally, despite the relative abundance of short consensus binding sites for DAF-16 within the complete *C. elegans* genome, no DAF-16 binding sites are present within the smk-1 promoter (the 2.0 kb promoter region upstream of the smk-1 coding sequence) or within the first intron of smk-1. Finally, fluorescence levels of our smk-1::gfp overexpression lines did not appear visibly reduced upon treatment with daf-16 RNAi. These data suggest that smk-1 is not directly or indirectly transcriptionally regulated by DAF-16.

Example 11 daf-16 is not a Transcriptional Target of SMK-1

A second mechanism by which SMK-1 might regulate daf-16 dependent longevity is through regulation of daf-16 transcription or protein levels. Again, this possibility seemed unlikely because levels of daf-16 observed using a daf-16::gfp fusion gene under control of the endogenous daf-16 promoter were not diminished in animals treated with smk-1 RNAi, and western blot analysis indicated that the levels of DAF-16-GFP were not diminished. Additionally, using quantitative PCR, no decrease in daf-16 mRNA levels in daf-2(e1370) animals treated with smk-1 RNAi was observed. Thus, smk-1 does not to appear to regulate daf-16 transcription directly or to alter protein levels to a detectable extent. This again suggests that smk-1 must affect daf-16 dependent longevity by another mechanism.

Example 12

Nuclear Entry of DAF-16 is Independent of SMK-1

In wild-type animals, DAF-16 is predominantly localized in the cytoplasm as a result of inhibitory phosphorylation of Ser/Thr residues by the AKT and SGK kinases. However, in long-lived daf-2 mutant animals, DAF-16 accumulates in the nucleus due to a lack of inhibitory phosphorylation at these sites (Henderson and Johnson, 2001; Hertweck et al., 2004; Lin et al., 2001). smk-1 was tested to determine whether SMK-1 was required for the nuclear accumulation of DAF-16. Using a complementing daf-16::gfp fusion gene (Henderson and Johnson, 2001), wild type animals treated with daf-2 RNAi readily accumulated DAF-16-GFP protein within their nuclei, as monitored by the nuclear accumulation of the GFP fluorescence signal. As a negative control, animals treated simultaneously with both daf-2 and daf-16 RNAi had a diminished GFP signal, presumably due to daf-16 RNAi acting on the daf-16::gfp fision gene product. Interestingly, and in contrast to results obtained using daf-16 RNAi, animals treated simultaneously with daf-2 and smk-1 RNAI accumulated DAF-16-GFP in nuclei to the same degree as animals treated with an equally diluted mixture of daf-2 and control RNAi plasmid. Thus, in response to decreased insulin/IGF-1 signaling, DAF-16 can still enter the nucleus of cells that have reduced smk-1 activity. It is important to note, however, that despite the nuclear accumulation of DAF-16, in the absence of smk-1, nuclear localized DAF-16 did not result in increased lifespan, supporting previous conclusions that nuclear entry of DAF-16 is not sufficient for increased longevity (Lin et al., 2001).

Example 13

Nuclear Entry of SMK-1 is Independent of DAF-16

Because nuclear entry of DAF-16 was not dependent upon smk-1, smk-1 was tested to determine whether nuclear entry of SMK-1 was dependent upon daf-16. Using the smk-1::gfp strain, treatment of animals with either daf-16 or daf-2 RNAi did not alter nuclear accumulation of SMK-1-GFP as measured by fluorescence of the GFP. Therefore, SMK-1 nuclear localization is independent of DAF-16, and, unlike DAF-16, SMK-1 is localized to the nucleus of intestinal cells regardless of IIS status.

The data from these four sets of experiments indicate that SMK-1 and DAF-16 do not appear to co-regulate expression or influence each other's nuclear entry, indicating that SMK-1 affects DAF-16 activity in some other manner. The nuclear localization of SMK-1 suggests that SMK-1 could directly influence DAF-16 transcriptional activity.

Example 14

SMK-1 is Required for DAF-16 Transcriptional Activity

Based on the RNAi data, one would predict that loss of smk-1 should reduce transcription of DAF-16-dependent genes. Therefore, we asked whether smk-1 RNAi could influence the mRNA levels of well-characterized DAF-16 target genes. Using daf-2(e1370) mutant worms expressing an integrated sod-3::gfp reporter construct, smk-1 RNAi reduced the normally robust GFP reporter expression of this strain. These effects were quantified using a fluorimeter to measure the levels of sod-3::gfp expression in an entire population of worms. In the daf-2(e1370) mutant background, reduced smk-1 activity resulted in a decrease of sod-3::gfp expression comparable to that seen in animals treated with daf-16 RNAi. In each case the reduction was approximately 20%. These results were also confirmed using Q-PCR to analyze the endogenous sod-3 transcript of daf-2(e1370) animals treated with either daf-16 or smk-1 RNAi. In each case, the respective RNAi reduced the RNA expression by 60-70%.

FOXO3a and DAF-16 function as both transcriptional activators and repressors (Jia et al., 2004) (Schmidt et al., 2002). SMK-1 was examined to determine whether it was also required for the repressor activity of DAF-16. Using Q-PCR, daf-15 was tested to determine whether it, a gene that is transcriptionally repressed by DAF-16 (Jia et al., 2004), was also repressed in the absence of smk-1. In daf-2(e1370) mutant animals, daf 15 expression was repressed by nuclear DAF-16. However, reduced daf-16 resulted in upregulation of daf-15 transcripts more than 150% as determined by QPCR. In a similar manner, reduced smk-1 also resulted in increased expression of daf-15 mRNA more than 50% as determined by QPCR, suggesting that SMK-1 is required for the transcriptional repressor activity of DAF-16.

Human SMEK-1 was tested to determine whether it functioned as a transcriptional regulator of human FOXO proteins. Using a synthetic FOXO luciferase reporter containing three tandem IRS (insulin response sequences) elements, increased levels of SMEK-1 enhanced transcription of these FOXO3a reporter genes in transient assays in 293 and HepG2 cells. The enhanced transcription in 293 cells showed an increase in FOXO3a-mediated transcription that was dose dependent with a 12-fold increase in expression at the highest levels of SMEK-1 supplied. The enhanced transcription in the HepG2 cells was more robust with a triple phosphorylation mutant of FOXO3a (FOXO3a-TM) that is constitutively nuclear and therefore hyperactive with the FOXO3a-TM cell line showing nearly double the activity when supplemented with SMEK-1 where the FOXO3a wild type cell line only showing a fifty percent increase with the same amount of SMEK-1. Similar dose-dependent transcriptional activation was also observed with hyperactivated AFX (AFX-AAA), another FOXO homolog in mammalian cells. SMEK-1's ability to enhance expression of a known FOXO target gene was examined by measuring transcriptional activity of the native GADD45 promoter. Overexpression of SMEK-1 alone resulted in increased levels of GADD45 reporter activity that showed dose dependent increase in activity. Activation of the native promoter was further enhanced by co-expression of both SMEK-1 and FOXO3a. The enhancement of transcription due to SMEK-1 seems to require co-expression of FOXO3a when synthetic FOXO reporters were used; however, SMEK-1 alone was sufficient to activate the native promoter, at least partially. Finally, consistent with the repression of daf-15 expression by SMK-1 in worms, a Gal4DB-SMEK-1 fusion protein showed dose-dependent capacity for repressor activity in a Gal4-luciferase reporter gene assay.

Taken together, the requirement for SMK-1 for the transcriptional induction of sod-3::gfp and the transcriptional repression of daf-15, and the evidence that mammalian SMEK-1 enhances the transcriptional activity of both synthetic and endogenous FOXO3a reporters in mammalian cell lines, support a model in which SMK-1 functions as a transcriptional cofactor for DAF—16/FOXO3a.

Example 14 smk-1 Regulates Longevity Independent of Insulin/IGF-1's Roles in Development and Reproduction In worms the insulin/IGF-1 pathway independently regulates dauer development, reproductive timing and longevity (Dillin et al., 2002a). Because smk-1 is required for daf-16-dependent longevity, smk-1 was tested to determine whether it was also required for daf-16 to regulate the dauer development and reproductive functions. In fact, reduced smk-1 activity did not alter dauer development or reproductive timing. While wild-type animals treated with smk-1 RNAi did not enter dauer diapause at 25° C., daf-2(e1370) mutant animals treated with smk-1 R(NAI arrested as dauers at 25° C. Additionally, daf-2(e1370) mutant animals paused for 24 hr during the L2 larval stage at the permissive temperature when treated with smk-1 RNAi but not when treated with daf-16 RNAi. These results indicate that smk-1 does not play a role in dauer larval development.

In addition, reduced smk-1 activity in either wild-type or daf-2(e1370) mutant animals did not affect reproduction. For example, wild-type animals treated with smk-1 RNAi reproduced at the same rate as animals on control bacteria, and daf-2(e1370) mutant animals had a protracted reproductive schedule that was nearly identical to daf-2(1370) mutant animals treated with smk-1 RNAi. Thus, consistent with previous studies, the insulin/IGF-1 pathway can diverge to regulate the timing of reproduction independently of longevity (Dillin et al., 2002a). SMK-1 is not required for daf-2 dependent entry into dauer or daf-2 dependent extension of reproduction. Thus, SMK-1 appears to be unique in being a factor that is solely required for the longevity function of DAF-16.

Example 15

Generation of Smek Plasmids and Antibodies

HA-tagged FOXO3a, FOXO4 (AFX) and FOXO4-TM expression constructs were kindly provided by K. Arden (UCSD). pECE/FOXO3a and pECEiFOXO3a-TM were gifts from M. Greenberg (Harvard). FLAG-tagged p38 MAPK plasmids and GST-ATF2 plasmid were gifts from J. Han (Scripps). pGAD45-luc reporter was a gift from N. Motoyama (National Institute for Longevity Sciences, Japan). Human Catalase-luc plasmid was a gift from T. Finkel (NIH). cDNA for human Smek1 splice form Smek1-S1 was provided by S. Sugano (University of Tokyo). The C-terminal sequences of Smek1 full-length were constructed by subcloning inserts from two EST clones A1638670 (SphI/EcoRV) and BG676909 (EcoRV/SacI) (The I.M.A.G.E. Consortium) into Sp72 vector cut with SphI and SacI. Plasmid for GST-Smek1 was constructed by joining a PCR fragment of Smek1-S1 (XbaI/SphI) with Smek1 C-terminal fragment (SphI/XhoI). GFP-Smek-S1 and GFP-Smek1 plasmids were created by PCR amplification and subcloning of the corresponding Smek1 fragments (KpnI/XhoI) into pEGFPN1 (KpnI/XhoI) (Clontech). FLAG-tagged Smek1 constructs were made by PCR and subcloning of Smek1 sequence (SpeI/NotI) into a modified pEGFPN1 plasmid containing three copies of FLAG tag sequence but missing the GFP sequence (pFLA3). Smek1-5A mutant was created using site-directed mutagenesis and subcloned into pGexKG and pFLA3 vectors, respectively. Anti-Smek1 antibodies were raised in rabbits immunized with a synthetic peptide of human Smek1.

Example 16

Cell Culture

HeLa cells, 293 cells, 293T cells and HepG2 cells were cultured in DMEM supplemented with 10% fetal calf serum and the antibiotics penicillin and streptomycin at 37° C. 293 cells and 293T cells were transfected using the calcium phosphate method or the Effectene reagents (Qiagen). HepG2 cells were transfected using the FuGene 6 reagent (Roche).

A. Microscopy

Cells transfected with GFP-tagged constructs were fixed in 3.7% formaldehyde for microcopy analysis using the Deltavision deconvolution microscope. For immunofluorescence staining, untransfected cells were fixed and permeablized in PBS containing 0.2% Triton X-100, blocked with normal goat serum and stained with antibodies. Cell nuclei were visualized by staining with Hoescht dye.

B. Immunoblotting and Immunoprecipitation

For western blotting and immunoprecipitation, cells were lysed in RIPA buffer without SDS in the presence of protease inhibitors. The protein concentration of cell lysates was determined using the Bio-Rad DC Protein Assay kit. Lysates were either mixed with an equal volume of 2× sample buffer and boiled for 5 min or subjected to immunoprecipitation. The phosphatase treatment of immunoprecipitated Smek1 was described previously (Meisenhelder, Suh et al. 1989).

For co-immunoprecipitation studies, cells were extracted in NP40 lysis buffer (20 mM Hepes, pH 7.4, 2 mM EDTA, 2 mM EGTA, 100 mM NaCl, 50 mM NaF, 1 mM $Na_3VO_4$, 1% NP40) plus protease inhibitors, clarified by centrifugation at 15,000×g at 4° C. for 10 min, incubated with anti-FLAG antibodies immobilized on protein A Sepharose beads for 2-4 hrs at 4° C., wash four times with lysis buffer plus protease inhibitors, and resuspended in equal volume of 2× sample buffer for western blot analysis.

Example 17

Kinase Assays

Activated JNK MAPKs were precipitated from 293T cells using anti-JNK antibodies and assayed using GST fusion proteins purified from BL21 strain as substrates as described elsewhere (Perlman, Schiemann et al. 2001). Activated FLAG-tagged p38 MAPKs were precipitated from 293T cells using anti-FLAG antibodies and assayed according to method described previously (Jiang, Chen et al. 1996).

Example 18

Luciferase Assays

HepG2 cells from one 50-70% confluent 10 cm dish were split into one 12-well plate for transfection. 293 cells and 293T cells were seeded in 12-well plates at a density of $5\times10^4$ cells/well. Cells were transfected with Luciferase reporter construct, H-Ras-LacZ construct together with various combinations of Smek1, FOXO3a plasmids. Two days after the transfection, cells were lysed in 100 µl of lysis buffer and one fifth of the lysates were used in luciferase assay according to the Promega protocol. β-galactosidase activity was assayed as described elsewhere (Conkright, Canettieri et al. 2003).

Example 19

C. elegans Methods and Generation of Transgenic Lines

CF1037: daf-16(mu86)I, CF1041: daf-2(e1370)III, CB4037: glp-1 (e2141)III, MQ887: isp-1(qm150)V, MQ167: clk-1(qm30)IV, CF1580: daf-2(e1370)III; muIs84{pAD76 (sod-3:.gfp)} (Libina et al., 2003), CF1553: muIs84{pAD76 (sod-3::gfp)} (Libina et al., 2003). Wild-type C. elegans (N2) strains were obtained from the Caenorhaditis Genetics Center. Nematodes were handled using standard methods (Brenner, 1974). For generation of AD24, AD25, and AD26 transgenic animals, plasmid DNA containing the pAD187 (smk-1::gfp) construct was mixed at 18 µg/ml with 20 µg/ml of pRF4(rol-6) construct (Mello et al., 1991). Worms used as controls in lifespans against smk-1 overexpressing strains contained 75 µg/ml of pRF4(rol-6) injected with 75 µg/ml of pAD158 (ges-1::gfp). Mixtures were microinjected into the gonads of adult hermaphrodite animals by using standard methods (Mello et al., 1991). Transgenic F1 progeny were selected on the basis of roller phenotype. Individual transgenic F2 animals were picked to establish independent lines.

Example 20

Lifespan Analysis

Lifespan analyses were performed as described previously (Dillin et al., 2002). Eggs from strains grown at 20° C. degrees were transferred to plates seeded with RNAi bacteria (BL21-DE3). Adult animals were scored every other day for viability. Animals were judged as dead when they ceased pharyngeal pumping and did not respond to prodding with a platinum wire at least three times. During their reproductive period, animals were transferred to new plates every other day. At the end of their reproductive period, animals were transferred to new plates at least once per week. The prefertile period of adulthood was used as t=0 for lifespan analysis. Strains were grown at 20° C. at optimal growth conditions for at least two generations before use in lifespan analysis. All lifespan analysis were conducted at 20° C. unless otherwise stated, Statview 5.01 (SAS) software was used for statistical analysis and to determine means and percentiles. In all cases, P values were calculated using the log-rank (Mantel-Cox) method.

Example 21

Dauer Formation Assays

Eggs from daf-2(e1370) reproductive animals were transferred to plates seeded with RNAi bacteria and shifted to 25° C. for three days. Dauer formation was determined based upon morphology using a dissecting microscope. Percentage dauer formation was determined relative to empty vector and daf-16 RNAi treated animals.

Example 22

Reproductive Assays

N2 eggs were incubated at 20° C. on plates seeded with various RNAi treatments. Worms were synchronized within one hour at the L1 stage upon hatching. Late L4 stage worms were picked and transferred to fresh RNAI plates every 12 hours for 4-5 days. After this period, the worms were transferred every 24 hr. All plates were then incubated at 20° C. for about 2 days and shifted to 4° C. The number of worms that developed was determined at the end of the experiment. For RNAi treatments that resulted in embryonic lethality, eggs were counted instead of hatched progeny.

Example 23

RNA Isolation and Quantitative RT-PCR

Total RNA was isolated from synchronized populations of approximately 50,000 prefertile or day 1 reproductive animals. Animals were removed from plates and washed two times with M9 buffer followed by one time in DEPC water. Total RNA was extracted using TRIzol reagent (Gibco). cDNA was created from 6 µg of RNA added to 2x reaction buffer using Superscript II RT (Invitrogen). SybrGreen real time qPCR experiments were performed as described in the manual using ABI Prism7900HT (Applied Biosystems). Primers and probes are listed below:

Primers:

```
act-1 forward
GAGCACGGTATCGTCACCAA          (SEQ ID NO 12)

act-1 reverse
TGTCATGCCAGATCTTCTCCAT        (SEQ ID NO 13)

sod-3 forward
CTAAGGATGGTGGAGAACCTTCA       (SEQ ID NO 14)

sod-3 reverse
CGCGCTTAATAGTGTCCATCAG        (SEQ ID NO 15)

smk-1a forward
ACCAACAGAGATCATATTCTTGACCAT   (SEQ ID NO 16)

smk-1a reverse
GGTTGCGTCTCGTTTTATATCAAGAT    (SEQ ID NO 17)

daf-16a forward
GGAAGAACTCGATCCGTCACA         (SEQ ID NO 18)

daf-16a reverse
TTCGCATGAAACGAGAATGAAG        (SEQ ID NO 19)

daf-15 forward
GCAATGTGTTCCCGTTTTTAGTG       (SEQ ID NO 20)

daf-15 reverse
```

```
TAAGTCAGCACATGTTCGAAGTCAA     (SEQ ID NO 21)
```

Example 24

GFP Localization

Paralyzed day one reproductive adult transgenic animals were assayed for GFP expression at 10x or 63x magnification using a Leica 6000B digital microscope. When comparing fluorescence between samples of differentially RNAi treated animals, only non-saturating pictures using fixed times of exposure were taken. Images were acquired using Leica FW4000 software.

Example 25

Fluorimetry

Eggs from daf-2 (e1370);sod-3:gfp reproductive animals were transferred to plates seeded with RNAi bacteria or empty vector controls. Eggs treated with daf-16 RNAi were transferred one day later to compensate for developmental delays seen in daf-2 mutant strains. Upon day one of adulthood, three populations of forty worms for each treatment were picked and placed in wells containing M9 buffer. As a control, populations of day one adults were picked from N2 worms that did not contain GFP expressing constructs. All measures of fluorescence occurred immediately after transfer.

Fluorescence was measured using the HTS 7000 Plus Bio-Assay Reader at a fixed gain of 110. Fluorescence was determined for each population in triplicate after shaking of the well to redistribute the worms. Fluorescence was measured using a six spot check. Levels of fluorescence were normalized to background levels seen in the non-fluorescent strain. The experiment was repeated at least three times using independently grown populations of worms.

Example 26

RNAi Constructs

RNAi treated strains were fed E. coli (HT115) containing an empty control vector pAD12 (Dillin et al., 2002a) or E. coli expressing double-stranded RNAi against the genes daf-16 (pAD43, Dillin et al., 2002a), daf-2 (pAD48, Dillin et al., 2002a), smk-1 (from the Ahringer RNAI library, Simmer et al., 2003) or cyc-1 (from the Ahringer RNAi library, Simmer et al., 2003).

Example 27

Creation of smk-1::gfp Constructs

To construct the plasmid expressing SMK-1-GFP driven by smk-1 endogenous promoter, sequences 3 kb upstream of smk-1 coding region were amplified from genomic DNA by PCR and inserted upstream of GFP sequences in the worm expression vector pAD1. Full-length smk-1 cDNA was amplified as N'- and C'-fragments from a first strand worm cDNA library by PCR. The N' fragment was digested with NotI and BglI, and the C' fragment was digested with BglII and KpnI, respectively. Both fragments were ligated and inserted downstream of the promoter sequences in-frame with the GFP sequence at the C-terminus. Primers for N' fragment: Forward-GTTTTGCGGCCGCATG TCGGACA-CAAAAGAGGTATC (SEQ ID NO 22), Reverse-AGTGC-CAGATCTC(GCCGACG (SEQ ID NO 23). Primers for C' fragment: Forward-TGCTGCCCTCCCGGCATCTC (SEQ ID NO 24), Reverse-GTTTTGGTACCCTGGCCTGC-GAAACTGTGGC (SEQ ID NO 25).

Example 28

Creation and Affinity Purification of SMK-1 Antibody

A rabbit polyclonal antiserum against worm SMK-1 was generated using a GST-fusion protein containing the last C-terminal 114 amino acid residues of SMK-1. To affinity purify the SMK-1 antibody, rabbit anti-SMK-1 serum was incubated overnight at 4° C. with the corresponding antigen immobilized on PVDF membrane and eluted with 100 mM glycine (pH 2.5) followed by neutralization with Tris (pH 8.4).

Example 29

Immunofluorescence Microscopy

Briefly, worms were pre-fixed with 3% paraformaldehyde for 15 min, followed by freeze and crack treatment on poly-L-lysine coated ring slides. After blocking non-specific staining by incubating worms in TRIS-buffered saline (TBS) containing 5% BSA (TBSB), worms were incubated with affinity purified anti-SMK-1 antibodies overnight at 4° C., rinsed with TBSB and subsequently incubated with goat anti-rabbit FLAX 568 in TBSB. After gentle washing, samples were mounted in GEL/MOUNT (Biomeda) for immunofluorescence microscopy.

REFERENCES

The following references are hereby incorporated by reference in their entirety.

Alonso, G., C. Ambrosino, et al. (2000). "Differential activation of p38 mitogen-activated protein kinase isoforms depending on signal strength." J Biol Chem 275(51): 40641-8.

Brunet, A., A. Bonni, et al. (1999). "Akt promotes cell survival by phosphorylating and inhibiting a Forkhead transcription factor." Cell 96(6): 857-68.

Brunet, A., L. B. Sweeney, et al. (2004). "Stress-dependent regulation of FOXO transcription factors by the SIRT1 deacetylase." Science 303(5666): 2011-5.

Burgering, B. M. and G. J. Kops (2002). "Cell cycle and death control: long live Forkheads." Trends Biochem Sci 27(7): 352-60.

Chang, L. and M. Karin (2001). "Mammalian MAP kinase signalling cascades." Nature 410(6824): 37-40.

Conkright, M. D., G. Canettieri, et al. (2003). "TORCs: transducers of regulated CREB activity." Mol Cell 12(2): 413-23.

Dijkers, P. F., K. U. Birkenkamp, et al. (2002). "FKHR-L1 can act as a critical effector of cell death induced by cytokine withdrawal: protein kinase B-enhanced cell survival through maintenance of mitochondrial integrity." J Cell Biol 156(3): 531-42.

Dillin, A., Crawford, D. K., and Kenyon, C. (2002a). Timing requirements for insulin/IGF-1 signaling in C. elegans. Science 298, 830-834.

Dillin, A., Hsu, A. L., Arantes-Oliveira, N., Lehrer-Graiwer, J., Hsin, H., Fraser, A. G., Kamath, R. S., Ahringer, J., and Kenyon, C. (2002b). Rates of behavior and aging specified by mitochondrial function during development. Science 298, 2398-2401.

Enslen, H., D. M. Brancho, et al. (2000). "Molecular determinants that mediate selective activation of p38 MAP kinase isoforms." Embo J 19(6): 1301-11.

Feng, J., Bussiere, F. and S. Hekimi (2001). Mitochondrial Electron Transport is a Key Determinant of Life Span in Caenorhabditis elegans. Developmental Cell 1, 663-644.

Garsin, D. A., Villanueva, J. M., Begun, J., Kim, D. H., Sifri, C. D., Calderwood, S. B., Ruvkun, G., and Ausubel, F. M. (2003). Long-lived C. elegans daf-2 mutants are resistant to bacterial pathogens. Science 300, 1921.

Guarente, L. and C. Kenyon (2000). "Genetic pathways that regulate ageing in model organisms." Nature 408(6809): 255-62.

Hekimi, S. and L. Guarente (2003). "Genetics and the specificity of the aging process." Science 299(5611): 1351-4.

Henderson, S. T., and Johnson, T. E. (2001). daf-16 integrates developmental and environmental inputs to mediate aging in the nematode Caenorhabditis elegans. Curr Biol 11, 1975-1980.

Hertweck, M., Gobel, C., and Baumeister, R. (2004). C. elegans SGK-1 is the critical component in the Akt/PKB kinase complex to control stress response and life span. Dev Cell 6, 577-588.

Jia, K., Chen, D., and Riddle, D. L. (2004). The TOR pathway interacts with the insulin signaling pathway to regulate C. elegans larval development, metabolism and life span. Development 131, 3897-3906.

Jiang, Y., C. Chen, et al. (1996). "Characterization of the structure and function of a new mitogen-activated protein kinase (p38beta)." J Biol Chem 271(30): 17920-6.

Jonassen, T., Larsen, P. L., and Clarke, C. F. (2001). A dietary source of coenzyme Q is essential for growth of long-lived Caenorhabditis elegans clk-1 mutants. Proc Natl Acad Sci USA 98, 421-426.

Kamath, R. S., Fraser, A. G., Dong, Y., Poulin, G., Durbin, R., Gotta, M., Kanapin, A., Le Bot, N., Moreno, S., Sohrmann, M., et al. (2003). Systematic functional analysis of the Caenorhabditis elegans genome using RNAi. Nature 421, 231-237.

Kenyon, C. (2001). "A conserved regulatory system for aging." Cell 105(2): 165-8.

Lee, S. S., Lee, R. Y., Fraser, A. G., Kamath, R. S., Ahringer, J., and Ruvkun, G. (2003b). A systematic RNAi screen identifies a critical role for mitochondria in C. elegans longevity. Nat Genet. 33, 40-48.

Libina, N., Berman, J. R., and Kenyon, C. (2003). Tissue-specific activities of C. elegans DAF-16 in the regulation of lifespan. Cell 115, 489-502.

Lin, K., Hsin, H., Libina, N., and Kenyon, C. (2001). Regulation of the Caenorhabditis elegans longevity protein DAF-16 by insulin/IGF-1 and germline signaling. Nat Genet. 28, 139-145.

McCarroll, S. A., Murphy, C. T., Zou, S., Pletcher, S. D., Chin, C. S., Jan, Y. N., Kenyon, C., Bargmann, C. I., and Li, H. (2004). Comparing genomic expression patterns across species identifies shared transcriptional profile in aging. Nat Genet. 36, 197-204.

McElwee, J. J., Schuster, E., Blanc, E., Thomas, J. H., and Gems, D. (2004). Shared Transcriptional Signature in Caenorhabditis elegans Dauer Larvae and Long-lived daf-2 Mutants Implicates Detoxification System in Longevity Assurance. J Biol Chem 279, 44533-44543.

Meisenhelder, J., P. G. Suh, et al. (1989). "Phospholipase C-gamma is a substrate for the PDGF and EGF receptor protein-tyrosine kinases in vivo and in vitro." Cell 57(7): 1109-22.

Miyadera, H., Amino, H., Hiraishi, A., Taka, H., Murayama, K., Miyoshi, H., Sakamoto, K., Ishii, N., Hekimi, S., and Kita, K. (2001). Altered quinone biosynthesis in the long-lived elk-1 mutants of Caenorhabditis elegans. J Biol Chem 276, 7713-7716.

Morrison, D. K. and R. J. Davis (2003). "Regulation of MAP kinase signaling modules by scaffold proteins in mammals." Annu Rev Cell Dev Biol 19: 91-118.

Motta, M. C., N. Divecha, et al. (2004). "Mammalian SIRT1 represses forkhead transcription factors." Cell 116(4): 551-63.

Murphy, C. T., McCarroll, S. A., Bargmann, C. I., Fraser, A., Kamath, R. S., Ahringer, J., Li, H., and Kenyon, C. (2003). Genes that act downstream of DAF-16 to influence the lifespan of Caenorhabditis elegans. Nature 424, 277-283.

Nasrin, N., S. Ogg, et al. (2000). "DAF-16 recruits the CREB-binding protein coactivator complex to the insulin-like growth factor binding protein 1 promoter in HepG2 cells." Proc Natl Acad Sci USA 97(19): 10412-7.

Perlman, R., W. P. Schiemann, et al. (2001). "TGF-beta-induced apoptosis is mediated by the adapter protein Daxx that facilitates JNK activation." Nat Cell Biol 3(8): 708-14.

Puigserver, P., Rhee, J., Donovan, J., Walkey, C. J., Yoon, J. C., Oriente, F., Kitamura, Y., Altomonte, J., Dong, H., Accili, D., and Spiegelman, B. M, (2003). Insulin-regulated hepatic gluconeogenesis through FOXO1-PGC-1alpha interaction. Nature 423, 550-555.

Puigserver, P., and Spiegelman, B. M. (2003). Peroxisome proliferator-activated receptor-gamma coactivator 1 alpha (PGC-1 alpha): transcriptional coactivator and metabolic regulator. Endocr Rev 24, 78-90.

Simmer, F., Moorman, C., van der Linden, A. M., Kuijk, E., van den Berghe, P. V., Kamath, R. S., Fraser, A. C., Ahringer, J., and Plasterk, R. H. (2003). Genome-wide RNAi of C. elegans using the hypersensitive rrf-3 strain reveals novel gene functions. PLoS Biol 1, E12.

Volkman, B. F., K. E. Prehoda, et al. (2002). "Structure of the N-WASP EVH1 domain-WIP complex: insight into the molecular basis of Wiskott-Aldrich Syndrome." Cell 111 (4): 565-76.

Wang, M. C., D. Bohmann, et al. (2003). "JNK signaling confers tolerance to oxidative stress and extends lifespan in Drosophila." Dev Cell 5(5): 811-6.

TABLE 1

Effects of smk-1 RNAi on lifespan and brood size.

| Treatment | Mean Lifespan ± s.e.m. (days) | P† | 75th Percentile* (days) | Average Brood Size ± SD[Δ] | (Total #Animals Died/Total)[§] |
|---|---|---|---|---|---|
| daf-2(e1370) mutant worms 20° C. | | | | | |
| Vector (control) | 48.2 ± 1.2 | | 56 | | 49/64 |
| daf-16 RNAi | 24.6 ± 0.6 | <0.0001 ‡ | 27 | | 45/65 |
| smk-1 RNAi | 26.6 ± 1.5 | <0.0001 ‡, 0.0528[a] | 34 | | 57/64 |
| glp-1(e2141) mutant worms 25° C. | | | | | |
| Vector (control) | 22.1 ± 0.9 | | 28 | N.D. | 74/80 |
| daf-16 RNAi | 11.5 ± 0.3 | <0.0001 ‡ | 14 | N.D. | 76/86 |
| smk-1 RNAi | 11.7 ± 0.3 | <0.0001 ‡, 0.5459[a] | 14 | N.D. | 67/81 |
| isp-1(qm150) mutant worms 20° C. | | | | | |
| Vector (control) | 32.8 ± 1.8 | | 40 | N.D. | 24/55 |
| daf-16 RNAi | 20.1 ± 0.9 | <0.0001 ‡ | 24 | N.D. | 42/79 |
| smk-1 RNAi | 26.1 ± 1.0 | 0.0001 ‡, <0.0001 ‡ | 31 | N.D. | 31/76 |
| N2 20° C. | | | | | |
| Vector (control) | 17.5 ± 0.5 | | 20 | | 46/78 |
| cyc-1 RNAi (Complex III) | 32.9 ± 1.4 | <0.0001 ‡ | 44 | N.D. | 51/80 |
| cyc-1 & daf-16 RNAi | 25.7 ± 1.1 | <0.0001[b] | 33 | N.D. | 60/78 |
| cyc-1 & smk-1 RNAi | 25.6 ± 0.9 | <0.0001[b], 0.6683[c] | 30 | N.D. | 65/79 |
| daf-2 RNAi | 35.8 ± 1.9 | | 48 | N.D. | 56/79 |
| daf-2 & cyc-1 RNAi | 45.0 ± 2.0 | <0.0001[d] | 60 | N.D. | 71/80 |
| smk-1 RNAi clk-1(qm30) | 14.5 ± 0.4 | <0.0001 ‡ | 16 | | 70/79 |

TABLE 1-continued

Effects of smk-1 RNAi on lifespan and brood size.

| Treatment | Mean Lifespan ± s.e.m. (days) | P† | 75th Percentile* (days) | Average Brood Size ± SD^Δ | (Total #Animals Died/Total)§ |
|---|---|---|---|---|---|
| mutant worms 20° C. | | | | | |
| Vector (control) | 19.3 ± 1.1 | | 24 | N.D. | 66/80 |
| daf-16 RNAi | 15.5 ± 0.7 | 0.0058 ‡ | 17 | N.D. | 55/79 |
| smk-1 RNAi | 16.6 ± 0.7 | 0.1405 ‡, 0.1768[a] | 17 | N.D. | 50/80 |
| daf-16(mu86) mutant worms 20° C. | | | | | |
| Vector (control) | 10.8 ± 0.4 | | 14 | N.D. | 53/80 |
| smk-1 RNAi | 10.6 ± 0.3 | 0.3810 ‡ | 11 | N.D. | 61/80 |

*The 75th percentile is the age when the fraction of animals alive reaches 0.25.
†P values were calculated for individual experiments, each consisting of control and experimental animals examined at the same time.
§The total number of observations equals the number of animals that died plus the number censored. Animals that crawled off the plate, exploded or bagged were censored at the time of the event. Control and experimental animals were cultured in parallel and transferred to fresh plates at the same time. The logrank (Mantel-Cox) test was for statistical analysis.
^Δ Average brood size was calculated from the total brood size of at least 15 animals cultured independently in each trial.
‡ Compared with worms grown on HT115 bacteria harboring the RNAi plasmid vector which were analyzed at the same time.
[a] Compared to worms cultured continuously on HT115 bacteria harboring the daf-16 RNAi plasmid Egg (□, at 20° C., which were analyzed at the same time.
[b] Compared to worms cultured continuously on HT115 bacteria harboring the cyc-1 RNAi plasmid which were analyzed at the same time.
[c] Compared to worms cultured continuously on mixed cultures of HT115 bacteria harboring the cyc-1 and daf-16 RNAi plasmid which were analyzed at the same time.
[d] Compared to worms cultured continuously on HT115 bacteria harboring the daf-2 RNAi plasmid which were analyzed at the same time.

What is claimed is:

1. A method of identifying a compound that binds to a Suppressor of MEK null polypeptide (Smek protein) comprising:
  contacting the Smek protein with a compound; and
  measuring binding between the compound and the Smek protein.

2. The method of claim 1 wherein the Smek protein is SEQ ID NO:1.

3. The method of claim 1 wherein the Smek protein is SEQ ID NO:2.

4. The method of claim 1 wherein the Smek protein is 90% identical to SEQ ID NO:1 wherein said Smek protein has affinity for FOXO transcription factors.

5. The method of claim 1 wherein the Smek protein is 90% identical to SEQ ID NO:2 wherein said Smek protein has affinity for FOXO transcription factors.

* * * * *